(12) United States Patent
Rodrigues et al.

(10) Patent No.: US 8,729,042 B2
(45) Date of Patent: May 20, 2014

(54) TREATING OCULAR DISEASES USING PEROXISOME PROLIFERATOR—ACTIVATED RECEPTOR DELTA ANTAGONISTS

(75) Inventors: Gerard A. Rodrigues, Laguna Niguel, CA (US); John E. Donello, Dana Point, CA (US)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 13/281,290

(22) Filed: Oct. 25, 2011

(65) Prior Publication Data

US 2012/0136041 A1 May 31, 2012

Related U.S. Application Data

(62) Division of application No. 12/524,217, filed as application No. PCT/US2008/052189 on Jan. 28, 2008, now abandoned.

(60) Provisional application No. 60/887,178, filed on Jan. 30, 2007.

(51) Int. Cl.
*A61K 48/00* (2006.01)

(52) U.S. Cl.
USPC .......................................... 514/44; 536/24.5

(58) Field of Classification Search
CPC .......................... C12N 15/111; C12N 2310/14
See application file for complete search history.

(56) References Cited

U.S. PATENT DOCUMENTS

| | | | |
|---|---|---|---|
| 6,316,465 B1 * | 11/2001 | Pershadsingh et al. ....... | 514/310 |
| 7,691,997 B2 | 4/2010 | Khvorova | |
| 2003/0143732 A1 * | 7/2003 | Fosnaugh et al. ............. | 435/325 |
| 2003/0224514 A1 * | 12/2003 | Gaarde et al. ................. | 435/375 |
| 2004/0235019 A1 | 11/2004 | Chapman | |
| 2004/0259247 A1 * | 12/2004 | Tuschl et al. .................. | 435/375 |
| 2005/0004183 A1 | 1/2005 | Henry | |
| 2005/0020652 A1 | 1/2005 | Gibson | |
| 2005/0020654 A1 | 1/2005 | Pershadsingh | |
| 2005/0080140 A1 | 4/2005 | Hatae | |
| 2005/0095239 A1 | 5/2005 | Rebeck | |
| 2005/0095677 A1 | 5/2005 | Liu | |
| 2005/0191668 A1 | 9/2005 | Zhou | |
| 2005/0233361 A1 | 10/2005 | Clerc | |
| 2005/0255487 A1 | 11/2005 | Khvorova et al. | |
| 2006/0052627 A1 | 3/2006 | Diaz | |
| 2006/0116416 A1 | 6/2006 | Lin | |
| 2006/0135540 A1 | 6/2006 | Lin | |
| 2006/0160867 A1 | 7/2006 | Freedman | |
| 2006/0160894 A1 | 7/2006 | Fernandez | |
| 2006/0167012 A1 | 7/2006 | Noble | |
| 2006/0167058 A1 | 7/2006 | Yamazaki | |
| 2006/0189667 A1 | 8/2006 | Yamazaki | |
| 2006/0217332 A1 | 9/2006 | Vargeese et al. | |
| 2006/0217374 A1 | 9/2006 | Conner | |
| 2006/0217425 A1 | 9/2006 | Burton | |
| 2006/0241157 A1 | 10/2006 | Conner | |

FOREIGN PATENT DOCUMENTS

WO   WO 2004/076622      9/2004

OTHER PUBLICATIONS

Shearer et al. (Biochim et Biophys Acta, 2007, 0771:1082-1093).*
Reilly et al. (FEBS Letters 2008, 582:26-31).*
Luguet et al. (Biochim et Biophys Acta 2005: 313-317).*
Zhang, L., et al., Blockage of PPARδ Increases the Expression of Inflammatory Factors in 3T3-L1 Cells Stimulated with TNFα, J. Med. Coll. PLA 21(2): 77-81 (2006).
Wilson, T.M., et al., The PPARs : From Orphan Receptors to Drug Discovery, J. Med. Chem. 43(4): 527-550 (2000).
Wang, D., et al., Crosstalk Between Peroxisome Proliferator-Activated Receptor δ and VEGF Stimulates Cancer Progression, PNAS 103(50): 19069-19074 (2006).
Pushparaj, P.N. and Melendez, A.J., Short Interfering RNA (siRNA) as a Novel Therapeutic, Clin. Exper. Pharmacol. Physiol. 33: 540-510 (2006).
Piqueras, L., et al., Activation of PPARβ/δ Induces Endothelial Cell Proliferation and Angiogenesis, Arterioscler. Thromb. Vasc. Biol. 27:1-7 (2006).
Jarvis et al, "Both PPARgamma and PPARdelta influence sulindac sulfide-mediated p21WAF1/CIP1 upregulation in a human prostate epithelial cell line", Oncogene, vol. 24, No. 55, 8211-8215, Dec. 3, 2005.
Fichou, Y. and Ferec, C., The Potential of Oligonucleotides for Therapeutic Applications, Trends Biotech. 24(12): 563-570 (2006).
Cai, J., et al., Oxidative Damage and Protection of the RPE, Prog. Retinal Eye Res. 19(2): 205-221 (2000).
Barish, G.D., et al., PPARδ : A Dagger in the Heart of the Metabolic Syndrome, J. Clin. Invest. 116(3): 590-597 (2006).
Aigner, A., Delivery Systems for the Direct Application of siRNAs to Induce RNA Interference (RNAi) in vivo, J. Biomed. Biotech. 2006: 1-15 (2006).
Bishop-Bailey, "A role for PPARbeta/delta in Ocular Angiogenesis", PPAR Research, vol. 2008, p. 825970, Mar. 11, 2008.
Degenhardt et al, "Three Members of the Human Pyruvate Dehydrogenase Kinase Gene Family Are Direct Targets of the Peroxisome Proliferator-activated Receptor beta/delta", Journal of Molecular Biology, vol. 372, No. 2, 341-355, Aug. 21, 2007.
Zhang et al, "PPARbeta/delta activation inhibits angiotensin II-induced collagen type I expression in rat cardiac fibroblasts", Archives of Biochemistry and Biophysics, vol. 460, No. 1, 25-32, Mar. 28, 2007.

* cited by examiner

*Primary Examiner* — Kimberly Chong
(74) *Attorney, Agent, or Firm* — Joel B. German; Debra D. Condino

(57) ABSTRACT

The present invention provides novel agents, expression constructs, compositions and methods useful for treating an ocular disease associated with unwanted PPARδ activity through the modulation of PPARδ expression. The PPARδ interference RNA (iRNA) agents, expression constructs encoding such agents, and compositions comprising such agents or constructs are directed against RNA molecules encoding PPARδ. The methods comprise treating an ocular disease associated with unwanted PPARδ activity in a patient in need thereof by administering an effective amount of a pharmaceutical composition comprising a PPARδ iRNA agent or expression construct encoding such agent to the patient to reduce a symptom associated with unwanted PPARδ activity in the patient.

8 Claims, 3 Drawing Sheets

TREATING OCULAR DISEASES USING PEROXISOME PROLIFERATOR—ACTIVATED RECEPTOR DELTA ANTAGONISTS

This Application is a Divisional of co-pending application Ser. No. 12/524,217 filed on Jul. 23, 2009, which is hereby incorporated by reference in its entirety and which claims priority pursuant to 35 U.S.C. 119(e) to PCT/US08/52189, filed Jan. 28, 2008, which is hereby incorporated by reference in its entirety and which claims priority pursuant to 35 U.S.C. 119(e) to U.S. provisional application Ser. No. 60/887,178 filed on Jan. 30, 2007, which is hereby incorporated by reference in its entirety.

This patent application claims priority pursuant to 35 U.S.C. §119(e) to U.S. provisional patent application Ser. No. 60/887,178 filed on Jan. 30, 2007, which is hereby incorporated by reference in its entirety.

The retinal pigment epithelium (RPE) is a single layer of post-mitotic cells located between the photoreceptor layer containing rod and cone photoreceptors and the choriocapillaris, a vascular bed of fenestrated capillaries. Functioning both as a selective barrier to and a vegetative regulator of the overlying photoreceptor layer, the RPE is critical for the survival and activity of the photoreceptor layer, see, e.g., Olaf Strauss, *The Retinal Pigment Epithelium in Visual Function,* 85(3) Physiol. Rev. 845-881 (2005). Importantly, the RPE maintains photoreceptor excitability through the establishment of the retinal visual cycle. Retinal is constantly exchanged between photoreceptors and the RPE. Photoreceptors are unable to reisomerize all-trans-retinal, formed after photon absorption, back into 11-cis-retinal. To maintain the photoreceptor excitability, retinal is transported to the RPE reisomerized to 11-cis-retinal and transported back to photoreceptors. Additionally, the apical membrane of the RPE establishes voltage-dependent ion gradients that stabilize ion composition in the subretinal space (interphotoreceptor matrix), a feature that is also essential for the maintenance of photoreceptor excitability. The RPE also contributes to the maintenance of photoreceptor excitability and outer segment renewal by ingesting and degrading the spent tips of photoreceptor outer segments through phagocytosis, and the recycling essential substances such as retinal back to the photoreceptors to rebuild light-sensitive outer segments from the base of the photoreceptors. Furthermore, the RPE generates the blood-retina barrier and regulates the uptake of nutrients such as glucose, retinol (vitamin A), and fatty acids from the blood and delivers these nutrients to photoreceptors and the transport of ions, water, and metabolic waste from the subretinal space to the blood. In addition, the RPE maintains retinal homeostasis through the secretion of a variety of diffusible growth factors that preserve the structural integrity of choriocapillaris endothelium and photoreceptors. As a layer of pigmented cells containing melanin, the RPE absorbs the light energy focused by the lens on the retina and protects the outer retina from excessive high-energy light and light-generated oxygen reactive species. The secretory activity of the RPE also plays an important role in establishing the immune privilege of the eye by secreting immunosuppressive factors.

With these complex and different functions, the RPE is essential for visual function and the failure of any one of these functions can cause or intensify loss of visual function due to retinal degeneration. Indeed, a pathogenic role for an abnormal RPE function has been implicated in several ocular diseases, including, without limitation, wet and dry Age-Related Macular Degeneration (ARMD), Best's vitelliform macular degeneration, glaucoma, retinitis pigmentosa, diabetic retinopathy, macular edema and any degenerative disease of either the photoreceptors or the RPE, see, Strauss, supra, (2005). One causative factor underlying retinal damage due to an abnormal RPE function occurs when the accumulation of oxygen-derived metabolites cause oxidative damage to the cytoplasmic and nuclear elements of the cells comprising the RPE, see, e.g., Jiyang Cai, et al., *Oxidative Damage and Protection of the RPE,* 19(2) Prog. Retin. Eye Res. 205-221 (2000). For example, accumulation of oxidized lipids, such as low density lipoprotein (oxLDL), within the RPE disrupts the maintenance of photoreceptor excitability in the photoreceptor layer by impairing the ability of the RPE to process photoreceptor outer segments and results in RPE cell death due to the toxic nature of the oxidized lipid accumulation, see, e.g., George Hoppe et al., *Oxidative Low Density Lipoprotein-Induced Inhibition of Processing Photoreceptor Outer Segments by RPE,* 42(11) Invest. Ophthalmol. Vis. Sci. 2714-2720 (2001); I. R. Rodriguez et al., *Cytotoxicity of Oxidized Low-Density Lipoprotein in Cultured RPE Cells is Dependant on the Formation of 7-ketocholesterol,* 45(8) Invest. Ophthalmol. Vis. Sci. 2830-2837 (2004). Another causative factor underlying retinal degeneration due to an abnormal RPE function occurs in response to chronic inflammation brought on by, e.g., accumulation of cellular debris, pathologic angiogenesis, an immune response, or oxidative stress, see, e.g., Larry A. Donoso et al., *The Role of Inflammation in the Pathogenesis of Age-Related Macular Degeneration,* 51(2) Surv. Ophthalmol. 137-152 (2006).

Additionally, one of the most common causes of human blindness is abnormal intraocular cell proliferation that results in a loss of clarity of the visual axis or in a separation of the retina from the retinal pigment epithelium (retinal detachment). Since the RPE is critical in maintaining proper intraocular cellular proliferation, aberrant RPE function can result in abnormal intraocular cell proliferation. For example, over proliferation of the retinal cell layer, as observed in proliferative diabetic disease (PDR), retinopathy of prematurity (ROP) and proliferative vitreoretinopathy (PVR), can result in proliferative retinal detachment and permanent loss of vision. As another example, since transparency is an important characteristic of the eye, the uncontrolled division of endothelial cells leading to the formation of new blood vessels (neovascularization) can also ultimately compromise retinal function, see, e.g., A. Yoshida et al., *Intraocular Neovascularization,* Histol. Histopathol. 14(4): 1287-1294 (1999). This intraocular neovascularization, produces blood vessels which are fragile and likely to result in hemorrhage, thereby causing functional disorder of the eye and contribute to vision loss. Abnormal neovascularization is associated with such diseases as, e.g., ARMD, retinal-choroidal anastomosis (RCA), retinal angiomatous proliferation (RAP), retinal vein occlusion, neovascular glaucoma and proliferative retinopathies, like diabetic retinopathy. Lastly, intraocular cellular proliferation can result in cancers, such as, e.g., retinoblastoma and uveal melanoma. Thus, there is a need to provide agents, compositions and methods that can reduce the effects of an ocular disease associated with an abnormal RPE function.

Peroxisome Proliferator Activated Receptors (PPARs) are members of the nuclear hormone receptor superfamily, a large and diverse group of proteins that mediate ligand-dependent transcriptional activation and repression, see, e.g., Bhavani P. Kota et al, *An Overview on Biological Mechanisms of PPARs,* 51(2) Pharmacol. Res. 85-94 (2005). Numerous fatty acids and their derivatives, including a variety of eicosanoids and prostaglandins, have been shown to serve as PPAR ligands, see, e.g., Timothy M. Willson et al., *The*

*PPARs: From Orphan Receptors to Drug Discovery*, 43(4) J. Med. Chem. 527-550 (2000). On activation by endogenously secreted ligand, PPARs initiate transcription of an array of genes that are involved in energy homeostasis, including, without limitation, plasma lipid transport and fatty acid catabolism, endothelial cell proliferation, angiogenesis, regulation of insulin sensitivity and blood glucose levels, inflammatory response, macrophage differentiation, and adipocyte differentiation. Thus, PPARs appear to play a central role in modulating metabolism by sensing the levels of various nutrients.

The PPAR subfamily currently comprises three proteins, PPARα, PPARγ and PPARδ (also known as PPARβ or NUC1), that are encoded by separate genes which appear to be ubiquitously expressed throughout the body. PPARs regulate target gene expression by binding to specific peroxisome proliferator response elements (PPREs) in enhancer sites of regulated genes. PPARs possess a modular structure composed of functional domains that include a DNA binding domain (DBD) and a ligand binding domain (LBD). The DBD specifically binds PPREs in the regulatory region of PPAR-responsive genes. The DBD, located in the C-terminal half of the receptor, contains the ligand-dependent activation domain, AF-2. Each receptor binds to its PPRE as a heterodimer with a retinoid X receptor (RXR). Upon ligand binding, the conformation of a PPAR is altered and stabilized such that a binding cleft, made up in part of the AF-2 domain, is created and recruitment of transcriptional coactivators occurs. Coactivators augment the ability of nuclear receptors to initiate the transcription process. The result of the ligand-induced PPAR-coactivator interaction at the PPRE is an increase in gene transcription. Downregulation of gene expression by PPARs appears to occur through indirect mechanisms.

The ability of PPARs to regulate lipid metabolism and inflammatory responses prompted us to examine the effects of down regulating PPAR expression on survival of RPE cells undergoing oxidative stress. Treatment of RPE cells in the presence of an agent that generates intracellular reactive oxygen species followed by withdrawal leads to apoptosis of the cells within 24 hours. Surprisingly, down regulation of PPARδ expression using RNA interference (RNAi) in similarly treated cells resulted in a dramatic enhancement of RPE cell survival. These findings indicate that the reduction of PPARδ activity in cells comprising the RPE has a protective effect against apoptotsis induced by oxidative stress. Thus, the reduction or elimination of PPARδ activity in RPE cells would have utility in the treatment of ocular diseases characterized by oxidative stress facilitated by unwanted PPARδ activity.

The present invention provides novel agents, expression constructs, compositions and methods useful for treating an ocular disease associated with unwanted PPARδ activity through the modulation of PPARδ expression. The PPARδ interference RNA (iRNA) agents, expression constructs encoding such agents, and compositions comprising such agents or constructs are directed against RNA molecules encoding PPARδ. The methods comprise treating an ocular disease associated with unwanted PPARδ activity in a patient in need thereof by administering an effective amount of a pharmaceutical composition comprising a PPARδ iRNA agent or expression construct encoding such agent to the patient to reduce a symptom associated with unwanted PPARδ activity in the patient.

DETAILED DESCRIPTION

Figure 1:
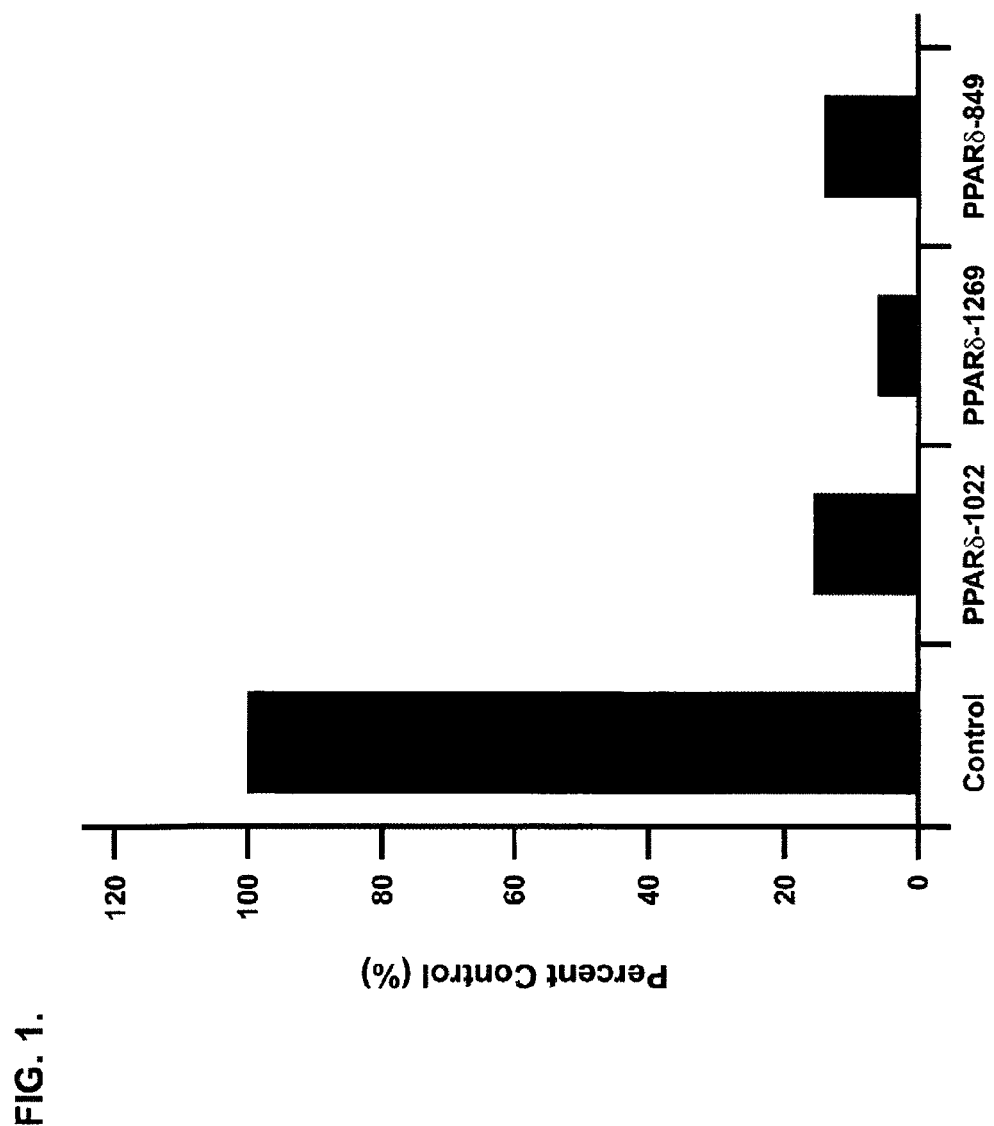
FIG. 1 shows inhibition of PPARδ expression by specific PPARδ iRNA agents. PPARδ iRNA agents designed to inhibit PPARδ expression were transfected into ARPE-19 cells at a final concentration of 25 nM. Cells were harvested 72 hours and 9 days post-transfection and RNA isolated. Quantitative PCR was conducted using GAPDH to normalize expression levels. RNA levels are expressed as percent of PPARδ expression in control samples (untransfected cells). All PPARδ iRNA agents used demonstrated a significant reduction in PPARδ RNA expression.

The present invention discloses agents, compositions and methods useful for treating an ocular disease associated with an unwanted PPARδ activity. This is accomplished by using PPARδ iRNA molecules to ultimately reduce the amount of PPARδ synthesized by cells comprising the RPE. As disclosed herein, inhibition of PPARδ activity provides a protective effect from apoptosis and cell death induced by oxidative stress. Based on these results, the present invention provides PPARδ iRNA agents, compositions and methods that can be used in treating an ocular disease associated with an unwanted PPARδ activity.

Thus, an aspect of the present invention provides a PPARδ iRNA agent capable of reducing the level of PPARδ within a cell. The PPARδ iRNA agents disclosed in the present specification comprise a duplex region, where the duplex region comprises a sense sequence and an anti-sense sequence. The sense sequence comprises a nucleotide sequence that is identical to or substantially identical to a PPARδ target sequence. The anti-sense sequence comprises a nucleotide sequence complementary to or sufficiently complementary to a PPARδ target sequence. The PPARδ target sequence can include a PPARδ coding sequence, a PPARδ regulatory sequence such as the 5'-UTR and 3'-UTR, or a PPARδ sequence that comprises both a coding sequence and a regulatory sequence. The iRNA agents can be chemically synthesized or expressed from a vector or enzymatically synthesized. The PPARδ iRNA agents can be unmodified or chemically-modified nucleic acid molecules. The use of a chemically-modified iRNA agent can improve one or more properties of an iRNA agent through increased resistance to degradation, increased specificity to target moieties, improved cellular uptake, and the like.

Other aspects of the present invention provide an expression construct comprising an expression vector operably-linked to a PPARδ iRNA agent. It is envisioned that any PPARδ iRNA agent disclosed in the present specification can be used.

Other aspects of the present invention provide a composition comprising a PPARδ iRNA agent. It is envisioned that any PPARδ iRNA agent disclosed in the present specification can be used. A composition comprising a PPARδ iRNA agent can be a pharmaceutical composition. Such a pharmaceutical composition can comprise, in addition to a PPARδ iRNA agent, a pharmaceutical carrier, a pharmaceutical component, or both.

Other aspects of the present invention provide a method of treating an ocular disease associated with an unwanted PPARδ activity in a patient in need thereof, the method comprising the step of administering a pharmaceutical composition comprising a PPARδ iRNA agent under conditions suitable to reduce expression of PPARδ in the patient, thereby reducing a symptom associated with the ocular disease. It is envisioned that any pharmaceutical composition comprising a PPARδ iRNA agent disclosed in the present specification can be used. Additionally, it is envisioned that any ocular disease associated with an unwanted PPARδ activity can be treating using the disclosed method, including, without limitation, wet and dry Age-Related Macular Degeneration (ARMD), Best's vitelliform macular degeneration, glaucoma, retinitis pigmentosa, diabetic retinopathy, macular edema and any degenerative disease of either the photoreceptors or the RPE.

Conserved in both plants and animals, RNA interference (RNAi) is a well-conserved, post-translational mechanism of gene silencing whereby expression of a specific protein can be reduced or eliminated. Using small non-coding double-stranded RNAs called microRNAs (msRNAs), RNA-interference pathway regulates expression of important genes involved in cell death, differentiation, and development, as well as, protects the genome from invading genetic elements, encoded by transposons and viruses. Recently, RNAi has emerged as a potential way to treat human disease. RNA-interference agents, such as, e.g., small interfering RNA (siRNA) and small hairpin RNA (shRNA), are exogenous double-stranded nucleic acid sequences expressly designed to have homology to sections of the target protein's mRNA, and when present in the cell trigger hydrolysis of the mRNA through the endogenous RNA-interference pathway.

Whether triggered by an endogenous or exogenous double-stranded RNA molecule, RNAi relies on a multi-step pathway, see, e.g., Thomas Rohl and Jens Kurreck, *RNA Interference in Pain Research*, 99(2) J. Neurochem. 371-380 (2006); George L. Sen and Helen M. Blau, *A Brief History of RNAi: The Silence of the Genes* 20(9) FASEB J. 1293-1299 (2006). Initially, long double-stranded RNA molecules present in the cell, by either cellular uptake or gene expression, appears to be incorporated into a nuclease-containing multi-protein complex termed the RNA-induced Loading Complex (RLC) that comprises a ribonuclease III-type protein called Dicer. Formation of the RLC allows the endonuclease activity of Dicer to cleave the double-stranded RNA molecules into short 21-23 nucleotide fragments called small inhibitory RNAs (siRNAs). siRNAs comprise a 2-3 nucleotide overhang at the 3'-end, as well as a 5'-phosphate and a 3'-hydroxyl group. Alternatively, siRNAs can be directly introduced into the RLC, thereby bypassing the Dicer processing step. The RLC further recruits the endonuclease Argonaute 2 (Argo 2), thereby forming the RNA-induced silencing complex (RISC). Upon recruitment, Argo 2 cleaves one of the two siRNA strands, referred to as the passenger or anti-guide strand, which is released from the RISC. The other siRNA strand, referred to as the guide strand, remains within the RISC and serves as a binding template for its complementary target mRNA. Upon target mRNA binding, the endonucleolytic activity of Argo 2 cleaves the target mRNA within the template sequence region and the resulting target mRNA cleavage products are released into the cytoplasm where they are rapidly degradation due to their unprotected ends. After release of the cleaved target mRNA, the RISC can initiate multiple cycles of target mRNA degradation, with the entire process resulting in a net reduction in the levels of the specific target mRNA and hence decreased synthesis of the encoding protein.

Aspects of the present invention provide, in part, a PPARδ iRNA agent. As used herein, the term "PPARδ iRNA agent" means any small unmodified or modified nucleic acid molecule comprising a duplex region capable of mediating RNAi against a PPARδ nucleic acid molecule. As such, a PPARδ iRNA agent, or a cleavage product thereof, includes a duplex region of sufficient identity and nucleotide length to the target PPARδ gene, that the PPARδ iRNA agent, or a cleavage product thereof, can mediate the down regulation of the target PPARδ gene expression. It is envisioned that the duplex region of a PPARδ iRNA agent can be formed from a single stranded molecule, such as, e.g., a miRNA or shRNA, or can formed from more than one independent strand, e.g., siRNA. As discussed above, double-stranded RNA molecules that are longer than about 23 nucleotides are cleaved by Dicer during assembly of the RISC, whereas double-stranded RNA molecules less than about 23 nucleotides associate with the RLC without any Dicer-mediated processing. Thus, a PPARδ iRNA agent of the present specification includes both molecules that are long enough to be cleaved by Dicer before assembly into a RISC as well as molecules that are sufficiently short that they bypass Dicer-mediate cleavage and incorporate into the RISC. In mammals, double-stranded RNA molecules that are longer than about 30 nucleotides induce an interferon response that ultimately can shut down protein syntheses in the affected cell. On the other hand, double-stranded RNA molecules that are less than about 30 nucleotides do not illicit an interferon response. Thus, a PPARδ iRNA agent of the present specification includes both molecules that are long enough to trigger the interferon response as well as molecules that are sufficiently short that they do not trigger the interferon response. Thus, it is envisioned that any iRNA agent useful for modulating the expression of PPARδ activity by RNAi can be used, including, without limitation, single-stranded RNA, double-stranded RNA, siRNA, miRNA, and shRNA.

As used herein, the term "single strand PPARδ iRNA agent" means a PPARδ iRNA agent which is made up of a single molecule, such as, e.g., miRNA and shRNA. A single strand PPARδ iRNA agent comprises a sense sequence and an anti-sense sequence with regard to the PPARδ target sequence. A single strand PPARδ iRNA agent should be of sufficient length that upon formation of the duplex region it can assemble into and direct RISC-mediate selective cleavage of a target PPARδ sequence.

As used herein, the term "selective" or "selectively" means having a highly preferred activity or effect. As used herein, the term "selective cleavage" or "selectively cleaved" in reference to a RISC comprising a PPARδ iRNA agent, or fragment thereof, means a RISC that can cleave a target PPARδ sequence under physiological conditions, or in vitro conditions substantially approximating physiological conditions, to a statistically significantly greater degree relative to other, non-target or off-target sequences. Thus, with reference to a RISC comprising a PPARδ iRNA agent, or fragment thereof, there is a discriminatory cleavage of a target PPARδ sequence.

Thus, in an embodiment, single strand PPARδ iRNA agent comprises a length sufficient to form a duplex region capable of mediating the down regulation of the target PPARδ gene expression by RNAi. In aspects of this embodiment, a single strand PPARδ iRNA agent can have a length of, e.g., at least 25 nucleotides, at least 30 nucleotides, at least 35 nucleotides, at least 40 nucleotides, at least 50 nucleotides, at least 60 nucleotides, at least 70 nucleotides, at least 80 nucleotides, at least 90 nucleotides, or at least 100 nucleotides. In other aspects of this embodiment, a single strand PPARδ iRNA agent can have a length of, e.g., at least 100 nucleotides, at least 150 nucleotides or at least 200 nucleotides. In other aspects of this embodiment, a single strand PPARδ iRNA agent can have a length of, e.g., at most 30 nucleotides, at most at least 30 nucleotides, at most 35 nucleotides, at most 40 nucleotides, at most 50 nucleotides, at most 60 nucleotides, at most 70 nucleotides, at most 80 nucleotides, at most 90 nucleotides, or at most 100 nucleotides. In other aspects of this embodiment, a single strand PPARδ iRNA agent can have a length of, e.g., at most 100 nucleotides, at most 150 nucleotides or at most 200 nucleotides.

Single stranded regions of a PPARδ iRNA agent can be modified or include a nucleoside surrogate, e.g., the unpaired region or regions flanking a duplex region can have modifications or nucleoside surrogates. Such modification can stabilize the 3'-end, the 5'-end, or both the 3'- and 5'-ends of a PPARδ iRNA agent. Modifications can include C3 (or C6, C7, C12)amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. A nucleoside surrogate can stabilize a PPARδ iRNA agent by protecting against exonucleases, or favoring the PPARδ iRNA agent to enter into RNAi-induced silencing complex (RISC).

As used herein, the term "double stranded PPARδ iRNA agent" as used herein, is a PPARδ iRNA agent which includes at least two nucleic acid strands in which inter-chain hybridization can form a duplex region. A double stranded PPARδ iRNA agent comprises a sense sequence and an anti-sense sequence with regard to the PPARδ target sequence. A double strand PPARδ iRNA agent should be of sufficient length that upon formation of the duplex region it can assemble into and direct RISC-mediate selective cleavage of a target PPARδ sequence.

Thus, in an embodiment, double strand PPARδ iRNA agent comprises a length sufficient to form a duplex region capable of mediating the down regulation of the target PPARδ gene expression by RNAi. In aspects of this embodiment, a double strand PPARδ iRNA agent can have a length of, e.g., at least 15 nucleotides, at least 20 nucleotides, at least 25 nucleotides, at least 30 nucleotides, at least 35 nucleotides, at least 40 nucleotides, at least 50 nucleotides, at least 60 nucleotides, at least 70 nucleotides, at least 80 nucleotides, at least 90 nucleotides, or at least 100 nucleotides. In other aspects of this embodiment, a single strand PPARδ iRNA agent can have a length of, e.g., at least 100 nucleotides, at least 150 nucleotides or at least 200 nucleotides. In other aspects of this embodiment, a single strand PPARδ iRNA agent can have a length of, e.g., at most 15 nucleotides, at most 20 nucleotides, at most 25 nucleotides, at most at least 30 nucleotides, at most 35 nucleotides, at most 40 nucleotides, at most 50 nucleotides, at most 60 nucleotides, at most 70 nucleotides, at most 80 nucleotides, at most 90 nucleotides, or at most 100 nucleotides. In other aspects of this embodiment, a single strand PPARδ iRNA agent can have a length of, e.g., at most 100 nucleotides, at most 150 nucleotides or at most 200 nucleotides.

Aspects of the present invention provide, in part, a duplex region. As used herein, the term "duplex region" means a double stranded nucleic acid sequence comprising a sense sequence and an anti-sense sequence. The sense sequence is complementary to the anti-sense sequence, and as such, the duplex region can be formed, e.g., by intra-strand pairing of the sense and anti-sense sequences or by inter-strand pairing of the sense and anti-sense sequences. As a non-limiting example, a single strand PPARδ iRNA agent comprises a duplex region that is formed by intra-strand pairing of the sense and anti-sense sequences, resulting in the formation of a hairpin or pan-handle structure. As another non-limiting example, a double strand PPARδ iRNA agent comprises a duplex region that is formed by inter-strand pairing of the sense and anti-sense sequences. The sense sequence need only be sufficiently complementary with the anti-sense sequence to maintain the overall duplex region formed by, e.g., intra-strand pairing of a single-stranded PPARδ iRNA agent or inter-strand pairing of a double-stranded PPARδ iRNA agent. A PPARδ iRNA agent can have non-canonical pairings between the sense and anti-sense sequences of the duplex region, a ZXY structure, or be complexed with an amphipathic moiety, see, e.g., Muthiah Manoharan et al., Modified iRNA Agents, U.S. Patent Publication 2005/0107325 (May 19, 2005); and Muthiah Manoharan and Kallanthottathil G. Rajeev, Modified iRNA Agents, U.S. Patent Publication 2005/0164235 (Jul. 25, 2005); and Muthiah Manoharan and Kallanthottathil G. Rajeev, iRNA Agents with Biocleavable Tethers, U.S. Patent Publication 2005/0256069 (Nov. 17, 2005), each of which is herein incorporated by reference in its entirety.

In an embodiment, single strand PPARδ iRNA agent comprises a duplex region. In aspects of this embodiment, a single strand PPARδ iRNA agent comprises a duplex region having a length of, e.g., at least 14 nucleotide pairs, at least 15 nucleotide pairs, at least 16 nucleotide pairs, at least 17 nucleotide pairs, at least 18 nucleotide pairs, at least 19 nucleotide pairs, at least 20 nucleotide pairs, at least 21 nucleotide pairs, at least 22 nucleotide pairs, at least 23 nucleotide pairs, at least 24 nucleotide pairs, at least 25 nucleotide pairs or at least 30 nucleotide pairs. In other aspects of this embodiment, a single strand PPARδ iRNA agent comprises a duplex region having a length of, e.g., at least 50 nucleotide pairs, at least 75 nucleotide pairs or at least 100 nucleotide pairs. In other aspects of this embodiment, a single strand PPARδ iRNA agent capable comprising a duplex region having a length of, e.g., at most 14 nucleotide pairs, at most 15 nucleotide pairs, at most 16 nucleotide pairs, at most 17 nucleotide pairs, at most 18 nucleotide pairs, at most 19 nucleotide pairs, at most 20 nucleotide pairs, at most 21 nucleotide pairs, at most 22 nucleotide pairs, at most 23 nucleotide pairs, at most 24 nucleotide pairs, at most 25 nucleotide pairs or at most 30 nucleotide pairs. In other aspects of this embodiment, a single strand PPARδ iRNA agent comprises a duplex region having a length of, e.g., at most 50 nucleotide pairs, at most 75 nucleotide pairs or at most 100 nucleotide pairs. In other aspects of this embodiment, a single strand PPARδ iRNA agent comprises a duplex region having a length of, e.g., about 15 to about 30 nucleotides pairs, about 17 to about 25 nucleotides pairs, about 19 to about 23 nucleotides pairs, and about 19 to about 21 nucleotides pairs. In other aspects of this embodiment, a single strand PPARδ iRNA agent comprises a duplex region having a length of, e.g., 18, 19, 20, 21, 22, or 23 nucleotides pairs.

In another embodiment, double strand PPARδ iRNA agent comprises a duplex region. In aspects of this embodiment, a double strand PPARδ iRNA agent comprises a duplex region having a length of, e.g., at least 14 nucleotide pairs, at least 15 nucleotide pairs, at least 16 nucleotide pairs, at least 17 nucleotide pairs, at least 18 nucleotide pairs, at least 19 nucleotide pairs, at least 20 nucleotide pairs, at least 21 nucleotide pairs, at least 22 nucleotide pairs, at least 23 nucleotide pairs, at least 24 nucleotide pairs, at least 25 nucleotide pairs or at least 30 nucleotide pairs. In other aspects of this embodiment, a double strand PPARδ iRNA agent comprises a duplex region having a length of, e.g., at least 50 nucleotide pairs, at least 75 nucleotide pairs or at least 100 nucleotide pairs. In other aspects of this embodiment, a double strand PPARδ iRNA agent capable comprising a duplex region having a length of, e.g., at most 14 nucleotide pairs, at most 15 nucleotide pairs, at most 16 nucleotide pairs, at most 17 nucleotide pairs, at most 18 nucleotide pairs, at most 19 nucleotide pairs, at most 20 nucleotide pairs, at most 21 nucleotide pairs, at most 22 nucleotide pairs, at most 23 nucleotide pairs, at most 24 nucleotide pairs, at most 25 nucleotide pairs or at most 30 nucleotide pairs. In other aspects of this embodiment, a double strand PPARδ iRNA agent comprises a duplex region having a length of, e.g., at most 50 nucleotide pairs, at most 75 nucleotide pairs or at most 100 nucleotide pairs. In other aspects of this embodiment, a double strand PPARδ iRNA agent comprises a duplex region having a length of, e.g., about 15 to about 30 nucleotides pairs, about 17 to about 25 nucleotides pairs, about 19 to about 23 nucleotides pairs, and about 19 to about 21 nucleotides pairs. In other aspects of this embodiment, a double strand PPARδ iRNA agent comprises a duplex region having a length of, e.g., 18, 19, 20, 21, 22, or 23 nucleotides pairs.

A duplex region, formed by either a single-stranded or double-stranded of a PPARδ iRNA agent, can have a single strand overhang or terminal unpaired region at one or both ends of the molecule. Thus, a duplex region can include, e.g., one or two 5'-end overhangs, one or two 3'-end overhangs, or a combination thereof. As used herein, the term "3'-end overhang" means at least one unpaired nucleotide extending from the 3'-end of a sense sequence, an anti-sense sequence, or both a sense sequence and an anti-sense sequence of the duplex region. As used herein, the term "5'-end overhang" means at least one unpaired nucleotide extending from the 5'-end of a sense sequence, an anti-sense sequence, or both a sense sequence and an anti-sense sequence of the duplex region. An overhang can include ribonucleotides or deoxyribonucleotides or modified ribonucleotides or modified deoxyribonucleotides. Formation of an overhang can result from one sequence being longer than the other, or the result of two sequences of the same length being staggered.

In an embodiment, a duplex region of a PPARδ iRNA agent comprises an overhang. In an aspect of this embodiment, the overhang is at the 3'-end of the duplex region. In another aspect of this embodiment, the 3'-end overhang occurs on the anti-sense sequence of the duplex region. In another aspect of this embodiment, the 3'-end overhang occurs on the sense sequence of the duplex region. In another aspect of this embodiment, the 3'-end overhang occurs on both the sense sequence and the anti-sense sequence of the duplex region. In aspects of this embodiment, the 3'-end overhang is, e.g., at least one nucleotide in length, at least two nucleotides in length, at least three nucleotides in length, at least four nucleotides in length, at least five nucleotides in length, or at least six nucleotides in length. In other aspects of this embodiment, the 3'-end overhang is, e.g., at most one nucleotide in length, at most two nucleotides in length, at most three nucleotides in length, at most four nucleotides in length, at most five nucleotides in length, or at most six nucleotides in length. In aspects of this embodiment, the 3'-end overhang can have, e.g., a length of 1 to 5 nucleotides, a length of 1 to 4 nucleotides, a length of 2 to 4 nucleotides, a length of 1 to 3 nucleotides, or a length of 1 to 2 nucleotides. Preferred 3'-end overhangs are 2 or 3 nucleotides in length. In another aspect of this embodiment, the 3'-end overhang is on both sequences of the PPARδ iRNA agent and is two nucleotides in length. In another aspect of this embodiment, the 3'-end overhang is on both sequences of the iRNA agent and the 3'-end overhangs include two thymidylic acid residues ("TT").

In another aspect of this embodiment, the overhang is at the 5'-end of the duplex region. In another aspect of this embodiment, the 5'-end overhang occurs on the anti-sense sequence of the duplex region. In another aspect of this embodiment, the 5'-end overhang occurs on the sense sequence of the duplex region. In another aspect of this embodiment, the 5'-end overhang occurs on both the sense sequence and the anti-sense sequence of the duplex region. In aspects of this embodiment, the 5-end overhang is, e.g., at least one nucleotide in length, at least two nucleotides in length, at least three nucleotides in length, at least four nucleotides in length, at least five nucleotides in length, or at least six nucleotides in length. In other aspects of this embodiment, the 5'-end overhang is, e.g., at most one nucleotide in length, at most two nucleotides in length, at most three nucleotides in length, at most four nucleotides in length, at most five nucleotides in length, or at most six nucleotides in length. In aspects of this embodiment, the 5'-end overhang can have, e.g., a length of 1 to 5 nucleotides, a length of 1 to 4 nucleotides, a length of 2 to 4 nucleotides, a length of 1 to 3 nucleotides, or a length of 1 to 2 nucleotides. Preferred 5'-end overhangs are 2 or 3 nucleotides in length. A 5'-end overhang is preferably phosphorylated.

Aspects of the present invention provide, in part, a sense sequence. As used herein, the term "sense sequence" means a nucleic acid sequence comprising a length of at least 14 nucleotides that are identical or substantially identical to a PPARδ target sequence. As used herein, the term "substantially identical" means that the mismatch between the sense sequence and the PPARδ target sequence is less than 30% with the proviso that the iRNA agent comprising the substantially identical sense sequence is capable of reducing the level of PPARδ within a cell and with the proviso that the sense strand is not identical to SEQ ID NO: 73 or SEQ ID NO: 74. While a sense sequence that is complementary to an anti-sense sequence is often desired, substantial complementarity of an anti-sense sequence with respect to the sense sequence is envisioned. Mismatches are most tolerated in the terminal regions of a sense sequences and if present are preferably in a terminal region or regions.

In aspects of this embodiment, a PPARδ iRNA agent capable of reducing the level of PPARδ expression within a cell by RNAi comprises a sense sequence having a nucleotide length of, e.g. 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides. In other aspects of this embodiment, the sense sequence has a nucleotide length of e.g., at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, or at least 30 nucleotides. In other aspects of this embodiment, the sense sequence has a nucleotide length of e.g., at least 50 nucleotides, at least 75 nucleotides or at least 100 nucleotides. Preferred ranges of a sense sequence are 15 to 30 nucleotides in length, 17 to 25 nucleotides in length, 19 to 23 nucleotides in length, and 19 to 21 nucleotides in length.

In an embodiment, the sense sequence is identical to a PPARδ target sequence. In aspects of this embodiment, the sense sequence identical to a PPARδ target sequence is e.g., 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, or 30 nucleotides in length. In other aspects of this embodiment, the sense sequence identical to a PPARδ target sequence is e.g., at least 17 nucleotides in length, at least 18 nucleotides in length, at least 19 nucleotides in length, at least 20 nucleotides in length, at least 21 nucleotides in length, at least 22 nucleotides in length, at least 23 nucleotides in length, at least 24 nucleotides in length, at least 25 nucleotides in length, at least 26 nucleotides in length, at least 27 nucleotides in length, at least 28 nucleotides in length, at least 29 nucleotides in length, or at least 30 nucleotides in length.

In another embodiment, the sense sequence is substantially identical to a PPARδ target sequence. In aspects of this embodiment, the sense sequence is 17, 18, 19, 20, 21, 22, 23, 24, or 25 nucleotides in length and has, e.g., at least 70% identical to a PPARδ target sequence, at least 80% identical to a PPARδ target sequence, at least 90% identical to a PPARδ target sequence, at least 95% identical to a PPARδ target sequence, or at least 99% identical to a PPARδ target sequence. In other aspects of this embodiment, the sense sequence substantially identical to a PPARδ target sequence comprises e.g., at least 50 nucleotides, at least 75 nucleotides or at least 100 nucleotides. In other aspects of this embodiment, the sense sequence differs from a PPARδ target sequence by, e.g., no more than one nucleotide, no more than two nucleotides, no more than three nucleotides, no more than four nucleotides, no more than five nucleotides, no more than six nucleotides, no more than seven nucleotides, no more than eight nucleotides, no more than nine nucleotides, or no more than ten nucleotides. In other aspects of this embodiment, mismatches in a sense sequence occur within, e.g., 1, 2, 3, 4, 5, or 6 nucleotides of the 3'-end, 5'-end, or both the 3'- and 5'-end of the sense sequence.

Aspects of the present invention provide, in part, an anti-sense sequence. As used herein, the term "anti-sense sequence" means a nucleic acid sequence comprising a length at least 14 nucleotides that is complementary to or substantially complementary to a sense sequence or a PPARδ target sequence. As used herein, the term "complementary" means that there is no mismatch between the anti-sense sequence and the sense sequence or the PPARδ target sequence. As used herein, the term "substantially complementary" means that the mismatch between the anti-sense sequence and the sense sequence or the PPARδ target sequence is less than 30% with the proviso that the iRNA agent comprising the substantially complementary anti-sense sequence is capable of reducing the level of PPARδ within a cell and with the proviso that the anti-sense strand is not complementary to SEQ ID NO: 73 or SEQ ID NO: 74. While complementary of the an anti-sense sequence with respect to the target PPARδ molecule is often desired, substantial complementarity of an anti-sense sequence with respect to the target PPARδ molecule is envisioned. Thus, it is not necessary that there be perfect complementarity between an anti-sense sequence and the PPARδ target sequence, but the correspondence must be sufficient to enable the PPARδ iRNA agent, or a cleavage product thereof, to direct sequence specific silencing of the target PPARδ molecule by RNAi. Mismatches are most tolerated in the terminal regions of an anti-sense sequences and if present are preferably in a terminal region or regions. Thus, it is envisioned that any PPARδ anti-sense sequence capable of reducing the level of PPARδ within a cell by RNAi can be used. Additionally, a PPARδ anti-sense sequence does not selectively hybridize to an off-target sequence. As used herein, the term "off-target" means a nucleic acid sequence other than a PPARδ target sequence. A PPARδ iRNA agent comprises a region which is at least partially, and in some embodiments fully, complementary to the target PPARδ RNA.

In aspects of this embodiment, a PPARδ iRNA agent capable of reducing the level of PPARδ within a cell by RNAi comprises an anti-sense sequence having a nucleotide length of, e.g. 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides. In other aspects of this embodiment, the anti-sense sequence has a nucleotide length of e.g., at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, or at least 30 nucleotides. In other aspects of this embodiment, the anti-sense sequence has a nucleotide length of e.g., at least 50 nucleotides, at least 75 nucleotides or at least 100 nucleotides. Preferred ranges of an anti-sense sequence are 15 to 30 nucleotides in length, 17 to 25 nucleotides in length, 19 to 23 nucleotides in length, and 19 to 21 nucleotides in length.

In an embodiment, the anti-sense sequence is complementary to a sense sequence. In aspects of this embodiment, the anti-sense sequence complementary to a sense sequence comprises, e.g., 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, or 30 nucleotides in length. In other aspects of this embodiment, the anti-sense sequence complementary to a sense sequence is e.g., at least 17 nucleotides in length, at least 18 nucleotides in length, at least 19 nucleotides in length, at least 20 nucleotides in length, at least 21 nucleotides in length, at least 22 nucleotides in length, at least 23 nucleotides in length, at least 24 nucleotides in length, at least 25 nucleotides in length, at least 26 nucleotides in length, at least 27 nucleotides in length, at least 28 nucleotides in length, at least 29 nucleotides in length, or at least 30 nucleotides in length. In other aspects of this embodiment, the anti-sense sequence complementary to a sense sequence is e.g., at least 50 nucleotides in length, at least 75 nucleotides in length or at least 100 nucleotides in length.

In another embodiment, the anti-sense sequence is substantially complementary to a sense sequence. In aspects of this embodiment, the anti-sense sequence substantially complementary to a sense sequence comprises, e.g., 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, or 30 nucleotides in length. In other aspects of this embodiment, the anti-sense sequence substantially complementary to a sense sequence comprises e.g., at least 50 nucleotides, at least 75 nucleotides or at least 100 nucleotides. In other aspects of this embodiment, the anti-sense sequence comprises 17, 18, 19, 20, 21, 22, 23, 24, or 25 nucleotides in length and has, e.g., at least 70% complementary to a sense sequence, at least 80% complementary to a sense sequence, at least 90% complementary to a sense sequence, at least 95% complementary to a sense sequence, or at least 99% complementary to a sense sequence. In other aspects of this embodiment, the anti-sense sequence differs from a sense sequence by, e.g., no more than one nucleotide, no more than two nucleotides, no more than three nucleotides, no more than four nucleotides, no more than five nucleotides, no more than six nucleotides, no more than seven nucleotides, no more than eight nucleotides, no more than nine nucleotides, or no more than ten nucleotides. In other aspects of this embodiment, mismatches in an anti-sense sequence occur within, e.g., 1, 2, 3, 4, 5, or 6 nucleotides of the 3'-end, 5'-end, or both the 3'- and 5'-end of the anti-sense sequence.

In yet another embodiment, the anti-sense sequence is complementary to a PPARδ target sequence. In aspects of this embodiment, the anti-sense sequence complementary to a PPARδ target sequence comprises, e.g., 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, or 30 nucleotides in length. In other aspects of this embodiment, the anti-sense sequence complementary to a PPARδ target sequence is e.g., at least 17 nucleotides in length, at least 18 nucleotides in length, at least 19 nucleotides in length, at least 20 nucleotides in length, at least 21 nucleotides in length, at least 22 nucleotides in length, at least 23 nucleotides in length, at least 24 nucleotides in length, at least 25 nucleotides in length, at least 26 nucleotides in length, at least 27 nucleotides in length, at least 28 nucleotides in length, at least 29 nucleotides in length, or at least 30 nucleotides in length. In other aspects of this embodiment, the anti-sense sequence complementary to a PPARδ target sequence is e.g., at least 50 nucleotides in length, at least 75 nucleotides in length or at least 100 nucleotides in length.

In still another embodiment, the anti-sense sequence is substantially complementary to a PPARδ target sequence. In aspects of this embodiment, the anti-sense sequence substantially complementary to a PPARδ target sequence comprises, e.g., 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, or 30 nucleotides in length. In other aspects of this embodiment, the anti-sense sequence substantially complementary to a PPARδ target sequence comprises e.g., at least 50 nucleotides, at least 75 nucleotides or at least 100 nucleotides. In other aspects of this embodiment, the anti-sense sequence comprises 17, 18, 19, 20, 21, 22, 23, 24, or 25 nucleotides in length and has, e.g., at least 70% complementary to a PPARδ target sequence, at least 80% complementary to a PPARδ target sequence, at least 90% complementary to a PPARδ target sequence, at least 95% complementary to a PPARδ target sequence, or at least 99% complementary to a PPARδ target sequence. In other aspects of this embodiment, the anti-sense sequence differs from a PPARδ target sequence by, e.g., no more than one nucleotide, no more than two nucleotides, no more than three nucleotides, no more than four nucleotides, no more than five nucleotides, no more than six nucleotides, no more than seven nucleotides, no more than eight nucleotides, no more than nine nucleotides, or no more than ten nucleotides. In other aspects of this embodiment, mismatches in an anti-sense sequence occur within, e.g., 1, 2, 3, 4, 5, or 6 nucleotides of the 3'-end, 5'-end, or both the 3'- and 5'-end of the anti-sense sequence.

Aspects of the present invention provide, in part, a PPARδ target sequence. As used herein, the term "PPARδ target sequence" means a nucleic acid sequence comprising a length of at least 14 nucleotides of a PPARδ nucleic acid molecule, such as, e.g., a human PPARδ DNA or RNA molecule, or a non-human PPARδ DNA or RNA molecule like monkey, mouse and rat, with the proviso that the PPARδ target sequence is not SEQ ID NO: 73 or SEQ ID NO: 74. Exemplary PPARδ nucleic acid molecules include SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. Exemplary PPARδ target sequences are listed in Table 1.

TABLE 1

Exemplary PPARδ Target Sequences

| Name | PPARδ Region | Target Sequence | SEQ ID NO: |
|---|---|---|---|
| 114 | 5' UTR | 5'-AGCCGGGACAGUGUUGUACAGUGUU-3' | 15 |
| 115 | 5' UTR | 5'-GCCGGGACAGUGUUGUACAGUGUUU-3' | 16 |
| 142 | 5' UTR | 5'-GGCAUGCACGUGAUACUCA-3' | 17 |
| 142 | 5' UTR | 5'-GGCAUGCACGUGAUACUCACACAGU-3' | 18 |
| 143 | 5' UTR | 5'-GCAUGCACGUGAUACUCAC-3' | 19 |
| 143 | 5' UTR | 5'-GCAUGCACGUGAUACUCACACAGUG-3' | 20 |
| 147 | 5' UTR | 5'-GCACGUGAUACUCACACAG-3' | 21 |
| 147 | 5' UTR | 5'-GCACGUGAUACUCACACAGUGGCUU-3' | 22 |
| 148 | 5' UTR | 5'-CACGUGAUACUCACACAGU-3' | 23 |
| 149 | 5' UTR | 5'-ACGUGAUACUCACACAGUG-3' | 24 |
| 149 | 5' UTR | 5'-ACGUGAUACUCACACAGUGGCUUCU-3' | 25 |
| 152 | 5' UTR | 5'-UGAUACUCACACAGUGGCU-3' | 26 |
| 152 | 5' UTR | 5'-UGAUACUCACACAGUGGCUUCUGCU-3' | 27 |
| 153 | 5' UTR | 5'-GAUACUCACACAGUGGCUU-3' | 28 |
| 158 | 5' UTR | 5'-UCACACAGUGGCUUCUGCUCACCAA-3' | 29 |
| 190 | 5' UTR | 5'-AGACAGAUGCACCAACGAG-3' | 30 |
| 226 | 5' UTR | 5'-UGUAGAGGUCCAUCUGCGU-3' | 31 |
| 227 | 5' UTR | 5'-GUAGAGGUCCAUCUGCGUU-3' | 32 |
| 228 | 5' UTR | 5'-UAGAGGUCCAUCUGCGUUC-3' | 33 |
| 253 | 5' UTR | 5'-AGACGAUGCCAGAGCUAUG-3' | 34 |
| 254 | 5' UTR | 5'-GACGAUGCCAGAGCUAUGA-3' | 35 |
| 255 | 5' UTR | 5'-ACGAUGCCAGAGCUAUGAC-3' | 36 |
| 256 | 5' UTR | 5'-CGAUGCCAGAGCUAUGACU-3' | 37 |
| 405 | ORF | 5'-ACCACAGCAUGCACUUCCU-3' | 38 |
| 406 | ORF | 5'-CCACAGCAUGCACUUCCUU-3' | 39 |
| 412 | ORF | 5'-CAUGCACUUCCUUCCAGCAGCUACA-3' | 40 |
| 561 | ORF | 5'-CCACUACGGUGUUCAUGCA-3' | 41 |
| 561 | ORF | 5'-CCACUACGGUGUUCAUGCAUGUGAG-3' | 42 |
| 564 | ORF | 5'-CUACGGUGUUCAUGCAUGU-3' | 43 |

TABLE 1-continued

Exemplary PPARδ Target Sequences

| PPARδ Name | Region | Target Sequence | SEQ ID NO: |
|---|---|---|---|
| 605 | ORF | 5'-GUCGUACGAUCCGCAUGAA-3' | 44 |
| 608 | ORF | 5'-GUACGAUCCGCAUGAAGCU-3' | 45 |
| 624 | ORF | 5'-GCUGGAGUACGAGAAGUGU-3' | 46 |
| 626 | ORF | 5'-UGGAGUACGAGAAGUGUGA-3' | 47 |
| 668 | ORF | 5'-AGAACCGCAACAAGUGCCA-3' | 48 |
| 849 | ORF | 5'-GCACAUCUACAAUGCCUAC-3' | 49 |
| 849 | ORF | 5'-GCACAUCUACAAUGCCUACCUGAAA-3' | 50 |
| 947 | ORF | 5'-UCCACGACAUCGAGACAUU-3' | 51 |
| 1022 | ORF | 5'-ACAAGGAGAUCAGCGUGCACGUCUU-3' | 52 |
| 1028 | ORF | 5'-AGAUCAGCGUGCACGUCUU-3' | 53 |
| 1031 | ORF | 5'-UCAGCGUGCACGUCUUCUA-3' | 54 |
| 1140 | ORF | 5'-CCAGGUUACCCUUCUCAAG-3' | 55 |
| 1143 | ORF | 5'-GGUUACCCUUCUCAAGUAU-3' | 56 |
| 1193 | ORF | 5'-CCUCUAUCGUCAACAAGGA-3' | 57 |
| 1269 | ORF | 5'-CCGCAAACCCUUCAGUGAUAUCAUU-3' | 58 |
| 1271 | ORF | 5'-GCAAACCCUUCAGUGAUAUCAUUGA-3' | 59 |
| 1275 | ORF | 5'-ACCCUUCAGUGAUAUCAUU-3' | 60 |
| 1280 | ORF | 5'-UCAGUGAUAUCAUUGAGCCUAAGUU-3' | 61 |
| 1281 | ORF | 5'-CAGUGAUAUCAUUGAGCCUAAGUUU-3' | 62 |
| 1283 | ORF | 5'-GUGAUAUCAUUGAGCCUAA-3' | 63 |
| 1290 | ORF | 5'-CAUUGAGCCUAAGUUUGAA-3' | 64 |
| 1290 | ORF | 5'-CAUUGAGCCUAAGUUUGAAUUUGCU-3' | 65 |
| 1293 | ORF | 5'-UGAGCCUAAGUUUGAAUUU-3' | 66 |
| 1295 | ORF | 5'-AGCCUAAGUUUGAAUUUGCUGUCAA-3' | 67 |
| 1296 | ORF | 5'-GCCUAAGUUUGAAUUUGCU-3' | 68 |
| 1563 | ORF | 5'-GCGGAUCAAGAAGACCGAA-3' | 69 |
| 1609 | ORF | 5'-CAGGAGAUCUACAAGGACAUGUACU-3' | 70 |
| 3593 | 3' UTR | 5'-GGAUACAGCUCUUCUCAGU-3' | 71 |
| 3680 | 3' UTR | 5'-UAAAUAGUGUACACAGACU-3' | 72 |

In an embodiment, a PPARδ target sequence is at least 14 nucleotides in length. In aspects of this embodiment, a PPARδ target sequence comprises, e.g., 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, or 25 nucleotides in length. In other aspects of this embodiment, a PPARδ target sequence is SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, or SEQ ID NO: 72.

A PPARδ iRNA agent disclosed in the present specification can include a modification of a nucleotide comprising, e.g., a single-stranded PPARδ iRNA agent or a double-stranded PPARδ iRNA agent. A nucleotide is a molecule that contains a nitrogenous heterocyclic base moiety, such as, e.g., adenosine, guanine, cytosine, uracil or thymine; a sugar moiety, such as, e.g., pentose like ribose or a deoxyribose; and a phosphate moiety, such as, e.g., a pentavalent phosphate. As such, a nucleotide can include a chemical modification to a nitrogenous base moiety a sugar moiety, or phosphate moiety. In addition, nucleotides can be linked together to form oligonucleotides through their phosphate moieties and sugar moieties creating an internucleoside linkage. Thus, a nucleotide modification also embraces a chemical modification of an internucleoside linkage between two nucleotides. A nucleotide modification also comprises a substitution of a nucleotide with another natural nucleotide, such as, e.g., a ribonucleotide or a deoxyribonucleotide, a nucleotide analog, an abasic nucleotide, a non-nucleotide moiety, or any combination thereof. As used herein, the term "nucleotide analog" means a nucleotide which contains some type of modification to either a nitrogenous base moiety, a sugar moiety, or a phosphate moiety. As used herein, the term "abasic" or "abasic nucleotide" means a molecule that lacks a commonly recognized nitrogenous base moiety, such as, e.g., adenosine, guanine, cytosine, uracil or thymine and encompasses sugar moieties lacking a base or having other chemical groups in place of base at the 1' position. As used herein, the term "non-nucleotide moiety" means any molecule, other than a nucleotide or an abasic nucleotide, which can be incorporated into a nucleic acid molecule in the place of one or more of the original or endogenous nucleotides. It is understood that a nucleotide modification need only contain a single modification, but may also contain multiple modifications within one of the moieties or between different moieties.

A nucleotide modification of a PPARδ iRNA agent can modulate cellular uptake of a PPARδ iRNA agent; promote stability of a PPARδ iRNA agent; inhibit endonucleolytic degradation of a PPARδ iRNA agent; inhibit exonucleolytic degradation of a PPARδ iRNA agent; improve the pharmacokinetics of a PPARδ iRNA agent; inhibit off-target silencing of a PPARδ iRNA agent; or modulate binding affinity between the sense and the anti-sense sequences of a PPARδ iRNA agent. Nucleotide modifications and the procedures and reagents necessary to make such modifications to a nucleic acid molecule, such as, e.g., an iRNA agent, are known to a person of ordinary skill in the art, examples of which are described in, e.g., James Thompson et al., Nucleic Acid Molecules with Novel Chemical Compositions Capable of Modulating Gene Expression, U.S. Pat. No. 6,673,611 (Jan. 6, 2004); Brenda F. Baker, Oligomeric Compounds for Use in Gene Modulation, U.S. Patent Publication 2006/0241072 (Oct. 26, 2006); Antonin De Fougerolles et al, iRNA Agents Targeting VEGF, U.S. Patent Application 2006/

0223770 (Oct. 5, 2006); James McSwiggen et al., RNA Interference Mediated Inhibition of Gene Expression Using Chemically Modified Short Interfering Nucleic Acid (siRNA), U.S. Patent Publication 2006/0247429 (Nov. 2, 2006); Juergen Soutschek et al., RNAi Modulation of ApoB and Uses Thereof, U.S. Patent Publication 2006/0105976 (May 18, 2006); and Chandra Vargeese et al., RNA Interference Mediated Inhibition of Vascular Endothelial Growth Factor and Vascular Endothelial Growth Factor Receptor Gene Expression Using Short Interfering Nucleic Acid (siRNA), U.S. Patent Publication 2006/0217332 (Sep. 28, 2006), each of which is herein incorporated by reference in its entirety.

Thus, in an embodiment, a PPARδ iRNA agent includes one or more nucleotide modifications that can modulate the cellular uptake of a PPARδ iRNA agent. In another embodiment, a PPARδ iRNA agent includes one or more nucleotide modifications that can promote stability of a PPARδ iRNA agent. In yet another embodiment, a PPARδ iRNA agent includes one or more nucleotide modifications that can inhibit endonucleolytic degradation of a PPARδ iRNA agent. In still another embodiment, a PPARδ iRNA agent includes one or more nucleotide modifications that can inhibit exonucleolytic degradation of a PPARδ iRNA agent. In a further embodiment, a PPARδ iRNA agent includes one or more nucleotide modifications that improve the pharmacokinetics of a PPARδ iRNA agent. In another embodiment, a PPARδ iRNA agent includes one or more nucleotide modifications that inhibit off-target silencing of a PPARδ iRNA agent. In yet another embodiment, a PPARδ iRNA agent includes one or more nucleotide modifications that can modulate the binding affinity between the sense and the anti-sense sequences of the PPARδ iRNA agent.

In another embodiment, a single-stranded PPARδ iRNA agent comprises a nucleotide modification. In another embodiment, a single-stranded PPARδ iRNA agent comprises a nucleotide modification located in a sense sequence, an anti-sense sequence, or both a sense sequence and an anti-sense sequence. In another embodiment, a single-stranded PPARδ iRNA agent comprises a plurality of nucleotide modifications. In another embodiment, a single-stranded PPARδ iRNA agent plurality of nucleotide modifications located in a sense sequence, an anti-sense sequence, or both a sense sequence and an anti-sense sequence. In aspects of this embodiment, a single-stranded PPARδ iRNA agent can have, e.g., at least one nucleotide modification, at least two nucleotide modifications, at least three nucleotide modifications, at least four nucleotide modifications, at least five nucleotide modifications, at least six nucleotide modifications, at least seven nucleotide modifications, at least eight nucleotide modifications, at least nine nucleotide modifications, or at least ten nucleotide modifications. In other aspects of this embodiment, a single-stranded PPARδ iRNA agent can have, e.g., at most one nucleotide modification, at least two nucleotide modifications, at most three nucleotide modifications, at most four nucleotide modifications, at most five nucleotide modifications, at most six nucleotide modifications, at most seven nucleotide modifications, at most eight nucleotide modifications, at most nine nucleotide modifications, or at most ten nucleotide modifications. In other aspects of this embodiment, a single-stranded PPARδ iRNA agent can have, e.g., one to about 10 nucleotide modifications, about two to about eight nucleotide modifications, about two to about four nucleotide modifications, or one to about three nucleotide modifications.

In another embodiment, a double-stranded PPARδ iRNA agent comprises a nucleotide modification. In another embodiment, a double-stranded PPARδ iRNA agent comprises a nucleotide modification located in a sense sequence, an anti-sense sequence, or both a sense sequence and an anti-sense sequence. In another embodiment, a double-stranded PPARδ iRNA agent comprises a plurality of nucleotide modifications. In another embodiment, a double-stranded PPARδ iRNA agent plurality of nucleotide modifications located in a sense sequence, an anti-sense sequence, or both a sense sequence and an anti-sense sequence. In aspects of this embodiment, a double-stranded PPARδ iRNA agent can have, e.g., at least one nucleotide modification, at least two nucleotide modifications, at least three nucleotide modifications, at least four nucleotide modifications, at least five nucleotide modifications, at least six nucleotide modifications, at least seven nucleotide modifications, at least eight nucleotide modifications, at least nine nucleotide modifications, or at least ten nucleotide modifications. In other aspects of this embodiment, a double-stranded PPARδ iRNA agent can have, e.g., at most one nucleotide modification, at least two nucleotide modifications, at most three nucleotide modifications, at most four nucleotide modifications, at most five nucleotide modifications, at most six nucleotide modifications, at most seven nucleotide modifications, at most eight nucleotide modifications, at most nine nucleotide modifications, or at most ten nucleotide modifications. In other aspects of this embodiment, a double-stranded PPARδ iRNA agent can have, e.g., one to about 10 nucleotide modifications, about two to about eight nucleotide modifications, about two to about four nucleotide modifications, or one to about three nucleotide modifications.

In an embodiment, a PPARδ iRNA agent comprising a nucleotide modification includes replacement of one or more ribonucleotides with a natural nucleotide, such as, e.g., a ribonucleotide or a deoxyribonucleotide, a nucleotide analog, an abasic nucleotide, a non-nucleotide moiety, or any combination thereof. Natural nucleotides, without limitation, adenosine, guanine, cytosine, uracil or thymine, as well as, different purine or pyrimidine bases, such as uracil-5-yl (psi.), hypoxanthin-9-yl (I), and 2-aminoadenin-9-yl. Nucleotide analogs include, without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleotide analogs, such as, e.g., 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications, each of which is herein incorporated by reference in its entirety In another aspect of this embodiment, an iRNA agent has been modified by replacing one or more ribonucleotides with deoxyribonucleotides. Preferably, adjacent deoxyribonucleotides are joined by phosphorothioate linkages, and the PPARδ iRNA agent does not include more than four consecutive deoxyribonucleotides on the sense or the anti-sense strands. Replacement of the U with a C5 amino linker; replacement of an A with a G (sequence changes are preferred to be located on the sense strand and not the anti-sense strand); or modification of the sugar at the 2', 6', 7', or 8' position can also inhibit endonuclease cleavage of the PPARδ iRNA agent. Preferred embodiments are those in which one or more of these modifications are present on the region comprising the sense sequence but not the region comprising the anti-sense sequence, or embodiments where the region comprising the anti-sense sequence has fewer of such modifications.

In another aspect of this embodiment, a PPARδ iRNA agent can be modified by replacing one or more ribonucleotides with a ribonucleotide analog, see, e.g., Jasenka Matulic-Adamic et al., Nucleoside Analogs, U.S. Pat. No. 6,248,878 (Jun. 21, 2001); Muthiah Manoharan et al., Modified iRNA Agents, U.S. Patent Publication 2005/0107325 (May 19, 2005); and Muthiah Manoharan and Kallanthottathil G. Rajeev, Modified iRNA Agents, U.S. Patent Publication 2005/0164235 (Jul. 25, 2005); and Muthiah Manoharan and Kallanthottathil G. Rajeev, iRNA Agents with Biocleavable Tethers, U.S. Patent Publication 2005/0256069 (Nov. 17, 2005), each of which are hereby incorporated by reference in its entirety.

In another embodiment, a PPARδ iRNA agent comprises a nucleotide modification that includes a nucleobase modification, such as, e.g., a cationic modification, like a 3'-abasic cationic modification. The cationic modification can be, e.g., an alkylamino-dT moiety (e.g., a C6 amino-dT), an allylamino moiety, a pyrrolidine moiety, a pthalamido moiety, a hydroxyprolinol moiety, an aminooxy moiety, a polyamine moiety, a cationic peptide moiety, or a cationic amino acid moiety. The cationic modification can be located on one or more of the terminal nucleotides of a PPARδ iRNA agent, and be external or terminal cationic residue. An alkylamino-dT moiety is preferably attached to the 3'-end of the sense sequence or anti-sense sequence of a PPARδ iRNA agent. A pyrrolidine moiety is preferably attached to the 3'- or 5'-end of the sense sequence, or the 3'-end of the anti-sense sequence. An allyl amine uridine moiety is preferably on the 3'- or 5'-end of the sense sequence, and not on the 5'-end of the anti-sense sequence. An aminooxy moiety can be attached to a hydroxyl prolinol and at the 3'- or 5'-end of either the sense or anti-sense sequences. These chemical modifications can, e.g., inhibit exonucleolytic degradation of a PPARδ iRNA agent.

In another embodiment, a PPARδ iRNA agent comprises a nucleotide modification that includes a non-nucleotide moiety. Non-limiting examples of a non-nucleotide moiety include a 2'-O-methyl (2'-OMe) pyrimidine nucleotide, 2'-deoxy nucleotide (e.g., deoxy-cytodine), 2'-deoxy-2'-fluoro (2'-F) pyrimidine nucleotide, 2'-O-methoxyethyl (2'-O-MOE), 2'-O-aminopropyl (2'-O-AP), 2'-O—N-methylacetamido (2'-O-NMA), 2'-O-dimethylaminoethlyoxyethyl (2'-O-DMAEOE), 2'-O-dimethylaminoethyl (2'-O-DMAOE), 2'-O-dimethylaminopropyl (2'-O-AP), 2'-hydroxy nucleotide, or a 2'-ara-fluoro nucleotide, or a locked nucleic acid (LNA), extended nucleic acid (ENA), hexose nucleic acid (HNA), cyclohexene nucleic acid (CeNA), ribo-difluorotoluoyl, 5-allyamino-pyrimidines, or 5-Me-2'-modified pyrimidines. A 2' modification is preferably a 2'-OMe modification, and more preferably, a 2'-fluoro modification. In a preferred embodiment, one or more 2' modified nucleotides are on the sense sequence of the PPARδ iRNA agent.

In another embodiment, a PPARδ iRNA agent comprising a nucleotide modification includes a modification of a sugar moiety. In an aspect of this embodiment, a PPARδ iRNA agent includes a sugar modification at the 2' position, at the 3' position or at both the at the 2' position and at the 3' position. In another aspect of this embodiment, one or more terminal nucleotides of a PPARδ iRNA agent include a sugar modification at the 2' position, at the 3' position or at both the at the 2' position and at the 3' position. Sugar modifications can be made at other positions on the sugar, particularly the 3' position of the sugar on the 3' terminal nucleotide or in 2'-5' linked oligonucleotides and the 5' position of 5' terminal nucleotide. In another aspect of this embodiment, a PPARδ iRNA agent includes an L-sugar. Sugar modifications, without limitation, OH; F; O-, S-, or N-alkyl; O-, S-, or N-alkenyl; O-, S- or N-alkynyl; or O-alkyl-O-alkyl, wherein the alkyl, alkenyl and alkynyl may be a substituted or unsubstituted $C_1$ to $C_{10}$, alkyl or $C_2$ to $C_{10}$ alkenyl and alkynyl. Sugar modifications also include, without limitation, $-O[(CH_2)_nO]_mCH_3$, $-O(CH_2)_n$ $OCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m are from 1 to about 10. Other sugar modifications include, without limitation, $C_1$ to $C_{10}$ lower alkyl, substituted lower alkyl, alkaryl, aralkyl, O-alkaryl or O-aralkyl, $-SH$, $-SCH_3$, $-OCN$, Cl, Br, $-CN$, $-CF_3$, $-OCF_3$, $-SOCH_3$, $-SO_2-CH_3$, $-ONO_2$, $-NO_2$, $-N_3$, $-NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Modified sugars would also include those that contain modifications at the bridging ring oxygen, such as, e.g., $-CH_2$ and S. Nucleotide sugar analogs include, e.g., a glycoconjugate or alkylglycoside component, like glucose, mannose, 2-deoxyglucose, or an analog thereof. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety. These and other sugar modifications are known to a person of ordinary skill in the art, see, e.g., Pierre Martin et al., Sugar-Modified Gapped Oligonucleotides, U.S. Pat. No. 6,451,991 (Sep. 17, 2002); Alexander Karpeisky and Leonid Beigelman, 2'-O-Amino-Containing Nucleoside Analogs and Polynucleotides, U.S. Pat. No. 6,506,888 (Jan. 14, 2003); and Muthiah Manoharan and Venkatraman Mohan, Oligonucleotides Having A-DNA Form and B-DNA Form Conformational Geometry, U.S. Pat. No. 6,737,520 (May 18, 2004), each of which is herein incorporated by reference in its entirety.

In another embodiment, one or more terminal nucleotides have a 2'-5' linkage. Preferably, a 2'-5' linkage occurs on the sense sequence, e.g., the 5' end of the sense sequence.

In another embodiment, a PPARδ iRNA agent comprising a nucleotide modification includes a modification of a phosphate moiety. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In an aspect of this embodiment, a PPARδ iRNA agent comprising a nucleotide modification includes one or more internucleotide linkages. Modified phosphate moieties can be modified so that the linkage between two nucleotides contains a phosphorothioate, chiral phosphorothioate, phosphorodithioate, phosphotriester, aminoalkylphosphotriester, methyl and other alkyl phosphonates, such as, e.g., 3'-alkylene phosphonate and chiral phosphonates, phosphinates, phosphoramidates, such as, e.g., 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety. Nucleotide modification of a phosphate moiety can, e.g., promote stability of a PPARδ iRNA agent, preserve RNAi activity of the agents in a cell, and inhibit endonucleolytic degradation of a PPARδ iRNA agent.

In another aspect of this embodiment, a PPARδ iRNA agent comprises a nucleotide modification that includes one or more phosphate groups or one or more analogs of a phosphate group, e.g., a phosphoryl analog, at the 5'-end of the sequence. 5'-phosphate modifications include those which are compatible with RISC mediated gene silencing, include, without limitation, 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g. RP(OH)(O)—O-5'-).

In another embodiment, the first and preferably the first two internucleotide linkages at the 5' end of a sense sequence, an anti-sense sequence, or both a sense and an anti-sense sequences are modified, preferably by a phosphorothioate. In another aspect of this embodiment, the first, and preferably the first two, three, or four internucleotide linkages at the 3'-end of a sense sequence, an anti-sense sequence, or both a sense and an anti-sense sequences are modified, preferably by a phosphorothioate. In another aspect of this embodiment, the 5'-end of both the sense and anti-sense sequences, and the 3'-end of both the sense and anti-sense sequences are modified as described. In another embodiment, a PPARδ iRNA agent includes a phosphorothioate linkage or P-alkyl modification in the linkages between one or more of the terminal nucleotides of a PPARδ iRNA agent. In another embodiment, a PPARδ iRNA agent includes a methylphosphonate at one or more terminal nucleotides to enhance exonuclease resistance, e.g., at the 3'-end of the sense or anti-sense strands of a PPARδ iRNA agent. While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules. These and other internucleotide linkages are known to a person of ordinary skill in the art, see, e.g., Leonid Beigelman et al., Nucleoside triphosphates and their incorporation into oligonucleotides, U.S. Pat. No. 6,482,932 (Nov. 19, 2002), which is herein incorporated by reference in its entirety.

The chemical modifications can be combined onto a single PPARδ iRNA agent. For example, in one embodiment, at least one terminal nucleotide of a PPARδ iRNA agent has a phosphorothioate linkage and a 2' sugar modification, e.g., a 2'F or 2'OMe modification. In another embodiment, at least one terminal nucleotide of an iRNA agent has a 5' Me-pyrimidine and a 2' sugar modification, e.g., a 2'F or 2'OMe modification.

In another embodiment, a sense sequence, an anti-sense sequence, or both a sense sequence and an anti-sense sequence of a PPARδ iRNA agent includes modifications at the 3'-end, 5'-end, or both the 3'- and 5'-ends of a PPARδ iRNA agent. Such modifications can be at the 3'-end, 5'-end or both ends of the molecule. They can include modification or replacement of an entire terminal phosphate or of one or more of the atoms of the phosphate group. For example, the 3' and 5' ends of a sense and/or anti-sense sequence can be conjugated to other functional molecular entities such as protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two sequences of a PPARδ iRNA agent, the array can substitute for a hairpin RNA loop in a hairpin-type RNA agent. The 3'-end can be an OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance.

It is also understood in a nucleotide modification includes the replacement of both the sugar and the phosphate moieties by, e.g., an amide type linkage (aminoethylglycine) found in peptide nucleic acid (PNA) molecules. These and other amide type linkages are known to a person of ordinary skill in the art, see, e.g., U.S. Pat. Nos. 5,539,082; 5,714,331; and 5,719,262, each of which is herein incorporated by reference in its entirety.

In another embodiment, a sense sequence, an anti-sense sequence, or both a sense sequence and an anti-sense sequence of a PPARδ iRNA agent includes a conjugate, such as, e.g., small molecules, lipids, phospholipids, nucleosides, nucleotides, nucleic acids, antibodies, toxins, negatively charged polymers and other polymers, for example, proteins, peptides, hormones, carbohydrates, polyethylene glycols, or polyamines, across cellular membranes. Non-limiting examples of a conjugate include, conjugates, such as, e.g., a lipophile; a terpene; a nucleic acid aptamer; naproxen; nitroindole; a thioether, e.g., hexyl-S-tritylthiol; a vitamin and other co-factor, such as, e.g., folate, retinol, retinoids, vitamin E, and N-acetylgalactosamine; an aliphatic chain, such as, e.g., dodecandiol or undecyl residues; a polymer, such as, e.g., a polyethyleneglycol like PEG 5 and PEG20; a polyamine, such as, e.g., spermine or spermidine; a peptide, such as, e.g., a ligand for cellular receptors, protein localization sequences antibodies; lipids, such as, e.g., a phospholipid, like di-hexadecyl-rac-glycerol or triethylammonium 1,2-di-O-hexadecyl-rac-glycero-3-H-phosphonate, a palmityl moiety, a glyceride lipid, a cholanic acid, a cholic acid, a cholesterol, thio-cholesterol, an octadecylamine or a hexylamino-carbonyl-oxycholesterol moiety. Such conjugates can facilitate or improve delivery and/or localization of a PPARδ iRNA agent into a number of cell types originating from different tissues in a mammal, in the presence or absence of serum, see, e.g., Sullenger and Cech, U.S. Pat. No. 5,854,038. The conjugates can also impart therapeutic activity by transferring therapeutic compounds across cellular membranes, altering the pharmacokinetics, and/or modulating the localization of nucleic acid molecules of the invention. Conjugates of the molecules described herein can be attached to biologically active molecules via linkers that are biodegradable, such as biodegradable nucleic acid linker molecules. Preferably, conjugates are on the 3'-end of the anti-sense sequence, or on the 5'- or 3'-end of the sense sequence, and preferably the conjugates are not on the 3' end of the anti-sense sequence and on the 3'-end of the sense sequence. These conjugates can, e.g., modulate the cellular uptake of a PPARδ iRNA agent, inhibit endonucleolytic degradation of a PPARδ iRNA agent and inhibit exonucleolytic degradation of a PPARδ iRNA agent. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

In an aspect of this embodiment, the conjugate is naproxen, and the conjugate is preferably on the 5'- or 3'-end of the sense or anti-sense sequences. In another aspect of this embodiment, the conjugate is cholesterol or thiocholesterol, and the conjugate is preferably on the 5'- or 3'-end of the sense sequence and preferably not present on the anti-sense sequence. In other aspects of this embodiment, the cholesterol is conjugated to a PPARδ iRNA agent by a pyrrolidine linker, serinol linker, aminooxy linker, or hydroxyprolinol linker. In another aspect of this embodiment, the conjugate is a dU-cholesterol, or cholesterol is conjugated to the PPARδ iRNA agent by a disulfide linkage. In another aspect of this embodiment, the conjugate is cholanic acid, and the cholanic acid is attached to the 5'- or 3'-end of the sense sequence, or the 3'-end of the anti-sense sequence. In another aspect of this embodiment, the cholanic acid is attached to the 3' end of the sense sequence and the 3'-end of the anti-sense sequence. In another aspect of this embodiment, the conjugate is retinol, and the retinol is attached to the 5'- or 3'-end of the sense sequence, or the 3'-end of the anti-sense sequence. In one embodiment, the retinol is attached to the 3'-end of the sense sequence and the 3'-end of the anti-sense sequence. In another embodiment, the conjugate is PEGS, PEG20, or naproxen.

In another embodiment, a PPARδ iRNA agent can be conjugated to an enzyme substrate, such as, e.g., a substrate for which the relative enzyme is present in a higher amount, as compared to the enzyme level in other tissues of the body, like in tissues other than the eye.

In another aspect of this embodiment, a PPARδ iRNA agent can be complexed to a delivery agent that features a modular complex. The complex can include a carrier agent linked to one or more of (preferably two or more, more preferably all three of): (a) a condensing agent (e.g., an agent capable of attracting, such as, e.g., binding, a nucleic acid, e.g., through ionic or electrostatic interactions); (b) a fusogenic agent, such as, e.g., an agent capable of fusing and/or being transported through a cell membrane); and (c) a targeting group, such as, e.g., a cell or tissue targeting agent like a lectin, glycoprotein, lipid or protein conjugate. Non-limiting examples of delivery agents that can be complexed to a PPARδ iRNA agents are described in, e.g., Muthiah Manoharan et al., Modified iRNA Agents, U.S. Patent Publication 2005/0107325 (May 19, 2005); and Muthiah Manoharan and Kallanthottathil G. Rajeev, Modified iRNA Agents, U.S. Patent Publication 2005/0164235 (Jul. 25, 2005); and Muthiah Manoharan and Kallanthottathil G. Rajeev, iRNA Agents with Biocleavable Tethers, U.S. Patent Publication 2005/0256069 (Nov. 17, 2005), each of which are hereby incorporated by reference in its entirety Other suitable modifications to a sugar, base, or backbone of a PPARδ iRNA agent are described in, e.g., Christoph Westphal and Robert Langer, Therapeutics Compositions, International Patent Publication No. WO 2004/064737 (Aug. 5, 2004), which is herein incorporated by reference in its entirety. A PPARδ iRNA agent can include a non-naturally occurring base, see, e.g., Muthiah Manoharan, Protected Monomers, International Patent Publication No. WO 2004/094345 (Nov. 4, 2005), which is herein incorporated by reference in its entirety. A PPARδ iRNA agent can include a non-naturally occurring sugar, such as a non-carbohydrate cyclic carrier molecule, see, e.g., Muthiah Manoharan et al., Modified iRNA Agents, U.S. Patent Publication 2005/0107325 (May 19, 2005); and Muthiah Manoharan and Kallanthottathil G. Rajeev, Modified iRNA Agents, U.S. Patent Publication 2005/0164235 (Jul. 25, 2005), each of which are hereby incorporated by reference in its entirety.

A PPARδ iRNA agent can be rationally designed based on sequence information and desired characteristics and the information of the PPARδ target sequence. For example, a PPARδ iRNA agent can be designed according to the relative melting temperature of the candidate duplex. Generally, the duplex should have a lower melting temperature at the 5'-end of the anti-sense strand than at the 3'-end of the anti-sense strand. The methods and procedures for designing and making a iRNA molecule are known to a person of ordinary skill in the art, see, e.g., Yi Pei and Thomas Tuschl, *On the Art of Identifying Effective and Specific siRNAs*, 3(9) Nat. Methods 670-676 (2006), Thompson et al., supra, (2004); Baker, supra, (2006); De Fourgerolles et al, supra, (2006); McSwiggen et al., supra, (2006); Soutschek et al., supra, (2006); and Vargeese et al., supra, (2006), each of which is herein incorporated by reference in its entirety. Synthesis of a PPARδ iRNA agent can be synthesized using protocols known to a person of ordinary skill in the art, e.g., as described in Thompson et al., supra, (2004); Baker, supra, (2006); De Fourgerolles et al, supra, (2006); McSwiggen et al., supra, (2006); Soutschek et al., supra, (2006); and Vargeese et al., supra, (2006), each of which is herein incorporated by reference in its entirety.

Aspects of the present invention provide, in part, an expression construct. An expression construct comprises a nucleic acid molecule encoding a PPARδ iRNA agent operably-linked to an expression vector useful for expressing the PPARδ iRNA agent in a cell or cell-free extract. A wide variety of expression vectors can be employed for expressing a nucleic acid molecule encoding a PPARδ iRNA agent, including, without limitation, plasmid- or viral vectors, see, e.g., Maciej Wiznerowicz et al., *Tuning Silence: Conditional Systems for RNA Interference*, 3(9) Nat. Methods 682-688m (2006); Ola Snøve and John J. Rossi, *Expressing Short Hairpin RNAi in vivo*, 3(9) Nat. Methods 689-698 (2006); and Charles X. Li et al., *Delivery of RNA Interference*, 5(18) Cell Cycle 2103-2109 (2006). A viral-based vector can be derived from, e.g., an adeno-associated virus, a retrovirus, an adenovirus, or an alphavirus. It is further understood that expression vectors useful to practice aspects of the invention may include those which express a PPARδ iRNA agent under control of a constitutive, tissue-specific, cell-specific or inducible promoter element, enhancer element or both. Expression vectors capable of expressing a PPARδ iRNA agent can provide persistent or stable expression of the PPARδ iRNA agent. Alternatively, expression vectors capable of expressing a PPARδ iRNA agent can provide for transient expression of the PPARδ iRNA agent. Once expressed, a PPARδ iRNA agent interacts with the target PPARδ molecules and generates an RNAi response.

Thus, in an embodiment, an expression construct comprises an expression vector operably-linked to a polynucleotide molecule encoding a PPARδ iRNA agent. In an aspect of this embodiment, an expression construct comprises a plasmid expression vector operably-linked to a polynucleotide molecule encoding a PPARδ iRNA agent. In another aspect of this embodiment, an expression construct comprises a viral expression vector operably-linked to a polynucleotide molecule encoding a PPARδ iRNA agent. In further aspects of this embodiment, a viral expression vector is one derived from an adeno-associated virus, a retrovirus, an adenovirus, or an alphavirus. In still further aspects of this embodiment, an expression construct expresses a PPARδ iRNA agent under the control of a constitutive promoter element, enhancer element or both, a tissue-specific promoter element, enhancer element or both, a cell-specific promoter element, enhancer element or both, or an inducible promoter element, enhancer element or both. In another aspect of this embodiment, an expression construct transiently expresses a PPARδ iRNA agent. In another aspect of this embodiment, an expression construct constitutively expresses a PPARδ iRNA agent.

Aspects of the present invention provide, in part, a composition comprising a PPARδ iRNA agent. It is envisioned that any of the composition disclosed in the present specification can be useful in a method of treating an ocular disease associated with an unwanted PPARδ activity in a patient in need thereof, with the proviso that the composition prevents or reduces a symptom associated with the ocular disease. Non-limiting examples of compositions comprising a PPARδ iRNA agent include a single-stranded PPARδ iRNA agent and a double stranded PPARδ iRNA agent as disclosed in the present specification. Additionally, a PPARδ iRNA agent included in a composition comprising a PPARδ iRNA agent can be an unmodified or modified PPARδ iRNA agent alone, in conjunction with a delivery reagent, or as part of an expression vector which expresses the PPARδ iRNA agent within cells exhibiting unwanted PPARδ activity. It is also understood that the two or more different PPARδ iRNA agents can be provided as separate compositions or as part of a single composition.

A composition useful in the invention generally is administered as a pharmaceutical acceptable composition comprising a PPARδ iRNA agent. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the PPARδ iRNA agents disclosed in the present specification. A pharmaceutical composition comprising a PPARδ iRNA agent is useful for medical and veterinary applications. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition comprising a PPARδ iRNA agent can optionally include a pharmaceutically acceptable carriers that facilitate processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, $7^{th}$ ed. 1999); REMINGTON: THE SCIENCE AND PRACTICE OF PHARMACY (Alfonso R. Gennaro ed., Lippincott, Williams & Wilkins, $20^{th}$ ed. 2000); GOODMAN & GILMAN'S THE PHARMACOLOGICAL BASIS OF THERAPEUTICS (Joel G. Hardman et al., eds., McGraw-Hill Professional, $10^{th}$ ed. 2001); and HANDBOOK OF PHARMACEUTICAL EXCIPIENTS (Raymond C. Rowe et al., APhA Publications, $4^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

In an embodiment, a composition comprising a PPARδ iRNA agent is a pharmaceutical composition comprising a PPARδ iRNA agent. In aspects of this embodiment, a pharmaceutical composition comprising a PPARδ iRNA agent further comprises a pharmacological carrier, a pharmaceutical component, or both a pharmacological carrier and a pharmaceutical component. In other aspects of this embodiment, a pharmaceutical composition comprising a PPARδ iRNA agent further comprises at least one pharmacological carrier, at least one pharmaceutical component, or at least one pharmacological carrier and at least one pharmaceutical component.

Aspects of the present invention provide, in part, an ocular disease associated with an unwanted PPARδ activity. As used herein, the term "an ocular disease associated with an unwanted PPARδ activity" means that at least one of the underlying causes of an ocular disease is the unwanted presence of PPARδ activity. Non-limiting examples of an ocular disease associated with an unwanted PPARδ activity include wet Age-Related Macular Degeneration, dry Age-Related Macular Degeneration, Best's vitelliform macular degeneration, glaucoma, retinitis pigmentosa, diabetic retinopathy, macular edema and any degenerative disease of either the photoreceptors or the RPE.

In one embodiment, a patient suffering from an ocular disease associated with an unwanted PPARδ activity is treated with a composition comprising a PPARδ iRNA agent. In an aspect of this embodiment, a patient suffering from Age-Related Macular Degeneration is treated with a composition comprising a PPARδ iRNA agent. In aspects of this embodiment, a patient suffering from Age-Related Macular Degeneration is treated with a composition comprising a PPARδ iRNA agent is suffering from, e.g., wet Age-Related Macular Degeneration or dry Age-Related Macular Degeneration. In another aspect of this embodiment, a patient suffering from Best's vitelliform macular degeneration is treated with a composition comprising a PPARδ iRNA agent. In another aspect of this embodiment, a patient suffering from glaucoma is treated with a composition comprising a PPARδ iRNA agent. In another aspect of this embodiment, a patient suffering from neovascular glaucoma is treated with a composition comprising a PPARδ iRNA agent. In another aspect of this embodiment, a patient suffering from retinitis pigmentosa is treated with a composition comprising a PPARδ iRNA agent. In another aspect of this embodiment, a patient suffering from diabetic retinopathy is treated with a composition comprising a PPARδ iRNA agent. In another aspect of this embodiment, a patient suffering from macular edema is treated with a composition comprising a PPARδ iRNA agent. In another aspect of this embodiment, a patient suffering from a degenerative disease of the photoreceptors is treated with a composition comprising a PPARδ iRNA agent. In another aspect of this embodiment, a patient suffering from a degenerative disease of the RPE is treated with a composition comprising a PPARδ iRNA agent.

Aspects of the present invention provide, in part, administering a composition comprising a PPARδ iRNA agent. As used herein, the term "administering" means any delivery mechanism that provides a composition comprising a PPARδ iRNA agent to a patient that potentially results in a clinically, therapeutically, or experimentally beneficial result. A PPARδ iRNA agent can be delivered to a patient using a cellular uptake approach where a PPARδ iRNA agent is delivered intracellular or a gene therapy approach where a PPARδ iRNA agent is express derived from precursor RNAs expressed from an expression vectors.

A composition comprising a PPARδ iRNA agent as disclosed in the present specification can be administered to a patient using a cellular uptake approach by a cell expressing unwanted PPARδ activity. Administration of a composition comprising a PPARδ iRNA agent using a cellular uptake approach comprise a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A composition comprising a PPARδ iRNA agent can be administered to a patient by a variety of methods known to those of skill in the art, including, but not restricted to, encapsulation in liposomes, by ionophoresis, or by incorporation into other vehicles, such as hydrogels, cyclodextrins, biodegradable nanocapsules, and bioadhesive microspheres, or by proteinaceous vectors. Delivery mechanisms for administering a composition comprising a PPARδ iRNA agent to a patient are described in, e.g., Leonid Beigelman et al., Compositions for the Delivery of Negatively Charged Molecules, U.S. Pat. No. 6,395,713 (May 28, 2002); and Achim Aigner, Delivery Systems for the Direct Application of siRNAs to Induce RNA Interference (RNAi) in vivo, 2006(716559) J. Biomed. Biotech. 1-15 (2006); Controlled Drug Delivery: Designing Technologies for the Future (Kinam Park & Randy J. Mrsny eds., American Chemical Association, 2000); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/0137059 (Jul. 15, 2004); Patrick M. Hughes et al., Anti-Angiogenic Sustained Release Intraocular Implants and Related Methods, U.S. patent application Ser. No. 11/364,687 (Feb. 27, 2006); and Patrick M. Hughes et al., Sustained Release Intraocular Drug Delivery Systems, U.S. Patent Publication 2006/0182783 (Aug. 17, 2006), each of which is hereby incorporated by reference in its entirety.

A composition comprising a PPARδ iRNA agent as disclosed in the present specification can also be administered to a patient using a gene therapy approach by expressing a PPARδ iRNA agent within the cell expressing unwanted PPARδ activity. A PPARδ iRNA agent can be expressed from nucleic acid molecules operably-linked to an expression vector, see, e.g., P. D. Good et al., *Expression of Small, Therapeutic RNAs in Human Cell Nuclei*, 4(1) Gene Ther. 45-54 (1997); James D. Thompson, Polymerase III-based expression of therapeutic RNAs, U.S. Pat. No. 6,852,535 (Feb. 8, 2005); Maciej Wiznerowicz et al., *Tuning Silence: Conditional Systems for RNA Interference*, 3(9) Nat. Methods 682-688m (2006); Ola Snøve and John J. Rossi, *Expressing Short Hairpin RNAi in vivo*, 3(9) Nat. Methods 689-698 (2006); and Charles X. Li et al., *Delivery of RNA Interference*, 5(18) Cell Cycle 2103-2109 (2006). A person of ordinary skill in the art would realize that any PPARδ iRNA agent can be expressed in eukaryotic cells using an appropriate expression vector.

Expression vectors capable of expressing a PPARδ iRNA agent can provide persistent or stable expression of the PPARδ iRNA agent in cell exhibiting unwanted PPARδ activity. Alternatively, expression vectors capable of expressing a PPARδ iRNA agent can provide for transient expression of the PPARδ iRNA agent in cell exhibiting unwanted PPARδ activity. Such transiently expressing vectors can be repeatedly administered as necessary. A PPARδ iRNA agent-expressing vectors can be administered by a delivery mechanism and route of administration discussed above, by administration to target cells ex-planted from a patient followed by reintroduction into the patient, or by any other means that would allow for introduction into the desired target cell, see, e.g., Larry A. Couture and Dan T. Stinchcomb, *Anti-gene Therapy: The Use of Ribozymes to Inhibit Gene Function*, 12(12) Trends Genet. 510-515 (1996).

The actual delivery mechanism used to administer a composition comprising a PPARδ iRNA agent to a patient can be determined by a person of ordinary skill in the art by taking into account factors, including, without limitation, the type of ocular disease, the location of the ocular disease, the cause of the ocular disease, the severity of the ocular disease, the degree of relief desired, the duration of relief desired, the particular PPARδ iRNA agent used, the rate of excretion of the PPARδ iRNA agent used, the pharmacodynamics of the PPARδ iRNA agent used, the nature of the other compounds to be included in the composition, the particular route of administration, the particular characteristics, history and risk factors of the patient, such as, e.g., age, weight, general health and the like, or any combination thereof.

In an embodiment, a composition comprising a PPARδ iRNA agent is administered topically to an eye of a patient. In aspects of this embodiment, administration of a composition comprising a PPARδ iRNA agent is by, e.g., a liquid drop, a spray, a gel, a cream, an ointment, electroporation, or iontophoresis. Droppable liquids, sprays, gels, creams and ointments can be delivered by ocular delivery systems known in the art such as applicators or eye droppers. A composition comprising a PPARδ iRNA agent can be administered directly to the surface of the eye or to the interior of the eyelid.

In another embodiment, a composition comprising a PPARδ iRNA agent is administered to an eye by injection. In aspects of this embodiment, administration of a composition comprising a PPARδ iRNA agent an iRNA agent is by, e.g., intraocular injection, retinal injection, or subretinal injection. In an aspect of this embodiment, a composition comprising a PPARδ iRNA agent an iRNA agent is administered to an eye by a gene gun.

In another embodiment, a composition comprising a PPARδ iRNA agent is administered to an eye by a placement device. In an aspect of this embodiment, administration of a composition comprising a PPARδ iRNA agent an iRNA agent is by a catheter. In another aspect of this embodiment, administration of a composition comprising a PPARδ iRNA agent an iRNA agent is by an implant. In aspect of this embodiment, administration of a composition comprising a PPARδ iRNA agent an iRNA agent is by an intraocular implant. In aspect of this embodiment, an intraocular can be a biodegradable implant or a non-biodegradable implant. An intraocular implant can be inserted into, e.g., an anterior chamber of the eye, a posterior chamber of the eye, a region of the sclera, a transchoroidal space, or an avascularized region exterior to the vitreous. In another aspect of this embodiment, administration of a composition comprising a PPARδ iRNA agent an iRNA agent is by a retinal pellet. In another embodiment, the implant is positioned over an avascular region, such as on the sclera, so as to allow for transcleral diffusion of the drug to the desired site of treatment, e.g., to the intraocular space and macula of the eye. Furthermore, the site of transcleral diffusion is preferably in proximity to the macula.

In another embodiment, a composition comprising a PPARδ iRNA agent is administered to an eye by expression from an expression vector.

A composition comprising a PPARδ iRNA agent can be administered to a patient using a variety of routes. Routes of administration suitable for a method of treating an ocular disease as disclosed in the present specification include both local and systemic administration. Local administration results in significantly more delivery of a composition to a specific location as compared to the entire body of the patient, whereas, systemic administration results in delivery of a composition to essentially the entire body of the patient. Routes of administration suitable for a method of treating an ocular disease as disclosed in the present specification also include both central and peripheral administration. Central administration results in delivery of a composition to essentially the central nervous system of the patient and includes, e.g., intrathecal administration, epidural administration as well as a cranial injection or implant. Peripheral administration results in delivery of a composition to essentially any area of a patient outside of the central nervous system and encompasses any route of administration other than direct administration to the spine or brain. The actual route of administration of a composition comprising a PPARδ iRNA agent used in a patient can be determined by a person of ordinary skill in the art by taking into account factors, including, without limitation, the type of ocular disease, the location of the ocular disease, the cause of the ocular disease, the severity of the ocular disease, the degree of relief desired, the duration of relief desired, the particular PPARδ iRNA agent used, the rate of excretion of the PPARδ iRNA agent used, the pharmacodynamics of the PPARδ iRNA agent used, the nature of the other compounds to be included in the composition, the particular route of administration, the particular characteristics, history and risk factors of the patient, such as, e.g., age, weight, general health and the like, or any combination thereof.

In an embodiment, a composition comprising a PPARδ iRNA agent is administered locally to a patient. In aspects of this embodiment, a composition comprising a PPARδ iRNA agent an iRNA agent is administered to one eye of a patient or both eyes of a patient.

A composition comprising a PPARδ iRNA agent can be administered to a patient after onset of an ocular disease associated with an unwanted PPARδ activity, such as, e.g., when symptoms of the ocular disease are first apparent. Additionally, a composition comprising a PPARδ iRNA agent can be administered to a patient prior to the onset of an ocular disease associated with an unwanted PPARδ activity, such as, e.g., when symptoms of the ocular disease are not apparent. Such prophylactic administered to a patient is to slow or prevent the onset of an ocular disease associated with an unwanted PPARδ activity. For example, a composition comprising a PPARδ iRNA agent can be administered to an individual who is susceptible to or otherwise at risk for an ocular disease associated with an unwanted PPARδ activity. A person of ordinary skill in the art will be able to determine an appropriate candidate for receiving a composition comprising a PPARδ iRNA agent based on, e.g., the particular ocular disease to be treated, the presence of symptoms of an ocular disease, the likelihood of symptoms of an ocular disease, or any combination thereof.

Aspects of the present invention provide, in part, administering an effective amount of a composition comprising a PPARδ iRNA agent. As used herein, the term "effective amount" is synonymous with "effective dose" and when used in reference to treating an ocular disease associated with an unwanted PPARδ activity means the minimum dose of a PPARδ iRNA agent necessary to achieve the desired therapeutic effect and includes a dose sufficient to reduce a symptom associated with an ocular disease. In aspects of this embodiment, an effect amount of a composition comprising a PPARδ iRNA agent reduces a symptom associated with an ocular disease associated with an unwanted PPARδ activity by, e.g., at least 30%, at least 40%, at least 50%, at least 60%, at least 70%, at least 80%, at least 90% or at least 100%. In other aspects of this embodiment, an effect amount of a composition comprising a PPARδ iRNA agent reduces a symptom associated with an ocular disease associated with an unwanted PPARδ activity by, e.g., at most 30%, at most 40%, at most 50%, at most 60%, at most 70%, at most 80%, at most 90% or at most 100%. In yet other aspects of this embodiment, an effect amount of a composition comprising a PPARδ iRNA agent reduces an unwanted PPARδ activity by, e.g., at least 30%, at least 40%, at least 50%, at least 60%, at least 70%, at least 80%, at least 90% or at least 100%. In yet other aspects of this embodiment, an effect amount of a composition comprising a PPARδ iRNA agent reduces an unwanted PPARδ activity by, e.g., at most 30%, at most 40%, at most 50%, at most 60%, at most 70%, at most 80%, at most 90% or at most 100%.

The appropriate effective amount to be administered for a particular treatment can be determined by a person of ordinary skill in the art, using the guidance provided herein. As a non-limiting example, when administering a composition comprising a PPARδ iRNA agent to a patient, an effective amount generally is in the range of about 1.0 µg/kg to about 100 mg/kg of body weight per administration. In aspects of this embodiment, an effective amount of a composition comprising a PPARδ iRNA agent can be, e.g., about 1.0 µg/kg to about 1.0 mg/kg of body weight per administration, 10 µg/kg to about 10 mg/kg of body weight per administration, or 100 µg/kg to about 100 mg/kg of body weight per administration. As another non-limiting example, when administering a composition comprising a PPARδ iRNA agent to an eye of a patient, an effective amount generally is in the range of about 0.00001 mg to about 3.0 mg per eye. In aspects of this embodiment, an effective amount of a composition comprising a PPARδ iRNA agent can be, e.g., about 0.0001 mg to about 0.001 mg per eye, about 0.03 mg to about 3.0 mg per eye, about 0.1 mg to about 3.0 mg per eye or about 0.3 mg to about 3.0 mg per eye. In is known by a person of ordinary skill in the art that an effective amount of a composition comprising a PPARδ iRNA agent can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

Treatment of an ocular disease associated with an unwanted PPARδ activity may comprise a one-time administration of an effective dose of a composition comprising a PPARδ iRNA agent. As a non-limiting example, an effective dose of a composition comprising a PPARδ iRNA agent can be administered once to a patient, e.g., as a single injection or deposition at or near the site exhibiting unwanted PPARδ activity. Alternatively, treatment of an ocular disease associated with an unwanted PPARδ activity may comprise multiple administrations of an effective dose of a composition comprising a PPARδ iRNA agent carried out over a range of time periods, such as, e.g., hourly, daily, once every few days, weekly, or monthly. As a non-limiting example, a composition comprising a PPARδ iRNA agent can be administered once or twice daily to a patient for a period of from about seven to about ten days. The timing of administration can vary from patient to patient, depending upon such factors as the severity of a patient's symptoms. For example, an effective dose of a composition comprising a PPARδ iRNA agent can be administered to a patient once a month for an indefinite period of time, or until the patient no longer requires therapy. A person of ordinary skill in the art will recognize that the condition of the individual can be monitored throughout the course of treatment and that the effective amount of a composition comprising a PPARδ iRNA agent that is administered can be adjusted accordingly.

A composition comprising a PPARδ iRNA agent as disclosed in the present specification can also be administered to a patient in combination with other therapeutic compounds to increase the overall therapeutic effect of the treatment. The use of multiple compounds to treat an indication can increase the beneficial effects while reducing the presence of side effects.

The actual effective amount of a composition comprising a PPARδ iRNA agent to be administered to a patient can be determined by a person of ordinary skill in the art by taking into account factors, including, without limitation, the type of ocular disease, the location of the ocular disease, the cause of the ocular disease, the severity of the ocular disease, the degree of relief desired, the duration of relief desired, the particular PPARδ iRNA agent used, the rate of excretion of the PPARδ iRNA agent used, the pharmacodynamics of the PPARδ iRNA agent used, the nature of the other compounds to be included in the composition, the particular route of administration, the particular characteristics, history and risk factors of the patient, such as, e.g., age, weight, general health and the like, or any combination thereof. Additionally, where repeated administration of a composition comprising a PPARδ iRNA agent is used, the actual effect amount of a composition comprising a PPARδ iRNA agent will further depend upon factors, including, without limitation, the frequency of administration, the half-life of the composition comprising a PPARδ iRNA agent, or any combination thereof.

EXAMPLES

Example 1

Synthesis of a PPARδ iRNA Agent

This example illustrates how to make a PPARδ iRNA agent.

To synthesis a PPARδ iRNA agent, polynucleotide molecule comprising SEQ ID NO: 50, SEQ ID NO: 52 or SEQ ID NO: 58 are synthesized using standard procedures, see, e.g., Thompson et al., supra, (2004); Baker, supra, (2006); De Fourgerolles et al, supra, (2006); McSwiggen et al., supra, (2006); Soutschek et al., supra, (2006); and Vargeese et al., supra, (2006), each of which is herein incorporated by reference in its entirety. In general, polynucleotide molecules are made using a synthesizer which is basically a computer-controlled reagent delivery system. The first base is attached to a solid support, usually a glass or polystyrene bead, which is designed to anchor the growing polynucleotide molecule chain in the reaction column. Synthesis of a polynucleotide molecule consists of cyclic series of chemical reactions where an additional base is incorporated by each cycle. A polynucleotide molecule is built by repeating the synthesis cycles until the desired length is achieved.

A similar procedure can be used to synthesis PPARδ iRNA agents comprising SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 53, SEQ ID NO: 54, SEQ ID NO: 55. SEQ ID NO: 56, SEQ ID NO: 57, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71 and SEQ ID NO: 72.

Example 2

Quantitative PCR Assay

This example illustrates how to test a PPARδ iRNA agent to determine the effectiveness of the agent in reducing PPARδ expression.

To determine the effectiveness of a PPARδ iRNA agent in reducing PPARδ expression, a quantitative PCR assay was performed. ARPE-19 cells were plated in a 96 well plate at an approximate density of $1 \times 10^4$ cells per well in 100 µL of DMEM F12 medium containing 10% Fetal Bovine Serum (FBS), and 1% antimycotic, and were grown in a 37° C. incubator under 5% carbon dioxide overnight. The next day the cells were washed twice with DMEM F12 containing 0.1% FBS and 1% antibiotic antimycotic. After washing the cells were starved for 24 hours in the same media in a 37° C. incubator under 5% carbon dioxide. After 24 hours of starvation, tertiary-butylhydroperoxide (t-BH) was added to the media at the indicated concentrations for 3 hours or 6 hours. After t-BH incubation, the cells were then washed twice with DMEM F12 medium containing 0.1% FBS and 1% antibiotic antimycotic. After washing, fresh media was added and the cells and the cells were placed in a 37° C. incubator under 5% carbon dioxide for approximately 24 hours from the initial t-BH treatment until the cells reach an appropriate density for transfection.

To transfect a PPARδ iRNA agent into t-BH treated cells, a 3 mL transfection solution was prepared by adding 1.5 mL of OPTI-MEM Reduced Serum Medium containing 15 µL of LipofectAmine 2000 (Invitrogen, Carlsbad, Calif.) incubated at room temperature for 5 minutes to 1.5 mL of OPTI-MEM Reduced Serum Medium containing 167 nM of a PPARδ iRNA agent or control oligonucleotide. The PPARδ iRNA agents used comprised SEQ ID NO: 50, SEQ ID NO: 52 and SEQ ID NO: 58. This transfection was incubated at room temperature for approximately 20 minutes. The complete, supplemented cell culture media is replaced with 7 mL of OPTI-MEM Reduced Serum Medium and the 3 mL transfection solution is added to the cells and the cells are incubated in a 37° C. incubator under 5% carbon dioxide for approximately 16 hours. Transfection media is replaced with 10 mL of fresh complete, supplemented cell culture media and the cells are incubated in a 37° C. incubator under 5% carbon dioxide for approximately 24 hours.

To assay for the level of PPARδ expression, transfected cells were harvested either 72 hours or 9 days post-transfection by being washed once with PBS, lysed with Qiazol (QIAGEN, Inc., Valencia, Calif.) and scraped into 2 ml tubes. Approximately 200 μL of chloroform per ml of Qiazol was then added, the tubes mixed and spun (12000 g) for 15 minutes at 4° C. The aqueous phase was removed and applied to an RNeasy mini column (QIAGEN, Inc., Valencia, Calif.), washed and eluted in water. 1-5 μg of RNA was used for subsequent RT-PCR reactions. RT-PCR reactions were carried out using the Invitrogen Superscript III First Strand Synthesis System (Invitrogen, Carlsbad, Calif.). RT reactions were incubated at 25° C. for 10 minutes and then incubated at 42° C. for 50 minutes. The reaction was terminated by incubating at 85° C. for 5 minutes. Quantitative PCR was conducted using 5 μL of cDNA generated by RT-PCR. Platinum qPCR Supermix-UDG assay (Invitrogen, Carlsbad, Calif.) was used for the amplification. The PCR reaction was carried out for 45 cycles using the following conditions: 50° C. for 2 minutes, 95° C. for 2 minutes, then 45 cycles comprising 95° C. for 15 seconds, 55° C. for 30 seconds and 72° C. for 30 seconds. GAPDH expression was used as a control to normalize expression levels. Reactions and analysis were carried out using an ABI Prism 7700 Sequence Detector. FIG. 1 shows inhibition of PPARδ expression by specific siRNA. PPARδ iRNA agents designed to inhibit PPARδ expression were transfected into ARPE-19 cells at a final concentration of 25 nM. Cells were harvested 72 hours and 9 days post-transfection and RNA isolated. Quantitative PCR was conducted using GAPDH to normalize expression levels. RNA levels are expressed as percent of control (untransfected cells). All PPARδ iRNA agents used demonstrated a significant reduction in PPARδ RNA expression.

A similar quantitative PCR assay can be used to test PPARδ iRNA agents comprising SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 53, SEQ ID NO: 54, SEQ ID NO: 55. SEQ ID NO: 56, SEQ ID NO: 57, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71 and SEQ ID NO: 72.

Example 3

Oxidative Stress Assay

This example illustrates how to test whether reduction of PPARδ expression by a PPARδ iRNA agent results in protection from oxidative damage.

To determine whether reduction of PPARδ expression by a PPARδ iRNA agent results in protection from oxidative damage, an oxidative stress assay was performed. ARPE-19 cells were plated in a 96 well plate at an approximate density of $1 \times 10^4$ cells per well in 100 μL of DMEM F12 medium containing 10% Fetal Bovine Serum (FBS), and 1% antimycotic, and were grown in a 37° C. incubator under 5% carbon dioxide overnight. The next day the cells were washed twice with DMEM F12 containing 0.1% FBS and 1% antibiotic antimycotic. After washing the cells were starved for 24 hours in the same media in a 37° C. incubator under 5% carbon dioxide. After 24 hours of starvation, tertiary-butylhydroperoxide (t-BH) was added to the media at the indicated concentrations for 3 hours or 6 hours. After t-BH incubation, the cells were then washed twice with DMEM F12 medium containing 0.1% FBS and 1% antibiotic antimycotic. After washing, fresh media was added and the cells and the cells were placed in a 37° C. incubator under 5% carbon dioxide for approximately 24 hours from the initial t-BH treatment until the cells reach an appropriate density for transfection.

To transfect a PPARδ iRNA agent into t-BH treated cells, a 3 mL transfection solution was prepared by adding 1.5 mL of OPTI-MEM Reduced Serum Medium containing 15 μL of LipofectAmine 2000 (Invitrogen, Carlsbad, Calif.) incubated at room temperature for 5 minutes to 1.5 mL of OPTI-MEM Reduced Serum Medium containing 167 nM of a PPARδ iRNA agent or control oligonucleotide. This transfection was incubated at room temperature for approximately 20 minutes. The complete, supplemented cell culture media is replaced with 7 mL of OPTI-MEM Reduced Serum Medium and the 3 mL transfection solution is added to the cells and the cells are incubated in a 37° C. incubator under 5% carbon dioxide for approximately 16 hours. Transfection media is replaced with 10 mL of fresh complete, supplemented cell culture media and the cells are incubated in a 37° C. incubator under 5% carbon dioxide for approximately 24 hours.

Figure 2A:
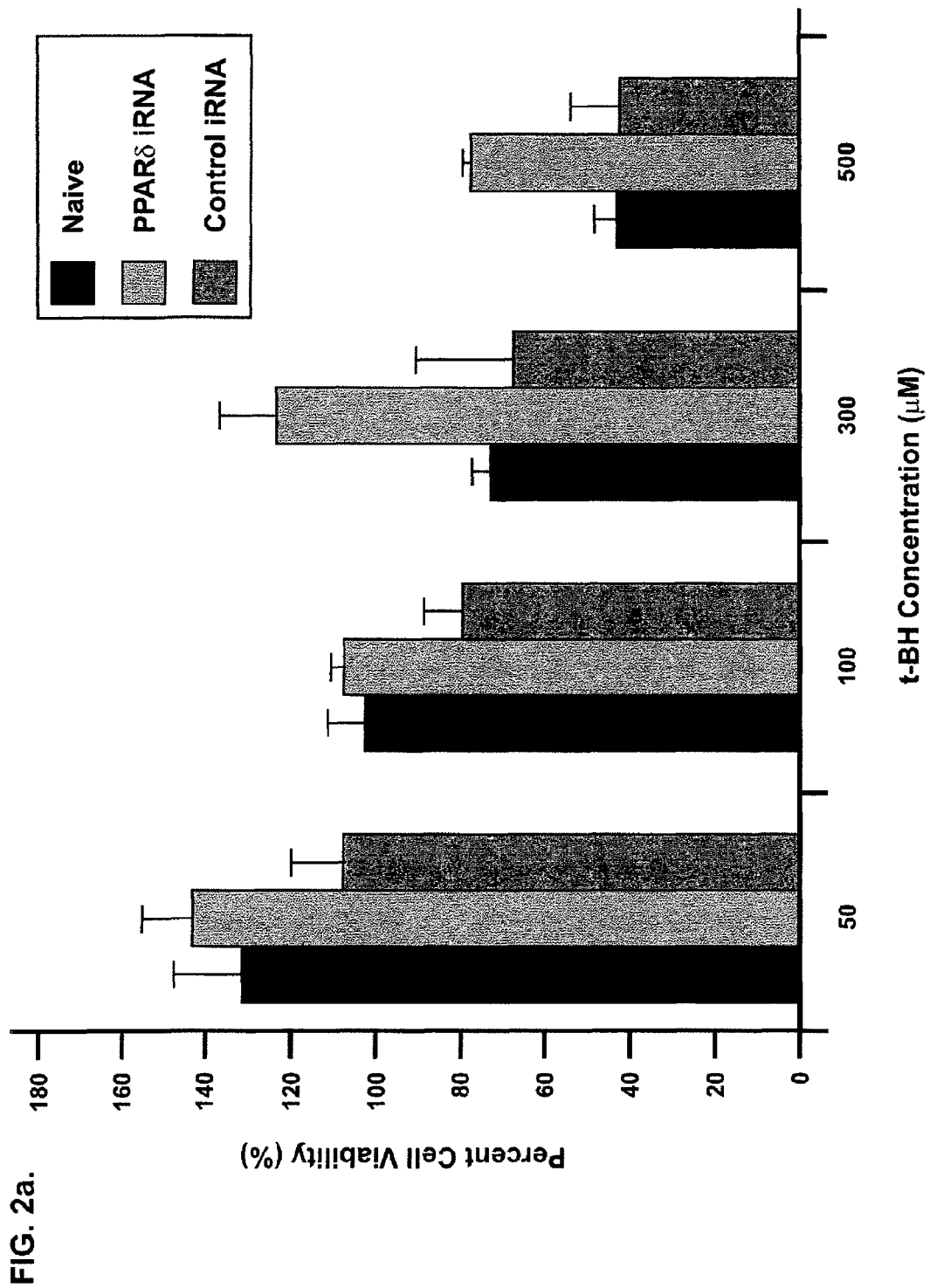
FIG. 2 shows reduction of PPARδ expression blocks cell death induced by reactive oxygen species. A WST assay was conducted 24 hrs after exposure to t-BH for 3 hours (FIG. 2a) or 6 hours (FIG. 2b) on naïve ARPE-19 or ARPE-19 cells transfected with a PPARδ iRNA agent. Values are expressed as the percentage of control cell viability (untreated cells).
Figure 2B:
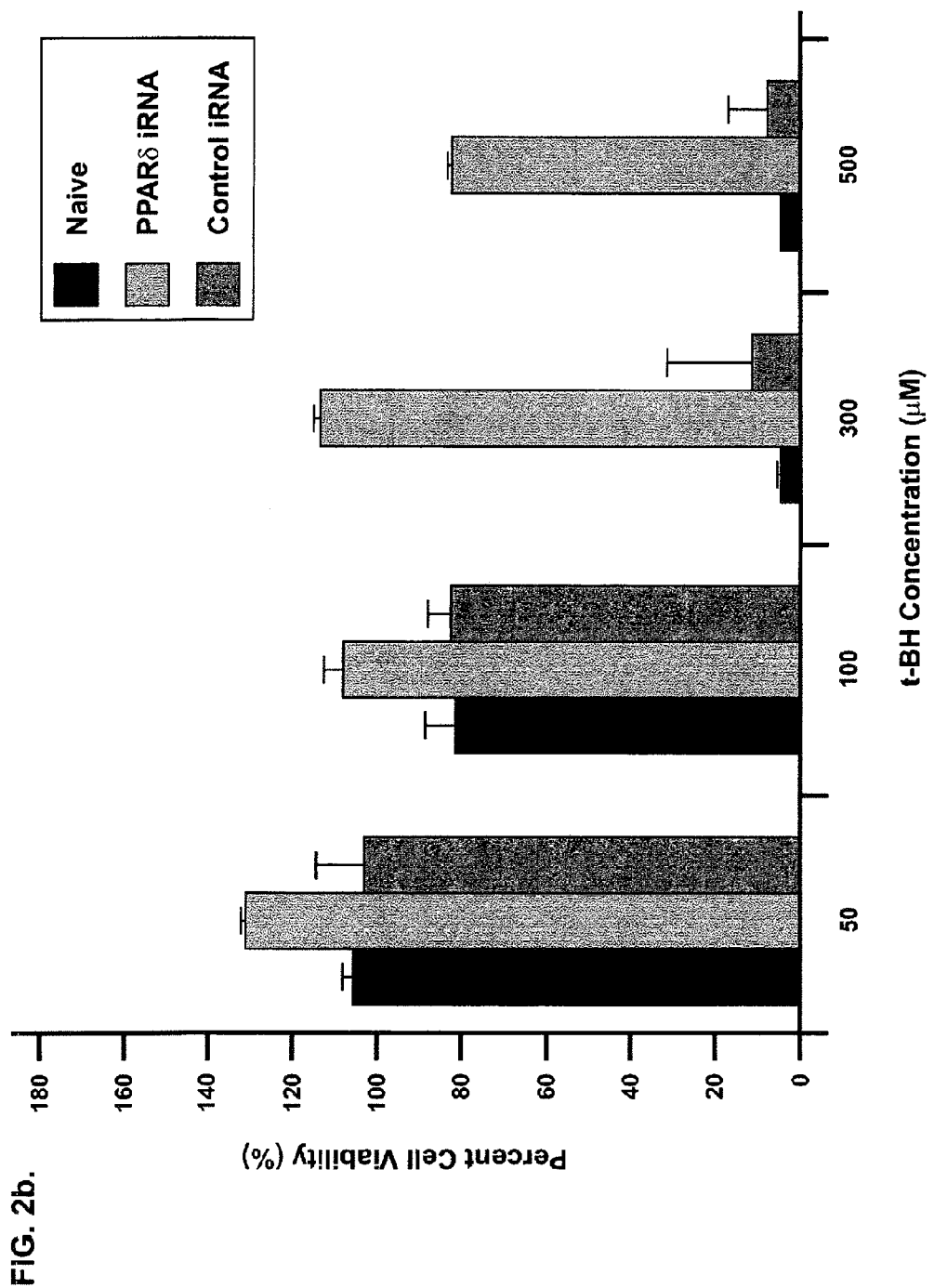

To assay for the level of cell viability, an ELISA-based Cell Proliferation Assay using WST dye was performed (Millipore Corp., Billerica, Mass.). Approximately 10 μL of WST-1/ ECS reagent was added to each well, incubated for 60 minutes and the absorbance of each sample was measured in a Spectramax M2 Platereader at 450 nm. FIG. 2 shows a reduction of PPARδ expression blocks cell death induced by reactive oxygen species.

A similar oxidative stress assay can be used to test PPARδ iRNA agents comprising SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 51, SEQ ID NO: 53, SEQ ID NO: 54, SEQ ID NO: 55. SEQ ID NO: 56, SEQ ID NO: 57, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71 and SEQ ID NO: 72.

Example 4

Treatment of Wet ARMD with a PPARδ iRNA Agent

The degradation of the RPE brought on by an unwanted PPARδ activity is observed in a 62-year-old woman diagnosed with wet age-related macular degeneration in the right eye. The physician decides to treat the patient with an intravitreal injection of 100 μL of a hyaluronic acid solution containing about 10 μg to about 100 μg of a PPARδ iRNA agent in suspension to the right eye of the patient. The eye is monitored weekly for 16 weeks. Within one month following administration the patient displays a two line improvement in visual acuity and an acceptable reduction in the rate of cell death in the RPE. The patient reports an overall improvement in quality of life.

A similar treatment regime can be successfully employed to effectively treat a patient suffering from other ocular disorders such as, e.g., dry Age-Related Macular Degeneration, Best's vitelliform macular degeneration, glaucoma, retinitis pigmentosa, diabetic retinopathy, macular edema, a degenerative disease of photoreceptors and a degenerative disease of the retinal pigment epithelium.

Example 5

Treatment of Macular Edema with a PPARδ iRNA Agent

A 58-year-old man is diagnosed with cystic macular edema brought on by an unwanted PPARδ activity. The man is treated by administration of a biodegradable drug delivery system administered to each eye of the patient. A 2-mg intraocular implant containing about 1000 μg of PLGA and about 1000 μg of PPARδ iRNA agent is delivered in his left eye by subconjunctival injection at a location that does not interfere with the man's vision. A similar or smaller implant is administered subconjunctivally to the patient's right eye. A more rapid reduction in retinal thickness in the right eye may occur due to the location of the implant and the activity of the PPARδ iRNA agent. The patient's visual acuity (and retinal condition under dilation) are monitored every two weeks. After about 3 months from the treatment, the patient's macular edema is seen to have largely subsided, a normal appearing retina is evident and visual acuity has increased by three lines in the left eye and 1 line in the right eye. Reduction in unwanted PPARδ activity indicates successful treatment with the PPARδ iRNA agent implant. One week after administration of the implant, an intraocular pressure that is similar to the pressure before the placement of the implant in the eye can be reflective of no apparent side effects associated with the implant.

A similar treatment regime can be successfully employed to effectively treat a patient suffering from other ocular disorders such as, e.g., wet Age-Related Macular Degeneration, dry Age-Related Macular Degeneration, Best's vitelliform macular degeneration, glaucoma, retinitis pigmentosa, diabetic retinopathy, a degenerative disease of photoreceptors and a degenerative disease of the retinal pigment epithelium.

Example 6

Treatment of Proliferative Diabetic Retinopathy with a PPARδ iRNA Agent

A 69 year old female complains of vision loss in the left eye. The patient reports an onset of Type II diabetes at age 40, and has been under treatment with metformin hydrochloride for 10 years. Retinal examination of the left eye under dilation reveals exudative neovascularization and apparent macular edema consistent with a diagnosis of proliferative diabetic retinopathy. The patient is given an intravitreal injection comprising 150 μl of a solution of hyaluronic acid in which biodegradable PLGA microspheres (mean particle diameter of about 40 μm; lactide to glycolide ratio 75:25) are suspended. Approximate weight of microspheres per dose was 20 mg. In addition to the PLGA polymer, the microspheres comprise approximately 2000 μg of PPARδ iRNA agent. The microparticles are formulated to release up to about 40% of PPARδ iRNA agent in the first few days, with a subsequent release of from about 1% to about 2% over the remaining life of the microspheres. The patient's visual acuity (and retinal condition under dilation) are monitored every two weeks for 8 weeks. At the end of this period of time, the patient's abnormal vascularization of the retina is seen to have largely subsided, while no new neovascularization is observed in the left eye. Fluorescein angiography reveals that hemorrhaging has been halted, and visual acuity has increased by three lines in the left eye.

A similar treatment regime can be successfully employed to effectively treat a patient suffering from other intraocular cell proliferation disorders such as, e.g., proliferative diabetic disease, ARMD, retinopathy of prematurity, proliferative vitreoretinopathy, retinal-choroidal anastomosis, retinal angiomatous proliferation, retinal vein occlusion, neovascular glaucoma, retinoblastoma and uveal melanoma.

The invention claimed is:

1. A method for treating wet age-related macular degeneration, the method comprising administering to a subject in need of such treatment an agent comprising a duplex region directed towards a PPARδ target sequence, the duplex region comprising:
   a) a sense sequence comprising a nucleic acid sequence identical to or substantially identical to the PPARδ target sequence, wherein the sense strand that is substantially identical to the PPARδ target sequence differs in identity from the PPARδ target sequence by no more than five nucleotides; and
   b) an anti-sense sequence comprising a nucleic acid sequence complementary to or substantially complementary to the PPARδ target sequence, wherein the anti-sense strand that is substantially complementary to the PPARδ target sequence differs in complementarity from the PPARδ target sequence by no more than five nucleotides;

wherein the method is effective in treating the wet age-related macular degeneration.

2. The method of claim 1, wherein the agent is a double-stranded PPARδ iRNA agent.

3. The method of claim 1, wherein the anti-sense sequence comprises a 3'-end overhang.

4. The method of claim 1, wherein the 3'-end overhang is 1, 2, or 3 nucleotides in length.

5. The method of claim 1, wherein the agent comprises a modification in the sense sequence, the anti-sense sequence, or both sense sequence and the anti-sense sequence.

6. The method of claim 1, wherein the location of the modification is on a 3'-end nucleotide, a 5'-end nucleotide, or both a 3'-end nucleotide and a 5'-end nucleotide.

7. A method for treating wet age-related macular degeneration, the method comprising administering to a subject in need of such treatment a PPARδ iRNA agent comprising a duplex region directed towards a PPARδ target sequence, the duplex region comprising a) a sense sequence comprising a nucleic acid sequence identical to or substantially identical to the PPARδ target sequence, wherein the sense strand that is substantially identical to the PPARδ target sequence differs in identity from the PPARδ target sequence by no more than five nucleotides; and
   b) an anti-sense sequence comprising a nucleic acid sequence complementary to or substantially complementary to the PPARδ target sequence, wherein the anti-sense strand that is substantially complementary to the PPARδ target sequence differs in complementarity from the PPARδ target sequence by no more than five nucleotides; and
   wherein the PPARδ target sequence is a nucleic acid sequence selected from the group consisting of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, and SEQ ID NO: 72, wherein the method is effective in treating the ocular disease.

8. The method of claim 1, wherein the PPARδ target sequence comprises the sequence of SEQ ID NO: 15.

* * * * *

```
                        SEQUENCE LISTING

<160> NUMBER OF SEQ ID NOS: 74

<210> SEQ ID NO 1
<211> LENGTH: 3734
<212> TYPE: RNA
<213> ORGANISM: Homo sapiens

<400> SEQUENCE: 1
gcggagcgug ugacgcugcg gccgccgcgg accuggggau uaaugggaaa aguuuuggca      60
ggagcgggag aauucugcgg agccugcggg acggcggcgg uggcgccgua ggcagccggg     120 acaguuugu acaguguuuu gggcaugcac gugauacuca cacaguggcu ucugcucacc     180
aacagaugaa gacagaugca ccaacgaggc ugaugggaac caccccuguag agguccaucu     240 gcguucagac ccagacgaug ccagagcuau gacugggccu gcaggugugg cgccgagggg     300
agaucagcca uggagcagcc acaggaggaa gccccugagg uccgggaaga ggaggagaaa     360
```

-continued

| | |
|---|---|
| gaggaagugg cagaggcaga aggagcccca gagcucaaug ggggaccaca gcaugcacuu | 420 |
| ccuuccagca gcuacacaga ccucucccgg agcuccucgc caccucacu gcuggaccaa | 480 |
| cugcagaugg gcugugacgg ggccucaugc ggcagccuca acauggagug ccggugugc | 540 |
| ggggacaagg caucgggcuu ccacuacggu guucaugcau gugagggug caagggcuuc | 600 |
| uuccgucgua cgauccgcau gaagcuggag uacgagaagu gugagcgcag cugcaagauu | 660 |
| cagaagaaga accgcaacaa gugccaguac ugccgcuucc agaagugccu ggcacugggc | 720 |
| augucacaca acgcuauccg uuuggucgg augccggagg cugagaagag gaagcugguu | 780 |
| gcagggcuga cugcaaacga ggggagccag uacaacccac agguggccga ccugaaggcc | 840 |
| uucuccaagc acaucuacaa ugccuaccug aaaaacuuca acaugaccaa aaagaaggcc | 900 |
| cgcagcaucc ucaccggcaa agccagccac acggcgcccu uugugaucca cgacaucgag | 960 |
| acauugugc aggcagagaa ggggcuggug uggaagcagu uggugaaugg ccugccuccc | 1020 |
| uacaaggaga ucagcgugca cgucuucuac cgcugccagu gcaccacagu ggagaccgug | 1080 |
| cgggagcuca cugaguucgc caagagcauc cccagcuuca gcagccucuu ccucaacgac | 1140 |
| cagguuaccc uucucaagua uggcgugcac gaggccaucu cgccaugcu ggccucuauc | 1200 |
| gucaacaagg acgggcugcu gguagccaac ggcaguggcu uguucacccg ugaguccug | 1260 |
| cgcagccucc gcaaacccuu cagugauauc auugagccua aguuugaauu ugcugucaag | 1320 |
| uucaacgccc uggaacuuga ugacagugac cuggcccuau ucauugcggc caucauucug | 1380 |
| ugggagacc ggccaggccu caugaacguu ccacggguugg aggcuauucca ggacaccauc | 1440 |
| cugcgugccc ucgaauucca ccugcaggcc aaccacccug augcccagua ccucuucccc | 1500 |
| aagcugcugc agaagauggc ugaccugcgg caacugguca ccgagcacgc ccagaugaug | 1560 |
| cagcggauca agaagaccga aaccgagacc ucgcugcacc cucugcucca ggagaucuac | 1620 |
| aaggacaugu acuaacggcg gcacccaggc cucccugcag acccaaugg ggccagcacu | 1680 |
| ggaggggccc acccacauga cuuuuccauu gaccagcccu ugagcacccg gccuggagca | 1740 |
| gcagagucc acgaucgccc ucagacacau gacacccacg gccucuggcu cccugugccc | 1800 |
| ucucucccgc uuccuccagc cagcucucuu ccugucuuug uugucccccu cuuucucagu | 1860 |
| uccucuuucu uuucuaauuc cuguugcucu guuucuuccu uucuguaggu uucucucuuc | 1920 |
| ccuucuccccu ugcccucccu uucucucucc accccccacg ucugccucc uuucuuauuc | 1980 |
| ugugagaugu uuuguauuau uucaccagca gcauagaaca ggaccucugc uuuugcacac | 2040 |
| cuuuccccca ggagcagaag agagugggc cugcccucug ccccaucauu gcaccugcag | 2100 |
| gcuuaggucc ucacuucugu cuccugucuu cagagcaaaa acuugagcc auccaaagaa | 2160 |
| acacuaagcu cucugggccu ggguuccagg gaaggcuaag cauggccugg acugacugca | 2220 |
| gcccccuaua gucauggggu cccugcugca aaggacagug ggcaggaggc cccaggcuga | 2280 |
| gagccagaug ccuccccaag acugucauug ccccuccgau gcugaggcca cccacugacc | 2340 |
| caacugaucc ugcuccagca gcacaccuca gccccacuga cacccagugu ccuuccaucu | 2400 |
| ucacacuggu uugccaggcc aauguugcug auggcccccu gcacuggccg cuggacggca | 2460 |
| cucucccagc uuggaaguag gcagggucc cuccaggugg gccccaccu cacugaagag | 2520 |
| gagcaagucu caagagaagg aggggggauu ggugguugga ggaagcagca cacccaauuc | 2580 |
| ugccccuagg acucgggguc ugaguccugg ggucaggcca gggagagcuc ggggcaggcc | 2640 |
| uuccgccagc acucccacug cccccccgcc caguagcagc cgcccacauu gugucagcau | 2700 |
| ccagggccag ggccuggccu cacaucccc ugcuccuuc ucuagcuggc uccacgggag | 2760 |

| | |
|---|---|
| uucaggcccc acucccccug aagcugcccc uccagcacac acacauaagc acugaaauca | 2820 |
| cuuuaccugc aggcuccaug caccucccuu cccucccuga ggcagguagag aacccagaga | 2880 |
| gaggggccug caggugagca ggcagggcug ggccaggucu ccggggaggc aggguccug | 2940 |
| cagguccugu ugggucagcc cagcaccugc ucccagugg agcuucccgg gauaaacuga | 3000 |
| gccuguucau ucugaugucc auuuguccca auagcucuac ugcccucccc uuccccuuua | 3060 |
| cucagcccag cuggccaccu agaagucccc ugcacagcc ucuagugucc ggggaccuug | 3120 |
| ugggaccagu cccacaccgc ugguccugc ccuccccugc ucccagguug aggugcgcuc | 3180 |
| accucagagc agggccaaag cacagcuggg caugccaugu cugagcggcg cagagcccuc | 3240 |
| caggccugca ggggcaaggg gcuggcugga gucucagagc acagagguag gagaacuggg | 3300 |
| guucaagccc aggcuuccug gguccugccu ggucucccu cccaaggagc cauucugugu | 3360 |
| gugacucugg guggaagugc ccagccccug ccccuacggg cgcugcagcc ucccuuccau | 3420 |
| gccccaggau cacucucugc uggcaggauu cuuccgcuc ccaccuacc cagcugaugg | 3480 |
| ggguuggggu gcuuccuuuc aggccaaggc uaugaaggga cagcugcugg gacccaccuc | 3540 |
| cccccucccg gccacaugcc gcgucccugc cccgacccgg gucugguugcu gaggauacag | 3600 |
| cucuucucag ugucugaaca aucccaaaa uugaaaugua uauuuugcu aggagcccca | 3660 |
| gcuuccugug uuuuuaauau aaauaguga cacagacuga cgaaacuuua aauaauggg | 3720 |
| aauuaaauau uuaa | 3734 |

<210> SEQ ID NO 2
<211> LENGTH: 3725
<212> TYPE: RNA
<213> ORGANISM: Homo sapiens

<400> SEQUENCE: 2

| | |
|---|---|
| gugugacgcu gcggccgccg cggaccuggg gauuaauggg aaaaguuuug gcaggagcgg | 60 |
| gagaauucug cggagccugc gggacggcgg cgguggcgcc uaggcagcc gggacagugu | 120 |
| uguacagugu uuugggcaug cacgugauac ucacacagug gcuucugcuc accaacagau | 180 |
| gaagacagau gcaccaacga ggcugauggg aaccacccug uagaggucca ucugcguuca | 240 |
| gacccagacg augccagagc uaugacuggg ccugcaggug uggcgccgag gggagaucag | 300 |
| ccauggagca gccacaggag gaagcccug aggugccggga agaggaggag aaagaggaag | 360 |
| uggcagaggc agaaggagcc ccagagcuca auggggacc acagcaugca cuuccuucca | 420 |
| gcagcuacac agaccucucc cggagcuccu cgccacccuc acugcuggac caacugcaga | 480 |
| ugggcuguga cggggccuca ugcggcagcc ucaacaugga gugccgggug gcggggaca | 540 |
| aggcaucggu cuuccacuac ggguucaug caugugaggg gugcaagggc uucuuccguc | 600 |
| guacgauccg caugaagcug gaguacgaga gugugagcg cagcugcaag auucagaaga | 660 |
| agaaccgcaa caagccag acugccgcu ccagaagug ccuggcacug gcaugucac | 720 |
| acaacgcuau ccguuuuggu cggaugccgg aggcugagaa aggaagcug guggcagggc | 780 |
| ugacugcaaa cgaggggagc caguacaacc cacaggugg cgaccugaag gccuucucca | 840 |
| agcacaucua caaugccuac cugaaaaacu caacaugac caaaaagaag gcccgcagca | 900 |
| uccucaccgg caaagccagc cacacggcgc ccuuugugau ccgacaucau gagacauugu | 960 |
| ggcaggcaga aagggggcug gugugguggaagc aguugguga uggccugccu cccuacaagg | 1020 |
| agaucagcgu gcacgucuuc uaccgcugcc agucaccac aguggagacc gugcgggagc | 1080 |
| ucacugaguu cgccaagagc aucccagcu ucagcagccu cuuccucaac gaccagguua | 1140 |

```
cccuucucaa guauggcgug cacgaggcca ucuucgccau gcuggccucu aucgucaaca    1200
aggacgggcu gcugguagcc aacggcagug gcuuugucac ccgugaguuc cugcgcagcc    1260
uccgcaaacc cuucagugau aucauugagc cuaaguuuga auuugcuguc aaguucaacg    1320
cccuggaacu ugaugacagu gaccuggccc uauucauugc ggccaucauu cuguguggag    1380
accggccagg ccucaugaac guuccacggg uggaggcuau ccaggacacc auccugcgug    1440
cccucgaauu ccaccugcag gccaaccacc cugaugccca guaccucuuc cccaagcugc    1500
ugcagaagau ggcugaccug cggcaacugg ucaccgagca cgcccagaug augcagcgga    1560
ucaagaagac cgaaaccgag accucgcugc acccucugcu ccaggagauc uacaaggaca    1620
uguacuaacg gcggcaccca ggccucccug cagacuccaa uggggccagc acuggagggg    1680
cccacccaca ugacuuuucc auugaccagc ccuugagcac ccggccugga gcagcagagu    1740
cccacgaucg cccucagaca caugacaccc acggccucug gcucccugug cccucucucc    1800
cgcuuccucc agccagcucu cuuccugucu uguugucuc ccucuuucuc aguccucuu     1860 ucuuuucuaa uuccuguugc ucuguuucuu ccuucugua gguucucuc uucccuucuc     1920 ccuugcccuc ccuuucucuc uccaccccc acgucuguc uccuuucuua uucgugaga     1980 uguuuuguau uauuucacca gcagcauaga acaggaccuc ugcuuuugca caccuuuucc    2040
ccaggagcag aagagagugg ggccugcccu cugccccauc auugcaccug caggcuuagg    2100
uccucacuuc ugucuccugu cuucagagca aaagacuuga gccauccaaa gaaacacuaa    2160
gcucucuggg ccugguuccc agggaaggcu aagcauggcc uggacugacu gcagccccu     2220 auagucaugg ggucccugcu gcaaaggaca guggcagga ggcccaggc ugagagccag      2280 augccucccc aagacuguca uugccccucc gaugcugagg ccaccacugu acccaacuga    2340
uccugcucca gcagcacacc ucagcccac ugacacccag ugccuucca ucuucacacu     2400 gguuugccag gccaauguug cugauggcc ccugcacugg ccgcuggacg cacucucccc    2460
agcuuggaag uaggcagggu ucccuccagg ugggccccca ccucacugaa gaggagcaag    2520
ucucaagaga aggagggggg auugguggu ggaggaagca gcacacccaa uucugccccu    2580
aggacucggg gucugagucc uggggucagg ccagggagag cucggggcag gccuuccgcc    2640
agcacuccca cugccccccu gcccaguagc agccgccac auugugucag cauccagggc    2700
cagggccugg ccucacaucc cccugcuccu uucucuagcu ggcuccacgg gaguucaggc    2760
cccacucccc cugaagcugc cccuccagca cacacacaua agcacugaaa ucacuuuacc    2820
ugcaggcucc augcacccuc cuucccuccc ugaggcaggu gagaacccag agagagggc     2880 cugcagguga gcaggcaggg cugggccagg ucuccgggga ggcagggguc cugcaggucc    2940
ugguggguca gcccagcacc ugcucccagu gggagcuucc cgggauaaac ugagccuguu    3000
cauucugaug uccauuuguc ccaauagcuc uacugcccuc cccuucccu uuacucagcc    3060 cagcuggcca ccuagaaguc uccugcaca gccucuagug uccggggacc uuguggacc     3120 aguccoacac cgcugguccc ugcccucccc ugcucccagg uugaggugcg cucaccucag    3180
agcagggcca aagcacagcu gggcaugcca ugucugagcg gcgcagagcc uccaggccu     3240 gcagggcaa ggggcuggcu ggagucucag agcacagagg uaggagaacu ggggxxcaag     3300 cccaggcuuc cuggguccug ccugguccuc ccucccaagg agccauucug ugugugacuc    3360
uggguggaag ugcccagccc cugcccuac gggcgcugca gccucccuuc caugcccag     3420 gaucacucuc ugcuggcagg auucuucccg cuccccaccu acccagcuga uggggguugg    3480
ggugcuuccu uucaggccaa ggcuaugaag ggacagcugc ugggacccac cucccccucc    3540
```

-continued

| | |
|---|---|
| ccggccacau gccgcguccc ugccccgacc cgggucuggu gcugaggaua cagcucuucu | 3600 |
| cagugucuga acaaucucca aaauugaaau guauauuuuu gcuaggagcc ccagcuuccu | 3660 |
| guguuuuuaa uauaaauagu guacacagac ugacgaaacu uuaaauaaau gggaauuaaa | 3720 |
| uauuu | 3725 |

<210> SEQ ID NO 3
<211> LENGTH: 2635
<212> TYPE: RNA
<213> ORGANISM: Homo sapiens

<400> SEQUENCE: 3

| | |
|---|---|
| gccucacagg cagacacagg auuugaauua agcauugagu cucuuaacca caauacuacg | 60 |
| uugccuaauc ggggggagg uggggacaaa uuggcaaaaa acaaaagaag uggauuaaga | 120 |
| ccagggguag ggagauuaga acacccagug gagcauugcu gaugggacag ggcuuggucu | 180 |
| gucacggcca aggaggccug ccguccccug gccaaguca ccucuugggg uggaaguagg | 240 |
| ggagcuccac ugccuuucug agcucccugg cgugcccugu gucccacag accggccagg | 300 |
| ccucaugaac guuccacggg uggaggcuau ccaggacacc auccgcgug cccucgaauu | 360 |
| ccaccugcag gccaaccacc cugaugccca guaccucuuc cccaagcugc ugcagaagau | 420 |
| ggcugaccug cggcaacugg ucaccgagca cgcccagaug augcagcgga ucaagaagac | 480 |
| cgaaaccgag accucgcugc acccucugcu ccaggagauc uacaaggaca guacuaacg | 540 |
| gcggcaccca ggccucccug cagacuccaa ugggggcagc acuggagggg cccacccaca | 600 |
| ugacuuuucc auugaccagc ccuugagcac ccggccugga gcagcagagu cccacgaucg | 660 |
| cccucagaca caugcacccc acggccucug gcucccugug cccucucucc cgcuuccucc | 720 |
| agccagcucu cuuccugucu uuguugcuc ccucuuucu aguccucuu ucuuuucuaa | 780 |
| uccuguugc ucuguuucu ccuuucugua ggguucucuc uucccuucuc ccuugcccuc | 840 |
| ccuuucucuc uccaccccc acgucugucc uccuuucuua uucugugaga uguuugau | 900 |
| uauuucacca gcagcauaga acaggaccuc ugcuuuugca caccuuuucc ccaggagcag | 960 |
| aagagagugg ggccugcccu cugccccauc auugcaccug caggcuuagg uccucacuuc | 1020 |
| ugucuccugu cuucagagca aaagacuuga gccauccaaa gaaacacuaa gcucucuggg | 1080 |
| ccuggguucc agggaaggcu aagcauggcc uggacugacu gcagccccu auagucaugg | 1140 |
| gguccugcu gcaaaggaca gugggcagga ggcccaggc ugagagccag augccucccc | 1200 |
| aagacuguca uugcccuccc gaugcugagg ccacccacug acccaacuga uccgcuccca | 1260 |
| gcagcacacc ucagccccac ugacacccag uguccuucca ucuucacacu gguuugccag | 1320 |
| gccaauguug cugauggccc ccugcacugg ccgcuggacg gcacucuccc agcuggaag | 1380 |
| uaggcagggu ucccuccagg uggggcccca ccucacugaa gaggagcaag ucucaagaga | 1440 |
| aggagggggg auuggugguu ggaggaagca gcacacccaa uucugcccu aggacucggg | 1500 |
| gucugaguCC uggggucagg ccagggagag cucggggcag gccuuccgcc agcacuccca | 1560 |
| cugccccccu gccaguagc agccgccac auugugucag cauccagggc cagggccugg | 1620 |
| ccucacaucc cccugcuccu uucucuagcu ggcuccacgg gaguucaggc cccacuccCc | 1680 |
| cugaagcugc ccuccagca cacacacaua agcacugaaa ucacuuuacc ugcaggcucc | 1740 |
| augcacccuc cuucccuccc ugaggcaggu gagaacccag agagagggc cugcagguga | 1800 |
| gcaggcaggg cugggccagg ucuccgggga ggcagggguc cugcaggucc ugguggguca | 1860 |
| gcccagcacc ugcucccagu gggagcuucc cgggauaaac ugagccuguu cauucugaug | 1920 |

| | |
|---|---|
| uccauuuguc ccaauagcuc uacugcccuc cccuucccu uuacucagcc cagcuggcca | 1980 |
| ccuagaaguc ucccugcaca gccucuagug uccggggacc uugugggacc agucccacac | 2040 |
| cgcuggucc ugcccuccc ugcucccagg uugaggugcg cucaccucag agcagggcca | 2100 |
| aagcacagcu gggcaugcca ugucugagcg gcgcagagcc uccaggccu gcaggggcaa | 2160 |
| ggggcuggcu ggagucucag agcacagagg uaggagaacu ggguucaag cccaggcuuc | 2220 |
| cuggguccug ccuggccuc ccucccaagg agccauucug ugugacucu uggguggaag | 2280 |
| ugcccagccc cugcccuac gggcgcugca gccucccuuc caugcccag gaucacucuc | 2340 |
| ugcuggcagg auucuucccg cucccaccu acccagcuga uggggguugg ggugcuuccu | 2400 |
| uucaggccaa ggcuaugaag ggacagcugc ugggacccac cuccccuc ccggccacau | 2460 |
| gccgcguccc ugcccgacc cgggucuggu gcugaggaua cagcucuucu cagugucuga | 2520 |
| acaaucucca aaauugaaau guauauuuu gcuaggagcc ccagcuuccu uguuuuuaa | 2580 |
| uauaaauagu guacacagac ugacgaaacu uuaaauaaau gggaauuaaa uauuu | 2635 |

<210> SEQ ID NO 4
<211> LENGTH: 3301
<212> TYPE: RNA
<213> ORGANISM: Homo sapiens
<220> FEATURE:
<221> NAME/KEY: unsure
<222> LOCATION: (2966)...(2972)
<223> OTHER INFORMATION: n is any ribonucleic acid.

<400> SEQUENCE: 4

| | |
|---|---|
| gaauucugcg gagccugcgg gacggcggcg gguuggcccg uaggcagccg ggacaguguu | 60 |
| guacaguguu uugggcaugc acgugauacu cacacagugg cuucugcuca ccaacagaug | 120 |
| aagacagaug caccaacgag ggucuggaau ggucuggagu ggucuggaaa gcagggucag | 180 |
| auaccccugg aaaacugaag cccguggagc aaugaucucu acaggacugc uucaaggcug | 240 |
| augggaacca cccuguagag guccaucugc guucagaccc agacgaugcc agagcuauga | 300 |
| cuggggccugc aggguguggcg ccgaggggag aucagccaug gagcagccac aggaggaagc | 360 |
| cccugagguc cgggaagagg aggagaaaga ggaaguggca gaggcagaag gagccccaga | 420 |
| gcucaauggg ggaccacagc augcacuucc uuccagcagc uacacagacc ucucccggag | 480 |
| cuccucgcca cccucacugc uggaccaacu gcagauggg ugugacgggg ccucaugcgg | 540 |
| cagccucaac augggagugcc gggugugcgg ggacaaggca ucgggcuucc acuacggugu | 600 |
| ucaugcaugu gagggggugca agggcuucuu ccgucguacg auccgcauga agcuggagua | 660 |
| cgagaagugu gagcgcagcu gcaagauuca aagaagaac cgcaacaagu gccaguacug | 720 |
| ccgcuuccag aagugccugg cacugggcau gucacacaac gcuauccguu uggucggau | 780 |
| gccggaggcu gagaagagga agcugguggc agggcugacu gcaaacgagg ggagccagua | 840 |
| caacccacag guggccgacc ugaaggccuu uccaagcac aucuacaaug ccuaccugaa | 900 |
| aaacuucaac augaccaaaa agaaggcccg cagcauccuc accggcaaag ccagccacac | 960 |
| ggcgcccuuu ugauccacg acaucgagac auuguggcag gcagagaagg ggcugguguag | 1020 |
| gaagcaguug gugaauggcc ugccuccccua caaggagauc agcgugcacg ucuucuaccg | 1080 |
| cugccagugc accacaguggg agaccgugcg ggagcucacu gaguucgcca agagcauccc | 1140 |
| cagcuucagc agccucuucc ucaacgacca gguuacccuu cucaaguaug cgugcacga | 1200 |
| ggccaucuuc gccaugcugg ccucuaucgu caacaaggac gggcugcugg uagccaacgg | 1260 |
| cagugggcuuu gucacccgug aguccugcg cagccuccgc aaacccuuca gugauaucau | 1320 |

```
ugagccuaag uuugaauuug cugucaaguu caacgcccug gaacuugaug acagugaccu   1380
ggcccuauuc auugcggcca ucauucugug uggagaccgg ccaggccuca ugaacguucc   1440
acgggugagg gcuauccagg acaccauccu gcgugcccuc gaauuccacc ugcaggccaa   1500
ccacccugau gcccaguacc ucuucccaa gcugcugcag aagauggcug accugcggca    1560
acuggucacc gagcacgccc agaugaugca gcggaucaag aagaccgaaa ccgagaccuc   1620
gcugcacccu cugcuccagg agaucuacaa ggacauguac uaacggcggc acccaggccu   1680
cccugcagac uccaauggg ccagcacugg aggggcccac ccacaugacu uuccauuga    1740
ccagcucucu uccugucuuu guugucuccc ucuuucucag uuccucuuuc uuuucuaauu   1800
ccguugcuc uguucuucc uuucuguagg uuucucucuu cccucucccc uucucccuug    1860
cccucccuuu cucucuccua uccccacguc ugucccuccuu ucuuauucug ugagauguuu  1920
uguauuauuu caccagcagc auagaacagg accucugcuu uugcacaccu uuccccagg    1980
agcagaagag aguggccug cccucugccc caucauugca ccugcaggcu uaggucuca    2040
cuucugucuc cugucuucag agcaaaagac uugagccauc caagaaaca cuaagcucuc    2100
uggccuggg uucagggaa ggcuaagcau ggccuggacu gacugcagcc cccuauaguc     2160
auggggucc ugcugcaaag gacaguggca gaccccggca guagagccga gaugccuccc   2220
caagacuguc auugcccuc cgaucgugag gccaccacu gacccaauga uccucuccag    2280
cagcacaccu cagccccacu gacacccagu guccuuccau cuucacacug guugccagg    2340
ccaauguugc ugauggcccc uccagcacac acacauaagc acugaaauca cuuuaccugc   2400
aggcaccaug caccucccuu cccucccuga ggcaggugaa acccagaga gaggggccug    2460
caggugagca ggcagggcug ggccaggucu ccggggaggc aggggccug caggucccugg  2520
uggucagcc cagcaccucg cccagugggga gcuuccgggg auaaacugag ccuguucauu   2580
cugauugcca uuugucccaa uagcucuacu gcccucccu uccccuuuac ucagcccagc    2640
uggccaccua gaagucuccc ugcacagccu cuagugccg ggaccuugu gggaccaguc     2700
ccacaccgcu ggucccugcc cucccccgcu cccagguuga ggugcgcuca ccucagagca   2760
gggccaaagc acagcugggc augccaugc ugagcggcgc agagccucc aggccugcag     2820
gggcaagggg cuggcuggag ucucagagca cagagguagg agaacugggg uucaagccca   2880
ggcuuccugg guccugccug guccucccuc ccaaggagcc auucuaugug acucuggggu   2940
gaagugccca gccccugccu gacggnnnnn nngaucacuc ucugcuggca ggauucuucc   3000
cgcuccccac cuaccagcu gauggggguu gggugcuuc uuucagccaa ggcuaugaag    3060
ggacagcugc ugggacccac cucccccuu ccccggccac augccgcguc ccugccccca    3120
cccgggucug gugcugagga uacagcucuu cucagugucu gaacaaucuc caaaauugaa   3180
auguauauuu uugcuaggag ccccagcuuc cuguguuuuu aauauaaaua guguacacag   3240
acugacgaaa cuuuaaauaa augggaauua aauauuaaa aaaaaagcg gccgcgaauu     3300
c                                                                   3301
```

<210> SEQ ID NO 5
<211> LENGTH: 1960
<212> TYPE: RNA
<213> ORGANISM: Homo sapiens

<400> SEQUENCE: 5

```
guuuggcag gagcgggaga auucugcgga gccugcggga cggcggcggu ggcgccguag     60
gcagccggga caguguugua caguguuuug ggcaugcacg ugauacucac acagugggcuu  120
```

```
cugcucacca acagaugaag acagaugcac caacgaggcu gaugggaacc auccuguaga      180
gguccaucug cguucagacc cagacgaugc cagagcuaug acugggccug caggugyggc      240
gccgagggga gaucagccau ggagcagcca caggaggaag ccccgaggu ccgggaagag       300 gaggagaaag aggaagugc agaggcagaa ggagccccag agcucaaugg gggaccacag       360
caugcacuuc cuccagcag cuacacagac cucucccgga gcuccucgcc acccucacug       420
cuggaccaac ugcagauggg cugugacggg gccucaugcg gcagccucaa caugagugc       480 cggguguggg gggacaaggc aucgggcuuc cacuacgug uucaugcaug ugaggggugc       540
aagggcuucu ccgucguac gauccgcaug aagcuggagu acgagaagug ugagcgcagc       600
ugcaagauuc agaagaagaa ccgcaacaag ugccaguacu gccgcuucca gaagugccug      660
gcacugggca ugucacacaa cgcuauccgu uuuggucgga ugccggaggc ugagaagagg      720
aagcuggugg cagggcugac ugcaaaugag gggagccagu acaacccaca gguggccgac      780
cugaaggccu ucuccaagca caucuacaau gccuaccuga aaaacuucaa caugaccaaa      840
aagaaggccc gcagcauccu caccggcaaa gccagccaca cggcgcccuu ugugauccac      900
gacaucgaga cauuguggca ggcagagaag gggcuggugu ggaagcaguu ggugaauggc      960
cugccucccu acaaggagau cagcgugcac gucuucuacc gcugccagug caccacagug      1020
gagaccgugc gggagcucac ugaguucgcc aagagcaucc ccagcuucag cagcucuuc       1080 cucaacgacc agguuacccu ucucaaguau ggcgugcacg aggccaucuu cgccaugcug      1140 gcccucuaucg ucaacaagga cgggcugcug guagccaacg gcaguggcuu uguccaccgu      1200 gaguccugc gcagccuccg caaacccuuc agugauauca uugagccuaa guuugaauuu      1260
gcugucaagu ucaacgcccu ggaacuugau gacagugacc uggcccauau cauugcggcc      1320
aucauucugu guggagguga gugagagugg ggcaggugg cuggccuggc acacccaguc      1380
guccuggggg uuggcccuca cugcagggca cugugccuga gcucugacag gugggggaag      1440 ugcccugug aucuuggcag uggaacaugc aaggcacuga cugagcaugc aggaucagcu      1500
ccaucucauu auguacguag auagaggugg agacaggaaa aagacuaagc cagacguggu      1560
ggcucacacc uguaauccca gcacuuggc aggccgaggc ggguggauca cuugagguca      1620
ggaguucgaa accagccugg ccaacauggu gaaacccgu cucuacuaaa aauacaaaaa      1680
auuagccaga guggguggca cgcgccugua aucccagcua cuugggaggc ugagccagga      1740
gaaucgcuug aacccgaaag guggagguug cagugagcca aaaucccacc acugcacucc      1800
agccugggug acagagugag acccugcucu aaaaaaaaagg aaaaggacua acaggcagua      1860
ugcugucaug uuaaugugg guggaaaaau ugucugcauu uuuucugcau uuuuaaaauu       1920
ccaacccaau aaaaucaaua auaacuaugc uaaaaaaaaa                            1960
```

<210> SEQ ID NO 6
<211> LENGTH: 1953
<212> TYPE: RNA
<213> ORGANISM: Homo sapiens

<400> SEQUENCE: 6

```
guuuuggcag gagcgggaga auucugcgga gccugcggga cggcggcggu ggcgccguag       60
gcagccggga cagucuugua cagcuuuug ggcaugcacg ugauacucac acagugcuu        120 cugcucacca acagaugaag acagaugcac caacgaggcu gaugggaacc auccuguaga     180
gguccaucug cguucagacc cagacgaugc cagagcuaug acugggccug caggugyggc     240
gccgagggga gaucagccau ggagcagcca caggaggaag ccccgaggu ccgggaagag       300
```

-continued

| | |
|---|---|
| gaggagaaag aggaaguggc agaggcagaa ggagccccag agcucaaugg gggaccacag | 360 |
| caugcacuuc cuuccagcag cuacacagac cucucccgga gcuccucgcc acccucacug | 420 |
| cuggaccaac ugcagauggg cugugacggg gccucaugcg gcagccucaa cauggagugc | 480 |
| cgggugugcg gggacaaggc aucgggcuuc cacuacggug uucaugcaug ugaggggugc | 540 |
| aagggcuucu ccgucguac gauccgcaug aagcuggagu acgagaagug ugagcgcagc | 600 |
| ugcaagauuc agaagaagaa ccgcaacaag ugccaguacu gccgcuucca gaagugccug | 660 |
| gcacugggca ugucacacaa cgcuauccgu uuggucgga ugccggaggc ugagaagagg | 720 |
| aagcugguggg cagggcugac ugcaaaugag gggagccagu acaacccaca gguggccgac | 780 |
| cugaaggccu ucuccaagca caucuacaau gccuaccuga aaaacuucaa caugaccaaa | 840 |
| aagaaggccc gcagcauccu caccggcaaa gccagccaca cggcgcccuu ugugauccac | 900 |
| gacaucgaga cauuguggca ggcagagaag gggcuggugu ggaagcaguu ggugaauggc | 960 |
| cugccucccu acaaggagau cagcgugcac gucuucuacc gcugccagug caccacagug | 1020 |
| gagaccgugc gggagcucac ugaguucgcc aagagcaucc ccagcuucag cagccucuuc | 1080 |
| cucaacgacc agguuacccu ucucaaguau ggcgugcacg aggccaucuu cgccaugcug | 1140 |
| gccucuaucg ucaacaagga cgggcugcug guagccaacg gcaguggcuu ugucacccgu | 1200 |
| gaguccugc gcagccuccg caaacccuuc agugauauca uugagccuaa guuugaauuu | 1260 |
| gcugucaagu ucaacgcccu ggaacuugau gacagugacc uggcccuauu cauugcggcc | 1320 |
| aucauucugu guggaggug ugagagugg ggcagguggg cuggccuggc acacccaguc | 1380 |
| guccuggggg uuggcccuca cugcagggca cugugccuga gcucugacag uguggggaag | 1440 |
| ugcccugug aucuuggcag uggaacaugc aaggcacuga cugagcaugc aggaucagcu | 1500 |
| ccaucucauu auguacguag auagaggugg agacaggaaa aagacuaagc cagacguggu | 1560 |
| ggcucacacc uguaaucccca gcacuuggc aggccgaggc ggguggauca cuugagguca | 1620 |
| ggaguucgaa accagccugg ccaacauggu gaaaccccgu cucuacuaaa aaaucaaaaa | 1680 |
| auuagccaga gugguggca cgcgccugua aucccagcua cuugggaggc ugagccagga | 1740 |
| gaaucgcuug aacccgagag guggagguug caguagagcca aaaucccacc acugcacucc | 1800 |
| agccuggguug acagagugag acccugucuc aaaaaaaagg aaaaggacua acaggcagua | 1860 |
| ugcugucaug uuaauguggg guggaaaaau ugucugcauu uuuucugcau uuuuaaaauu | 1920 |
| ccaacacaau aaauacaaua auaacuaugc uaa | 1953 |

<210> SEQ ID NO 7
<211> LENGTH: 1326
<212> TYPE: RNA
<213> ORGANISM: Homo sapiens

<400> SEQUENCE: 7

| | |
|---|---|
| auggagcagc acaggagga agccccugag guccgggaag aggaggagaa agaggaagug | 60 |
| gcagaggcag aaggagcccc agagcucaau ggggaccac agcaugcacu ccuuccagc | 120 |
| agcuacacag accucucccg gagcuccucg ccacccucac ugcuggacca acugcagaug | 180 |
| ggcugugacg gggccucaug cggcagccuc aacauggagu gccgggugug cggggacaag | 240 |
| gcaucgggcu uccacuacgg uguucaugca ugugaggggu gcaagggcuu cuuccgucgu | 300 |
| acgauccgca ugaagcugga guacgagaag ugugagcgca gcugcaagau ucagaagaag | 360 |
| aaccgcaaca agugccagua cugccgcuuc agaagugcc uggcacuggg caugucacac | 420 |
| aacgcuaucc guuuuggucg gaugccggag gcugagaaga ggaagcuggu ggcagggcug | 480 |

| | |
|---|---|
| acugcaaaug aggggagcca guacaaccca cagguggccg accugaaggc cuucuccaag | 540 |
| cacaucuaca augccuaccu gaaaaacuuc aacaugacca aaagaaggc ccgcagcauc | 600 |
| cucaccggca aagccagcca cacggcgccc uuugugaucc acgacaucga gacauugugg | 660 |
| caggcagaga aggggcuggu guggaagcag uggugaaug ccugccucc cuacaaggag | 720 |
| aucagcgugc acgucuucua ccgcugccag ugcaccacag uggagaccgu gcgggagcuc | 780 |
| acugaguucg ccaagagcau ccccagcuuc agcagccucu ccucaacga ccagguuacc | 840 |
| cuucucaagu auggcgugca cgaggccauc uucgccaugc uggccucuau cgucaacaag | 900 |
| gacgggcugc ugguagccaa cggcaguggc uuugucaccc gugaguuccu cgcagccuc | 960 |
| cgcaaacccu ucagugauau cauugagccu aaguuugaau uugcugucaa guucaacgcc | 1020 |
| cuggaacuug augacaguga ccuggcccua ucauugcgg ccaucauucu guguggagac | 1080 |
| cggccaggcc ucaugaacgu uccacggug gaggcuaucc aggacaccau ccugcgugcc | 1140 |
| cucgaauucc accugcaggc caaccacccu gaugcccagu accucuuccc caagcugcug | 1200 |
| cagaagaugg cugaccugcg gcaacugguc accgagcacg cccagaugau gcagcggauc | 1260 |
| aagaagaccg aaaccgagac cucgcugcac ccucugcucc aggagaucua caaggacaug | 1320 |
| uacuaa | 1326 |

<210> SEQ ID NO 8
<211> LENGTH: 3734
<212> TYPE: DNA
<213> ORGANISM: Homo sapiens

<400> SEQUENCE: 8

| | |
|---|---|
| gcggagcgtg tgacgctgcg gccgccgcgg acctggggat taatgggaaa agttttggca | 60 |
| ggagcgggag aattctgcgg agcctgcggg acggcggcg tggcgccgta ggcagccggg | 120 |
| acagtgttgt acagtgtttt gggcatgac gtgatactca cacagtggct tctgctcacc | 180 |
| aacagatgaa gacagatgca ccaacgaggc tgatgggaac caccctgtag aggtccatct | 240 |
| gcgttcagac ccagacgatg ccagagctat gactgggcct gcaggtgtgg cgccgagggg | 300 |
| agatcagcca tggagcagcc acaggaggaa gcccctgagg tccgggaaga ggaggagaaa | 360 |
| gaggaagtgg cagaggcaga aggagcccca gagctcaatg ggggaccaca gcatgcactt | 420 |
| ccttccagca gctacacaga cctctcccgg agctcctcgc caccctcact gctggaccaa | 480 |
| ctgcagatgg gctgtgacgg ggcctcatgc ggcagcctca acatggagtg ccgggtgtgc | 540 |
| ggggacaagg catcgggctt ccactacggt gttcatgcat gtgaggggtg caagggcttc | 600 |
| ttccgtcgta cgatccgcat gaagctggag tacgagaagt gtgagcgcag ctgcaagatt | 660 |
| cagaagaaga accgcaacaa gtgccagtac tgccgcttcc agaagtgcct ggcactgggc | 720 |
| atgtcacaca cgctatccg tttggtcgg atgccggagg ctgagaagag gaagctggtg | 780 |
| gcagggctga ctgcaaacga ggggagccag tacaacccac aggtggccga cctgaaggcc | 840 |
| ttctccaagc acatctacaa tgcctacctg aaaaacttca acatgaccaa aaagaaggcc | 900 |
| cgcagcatcc tcaccggcaa agccagccac acggcgcccc ttgtgatcca cgacatcgag | 960 |
| acattgtggc aggcagagaa ggggctggtg tggaagcagt tggtgaatgg cctgcctccc | 1020 |
| tacaaggaga tcagcgtgca cgtcttctac cgctgccagt gcaccacagt ggagaccgtg | 1080 |
| cgggagctca ctgagttcgc caagagcatc ccagcttca gcagcctctt cctcaacgac | 1140 |
| caggttaccc ttctcaagta tggcgtgcac gaggccatct tcgccatgct ggcctctatc | 1200 |
| gtcaacaagg acgggctgct ggtagccaac ggcagtggct ttgtcacccg tgagttcctg | 1260 |

```
cgcagcctcc gcaaaccctt cagtgatatc attgagccta agtttgaatt tgctgtcaag      1320
ttcaacgccc tggaacttga tgacagtgac ctggccctat tcattgcggc catcattctg      1380
tgtggagacc ggccaggcct catgaacgtt ccacgggtgg aggctatcca ggacaccatc      1440
ctgcgtgcct cgaattcca cctgcaggcc aaccaccctg atgcccagta cctcttcccc      1500
aagctgctgc agaagatggc tgacctgcgg caactggtca ccgagcacgc ccagatgatg      1560
cagcggatca agaagaccga aaccgagacc tcgctgcacc ctctgctcca ggagatctac      1620
aaggacatgt actaacggcg gcacccaggc ctccctgcag actccaatgg ggccagcact      1680
ggaggggccc acccacatga cttttccatt gaccagccct tgagcacccg gcctggagca      1740
gcagagtccc acgatcgccc tcagacacat gacacccacg gcctctggct ccctgtgccc      1800
tctctcccgc ttcctccagc cagctctctt cctgtctttg ttgtctccct ctttctcagt      1860 tcctcttttct tttctaattc ctgttgctct gtttcttcct ttctgtaggt ttctctcttc      1920
ccttctccct tgccctccct ttctctctcc accccccacg tctgtcctcc tttcttattc      1980
tgtgagatgt tttgtattat ttcaccagca gcatagaaca ggacctctgc ttttgcacac      2040
cttttcccca ggagcagaag agagtggggc ctgccctctg ccccatcatt gcacctgcag      2100
gcttaggtcc tcacttctgt ctcctgtctt cagagcaaaa gacttgagcc atccaaagaa      2160
acactaagct ctctgggcct gggttccagg gaaggctaag catggcctgg actgactgca      2220 gcccctata gtcatggggt ccctgctgca aaggacagtg ggcaggaggc cccaggctga      2280
gagccagatg cctccccaag actgtcattg cccctccgat gctgaggcca cccactgacc      2340
caactgatcc tgctccagca gcacacctca gccccactga cacccagtgt ccttccatct      2400
tcacactggt ttgccaggcc aatgttgctg atggcccccct gcactggccg ctggacggca      2460
ctctcccagc ttggaagtag gcagggttcc ctccaggtgg gccccacct cactgaagag       2520 gagcaagtct caagagaagg aggggggatt ggtggttgga ggaagcagca cacccaattc      2580 tgccctagg actcggggtc tgagtcctgg ggtcaggcca gggagagctc ggggcaggcc      2640
ttccgccagc actcccactg ccccccctgcc cagtagcagc cgcccacatt gtgtcagcat      2700
ccagggccag ggcctggcct cacatccccc tgctcctttc tctagctggc tccacgggag      2760
ttcaggcccc actcccctg aagctgcccc tccagcacac acacataagc actgaaatca      2820
ctttacctgc aggctccatg cacctccctt ccctccctga ggcaggtgag aacccagaga      2880
gaggggcctg caggtgagca ggcagggctg ggccaggtct ccggggaggc aggggtcctg      2940
caggtcctgg tgggtcagcc cagcacctgc tcccagtggg agcttcccgg ataaactga      3000 gcctgttcat tctgatgtcc atttgtccca atagctctac tgccctcccc ttcccccttta     3060 ctcagcccag ctggccacct agaagtctcc ctgcacagcc tctagtgtcc ggggaccttg      3120
tgggaccagt cccacaccgc tggtccctgc cctcccctgc tcccaggttg aggtgcgctc      3180
acctcagagc agggccaaag cacagctggg catgccatgt ctgagcggcg cagagccctc      3240
caggcctgca ggggcaaggg gctggctgga gtctcagagc acagaggtag agaactggg      3300 gttcaagccc aggcttcctg ggtcctgcct ggtcctccct cccaaggagc cattctgtgt      3360
gtgactctgg gtggaagtgc ccagcccctg cccctacggg cgctgcagcc tcccttccat      3420
gccccaggat cactctctgc tggcaggatt cttcccgctc cccacctacc cagctgatgg      3480
gggttggggt gcttcctttc aggccaaggc tatgaaggga cagctgctgg gacccacctc      3540
cccctccccg gccacatgcc gcgtccctgc ccgacccgg gtctggtgct gaggatacag       3600
ctcttctcag tgtctgaaca atctccaaaa ttgaaatgta tattttttgct aggagcccca     3660
```

```
gcttcctgtg tttttaatat aaatagtgta cacagactga cgaaacttta aataaatggg     3720 aattaaaatat ttaa                                                      3734

<210> SEQ ID NO 9
<211> LENGTH: 3725
<212> TYPE: DNA
<213> ORGANISM: Homo sapiens

<400> SEQUENCE: 9
gtgtgacgct gcggccgccg cggacctggg gattaatggg aaaagttttg gcaggagcgg       60
gagaattctg cggagcctgc gggacggcgg cggtggcgcc gtaggcagcc gggacagtgt      120
tgtacagtgt tttgggcatg cacgtgatac tcacacagtg gcttctgctc accaacagat      180
gaagacagat gcaccaacga ggctgatggg aaccaccctg tagaggtcca tctgcgttca      240
gacccagacg atgccagagc tatgactggg cctgcaggtg tggcgccgag gggagatcag      300
ccatggagca gccacaggag gaagcccctg aggtccggga agaggaggag aaagaggaag      360
tggcagaggc agaaggagcc ccagagctca tgggggacc acagcatgca cttccttcca      420
gcagctacac agacctctcc cggagctcct cgccaccctc actgctggac caactgcaga      480
tgggctgtga cggggcctca tgcggcagcc tcaacatgga gtgccgggtg tgcggggaca      540
aggcatcggg cttccactac ggtgttcatg catgtgaggg gtgcaagggc ttcttccgtc      600
gtacgatccg catgaagctg gagtacgaga agtgtgagcg cagctgcaag attcagaaga      660
agaaccgcaa caagtgccag tactgccgct tccagaagtg cctggactg ggcatgtcac      720 acaacgctat ccgttttggt cggatgccgg aggctgagaa gaggaagctg gtggcagggc      780
tgactgcaaa cgaggggagc cagtacaacc cacaggtggc cgacctgaag gccttctcca      840
agcacatcta caatgcctac ctgaaaaact tcaacatgac caaaaagaag gcccgcagca      900
tcctcaccgg caaagccagc cacacggcgc cctttgtgat ccacgacatc gagacattgt      960
ggcaggcaga aagggcctg gtgtggaagc agttggtgaa tggcctgcct ccctacaagg     1020
agatcagcgt gcacgtcttc taccgctgcc agtgcaccac agtggagacc gtgcgggagc     1080
tcactgagtt cgccaagagc atccccagct tcagcagcct cttcctcaac gaccaggtta     1140
cccttctcaa gtatggcgtg cacgaggcca tcttcgccat gctggcctct atcgtcaaca     1200
aggacgggct gctggtagcc aacggcagtg gctttgtcac ccgtgagttc ctgcgcagcc     1260
tccgcaaacc cttcagtgat atcattgagc ctaagtttga atttgctgtc aagttcaacg     1320
ccctggaact tgatgacagt gacctggccc tattcattgc ggccatcatt ctgtgtggag     1380
accggccagg cctcatgaac gttccacggg tggaggctat ccaggacacc atcctgcgtg     1440
ccctcgaatt ccacctgcag gccaaccacc ctgatgccca gtacctcttc cccaagctgc     1500
tgcagaagat ggctgacctg cggcaactgg tcaccgagca cgcccagatg atgcagcgga     1560 tcaagagac cgaaaccgag acctcgctgc accctctgct ccaggagatc tacaaggaca     1620
tgtactaacg gcggcaccca ggcctccctg cagactccaa tggggccagc actggagggg     1680
cccacccaca tgactttcc attgaccagc ccttgagcac ccggcctgga gcagcagagt     1740
cccacgatcg ccctcagaca catgacaccc acggcctctg gctccctgtg ccctctctcc     1800
cgcttcctcc agccagctct cttcctgtct ttgttgtctc cctctttctc agttcctctt     1860
tcttttctaa ttcctgttgc tctgttcctt cctttctgta ggtttctctc ttcccttctc     1920
ccttgccctc cctttctctc tccaccccc acgtctgtcc tcctttctta ttctgtgaga     1980
tgttttgtat tatttcacca gcagcataga acaggacctc tgcttttgca caccttttcc     2040
```

```
ccaggagcag aagagagtgg ggcctgccct ctgccccatc attgcacctg caggcttagg    2100
tcctcacttc tgtctcctgt cttcagagca aaagacttga gccatccaaa gaaacactaa    2160
gctctctggg cctgggttcc agggaaggct aagcatggcc tggactgact gcagcccct    2220 atagtcatgg ggtccctgct gcaaaggaca gtgggcagga ggcccaggc tgagagccag     2280 atgcctcccc aagactgtca ttgcccctcc gatgctgagg ccacccactg acccaactga    2340
tcctgctcca gcagcacacc tcagcccac tgacacccag tgtccttcca tcttcacact     2400
ggtttgccag gccaatgttg ctgatggccc cctgcactgg ccgctggacg gcactctccc    2460
agcttggaag taggcagggt tccctccagg tgggccccca cctcactgaa gaggagcaag    2520
tctcaagaga aggagggggg attggtggtt ggaggaagca gcacacccaa ttctgcccct    2580
aggactcggg gtctgagtcc tggggtcagg ccagggagag ctcggggcag gccttccgcc    2640
agcactccca ctgccccct gcccagtagc agccgcccac attgtgtcag catccagggc     2700
cagggcctgg cctcacatcc ccctgctcct ttctctagct ggctccacgg gagttcaggc    2760
cccactcccc ctgaagctgc cctccagca cacacacata agcactgaaa tcactttacc     2820
tgcaggctcc atgcacctcc cttccctccc tgaggcaggt gagaacccag agagaggggc    2880
ctgcaggtga gcaggcaggg ctgggccagg tctccgggga ggcaggggtc ctgcaggtcc    2940
tggtgggtca gcccagcacc tgctcccagt gggagcttcc cgggataaac tgagcctgtt    3000
cattctgatg tccatttgtc caatagctc tactgccctc cccttcccct ttactcagcc     3060
cagctggcca cctagaagtc tccctgcaca gcctctagtg tccggggacc ttgtgggacc    3120
agtcccacac cgctggtccc tgccctcccc tgctcccagg ttgaggtgcg ctcacctcag    3180
agcagggcca aagcacagct gggcatgcca tgtctgagcg gcgcagagcc ctccaggcct    3240
gcaggggcaa ggggctggct ggagtctcag agcacagagg taggagaact ggggttcaag    3300
cccaggcttc ctgggtcctg cctggtcctc cctcccaagg agccattctg tgtgtgactc    3360
tgggtggaag tgcccagccc ctgccctac gggcgctgca gcctcccttc catgcccag     3420 gatcactctc tgctggcagg attcttcccg ctccccacct acccagctga tggggggttgg   3480 ggtgcttcct ttcaggccaa ggctatgaag ggacagctgc tgggaccac ctcccctcc     3540 ccggccacat gccgcgtccc tgccccgacc cgggtctggt gctgaggata cagctcttct    3600
cagtgtctga acaatctcca aaattgaaat gtatattttt gctaggagcc ccagcttcct    3660 gtgttttaa tataaatagt gtacacagac tgacgaaact ttaaataaat gggaattaaa     3720
tattt                                                                3725

<210> SEQ ID NO 10
<211> LENGTH: 2635
<212> TYPE: DNA
<213> ORGANISM: Homo sapiens

<400> SEQUENCE: 10
gcctcacagg cagacacagg atttgaatta agcattgagt ctcttaacca caatactacg      60
ttgcctaatc gggggggagg tggggacaaa ttggcaaaaa acaaaagaag tggattaaga    120
ccaggggtag ggagattaga acacccagtg gagcattgct gatgggacag ggcttggtct    180
gtcacggcca aggaggcctg ccgtcccctg gccaagtca cctcttgggg tggaagtagg     240
ggagctccac tgcctttctg agctccctgg cgtgccctgt gtcccacag accggccagg     300 cctcatgaac gttccacggg tggaggctat ccaggacacc atcctgcgtg ccctcgaatt    360
ccacctgcag gccaaccacc ctgatgccca gtacctcttc cccaagctgc tgcagaagat    420
```

```
ggctgacctg cggcaactgg tcaccgagca cgcccagatg atgcagcgga tcaagaagac    480
cgaaaccgag acctcgctgc accctctgct ccaggagatc tacaaggaca tgtactaacg    540
gcggcaccca ggcctccctg cagactccaa tggggccagc actggagggg cccacccaca    600 tgactttcc attgaccagc ccttgagcac ccggcctgga gcagcagagt cccacgatcg     660
ccctcagaca catgacaccc acggcctctg ctccctgtg ccctctctcc cgcttcctcc     720
agccagctct cttcctgtct ttgttgtctc cctctttctc agttcctctt tcttttctaa    780
ttcctgttgc tctgtttctt cctttctgta ggtttctctc ttcccttctc ccttgccctc    840
cctttctctc tccaccccc acgtctgtcc tcctttctta ttctgtgaga tgttttgtat     900
tatttcacca gcagcataga acaggacctc tgcttttgca cacctttcc ccaggagcag     960 aagagagtgg ggcctgccct ctgccccatc attgcacctg caggcttagg tcctcacttc    1020
tgtctcctgt cttcagagca aaagacttga gccatccaaa gaaacactaa gctctctggg    1080
cctgggttcc agggaaggct aagcatggcc tggactgact gcagcccct atagtcatgg     1140 ggtccctgct gcaaaggaca gtgggcagga ggccccaggc tgagagccag atgcctcccc    1200
aagactgtca ttgcccctcc gatgctgagg ccacccactg acccaactga tcctgctcca    1260
gcagcacacc tcagccccac tgacacccag tgtccttcca tcttcacact ggtttgccag    1320
gccaatgttg ctgatggccc cctgcactgg ccgctggacg gcactctccc agcttggaag    1380
taggcagggt tccctccagg tgggccccca cctcactgaa gaggagcaag tctcaagaga    1440 aggaggggg attggtggtt ggaggaagca gcacacccaa ttctgcccct aggactcggg     1500
gtctgagtcc tggggtcagg ccaggagag ctcggggcag gccttccgcc agcactccca     1560
ctgcccccct gcccagtagc agccgccac attgtgtcag catccagggc cagggcctgg    1620
cctcacatcc ccctgctcct ttctctagct ggctccacgg gagttcaggc cccactcccc    1680
ctgaagctgc ccctccagca cacacacata agcactgaaa tcactttacc tgcaggctcc    1740
atgcacctcc cttccctccc tgaggcaggt gagaacccag agagagggc ctgcaggtga    1800 gcaggcaggg ctgggccagg tctccgggga ggcaggggtc ctgcaggtcc tggtgggtca    1860
gcccagcacc tgctcccagt gggagcttcc cgggataaac tgagcctgtt cattctgatg    1920
tccatttgtc caatagctc tactgccctc cccttcccct ttactcagcc cagctggcca    1980
cctagaagtc tccctgcaca gcctctagtg tccggggacc ttgtgggacc agtcccacac    2040
cgctggtccc tgccctcccc tgctcccagg ttgaggtgcg ctcacctcag agcagggcca    2100
aagcacagct gggcatgcca tgtctgagcg gcgcagagcc ctccaggcct gcaggggcaa    2160
ggggctggct ggagtctcag agcacagagg taggagaact ggggttcaag cccaggcttc    2220
ctgggtcctg cctggtcctc cctcccaagg agccattctg tgtgtgactc tgggtggaag    2280
tgcccagccc ctgcccctac gggcgctgca gcctcccttc catgccccag atcactctc     2340 tgctggcagg attcttcccg ctccccacct acccagctga tggggggttgg ggtgcttcct    2400 ttcaggccaa ggctatgaag ggacagctgc tgggacccac ctccccctcc ccggccacat    2460
gccgcgtccc tgcccgacc cgggtctggt gctgaggata cagctcttct cagtgtctga    2520
acaatctcca aaattgaaat gtatatttt gctaggagcc ccagcttcct gtgttttaa      2580 tataaatagt gtacagagac tgacgaaact ttaaataaat gggaattaaa tattt          2635
```

<210> SEQ ID NO 11
<211> LENGTH: 3301
<212> TYPE: DNA
<213> ORGANISM: Homo sapiens
<220> FEATURE:

<221> NAME/KEY: unsure
<222> LOCATION: (2966)...(2972)
<223> OTHER INFORMATION: n is any deoxyribonucleic acid.

<400> SEQUENCE: 11

| | | | | | |
|---|---|---|---|---|---|
| gaattctgcg | agcctgcgg | gacggcggcg | ggttggcccg | taggcagccg | ggacagtgtt | 60 |
| gtacagtgtt | ttgggcatgc | acgtgatact | cacacagtgg | cttctgctca | ccaacagatg | 120 |
| aagacagatg | caccaacgag | ggtctggaat | ggtctggagt | ggtctggaaa | gcagggtcag | 180 |
| ataccctgg | aaaactgaag | cccgtggagc | aatgatctct | acaggactgc | ttcaaggctg | 240 |
| atgggaacca | ccctgtagag | gtccatctgc | gttcagaccc | agacgatgcc | agagctatga | 300 |
| ctgggcctgc | aggtgtggcg | ccgaggggag | atcagccatg | gagcagccac | aggaggaagc | 360 |
| ccctgaggtc | cgggaagagg | aggagaaaga | ggaagtggca | gaggcagaag | agccccaga | 420 |
| gctcaatggg | ggaccacagc | atgcacttcc | ttccagcagc | tacacagacc | tctcccggag | 480 |
| ctcctcgcca | ccctcactgc | tggaccaact | gcagatgggc | tgtgacgggg | cctcatgcgg | 540 |
| cagcctcaac | atggagtgcc | gggtgtgcgg | ggacaaggca | tcgggcttcc | actacggtgt | 600 |
| tcatgcatgt | gaggggtgca | agggcttctt | ccgtcgtacg | atccgcatga | agctggagta | 660 |
| cgagaagtgt | gagcgcagct | gcaagattca | gaagaagaac | cgcaacaagt | gccagtactg | 720 |
| ccgcttccag | aagtgcctgg | cactgggcat | gtcacacaac | gctatccgtt | ttggtcggat | 780 |
| gccggaggct | gagaagagga | agctggtggc | agggctgact | gcaaacgagg | ggagccagta | 840 |
| caacccacag | gtggccgacc | tgaaggcctt | ctccaagcac | atctacaatg | cctacctgaa | 900 |
| aaacttcaac | atgaccaaaa | agaaggcccg | cagcatcctc | accggcaaag | ccagccacac | 960 |
| ggcgcccttt | gtgatccacg | acatcgagac | attgtggcag | gcagagaagg | ggctggtgtg | 1020 |
| gaagcagttg | gtgaatggcc | tgcctcccta | caaggagatc | agcgtgcacg | tcttctaccg | 1080 |
| ctgccagtgc | accacagtgg | agaccgtgcg | ggagctcact | gagttcgcca | agagcatccc | 1140 |
| cagcttcagc | agcctcttcc | tcaacgacca | ggttacccct | tcaagtatg | gcgtgcacga | 1200 |
| ggccatcttc | gccatgctgg | cctctatcgt | caacaaggac | gggctgctgg | tagccaacgg | 1260 |
| cagtggcttt | gtcacccgtg | agttcctgcg | cagcctccgc | aaacccttca | gtgatatcat | 1320 |
| tgagcctaag | tttgaatttg | ctgtcaagtt | caacgccctg | gaacttgatg | acagtgacct | 1380 |
| ggccctattc | attgcggcca | tcattctgtg | tggagaccgg | ccaggcctca | tgaacgttcc | 1440 |
| acgggtggag | gctatccagg | acaccatcct | gcgtgccctc | gaattccacc | tgcaggccaa | 1500 |
| ccaccctgat | gccagtacc | tcttccccaa | gctgctgcag | aagatggctg | acctgcggca | 1560 |
| actggtcacc | gagcacgccc | agatgatgca | gcggatcaag | aagaccgaaa | ccgagacctc | 1620 |
| gctgcaccct | ctgctccagg | agatctacaa | ggacatgtac | taacggcggc | acccaggcct | 1680 |
| ccctgcagac | tccaatgggg | ccagcactgg | aggggcccac | ccacatgact | tttccattga | 1740 |
| ccagctctct | tcctgtcttt | gttgtctccc | tctttctcag | ttcctctttc | ttttctaatt | 1800 |
| cctgttgctc | tgtttcttcc | tttctgtagg | tttctctctt | cccttctccc | ttctcccttg | 1860 |
| ccctcccttt | ctctctccta | tccccacgtc | tgtcctcctt | tcttattctg | tgagatgttt | 1920 |
| tgtattattt | caccagcagc | atagaacagg | acctctgctt | tgcacacct | tttccccagg | 1980 |
| agcagaagag | agtgggcctg | ccctctgccc | catcattgca | cctgcaggct | taggtcctca | 2040 |
| cttctgtctc | ctgtcttcag | agcaaaagac | ttgagccatc | caaagaaaca | ctaagctctc | 2100 |
| tgggcctggg | ttcagggaa | ggctaagcat | ggcctggact | gactgcagcc | cctatagtc | 2160 |
| atggggtccc | tgctgcaaag | gacagtggca | gaccccggca | gtagagccga | gatgcctccc | 2220 |

| | |
|---|---|
| caagactgtc attgcccctc cgatcgtgag gccacccact gacccaatga tcctctccag | 2280 |
| cagcacacct cagccccact gacacccagt gtccttccat cttcacactg gtttgccagg | 2340 |
| ccaatgttgc tgatggcccc tccagcacac acacataagc actgaaatca ctttacctgc | 2400 |
| aggcaccatg cacctccctt ccctccctga ggcaggtgag aacccagaga gaggggcctg | 2460 |
| caggtgagca ggcagggctg ggccaggtct ccggggaggc aggggtcctg caggtcctgg | 2520 |
| tgggtcagcc cagcacctcg cccagtggga gcttcccggg ataaactgag cctgttcatt | 2580 |
| ctgatgtcca tttgtcccaa tagctctact gccctcccct tcccctttac tcagcccagc | 2640 |
| tggccaccta gaagtctccc tgcacagcct ctagtgtccg ggaccttgt gggaccagtc | 2700 |
| ccacaccgct ggtccctgcc ctcccctgct cccaggttga ggtgcgctca cctcagagca | 2760 |
| gggcaaagc acagctgggc atgccatgtc tgagcgcgc agagccctcc aggcctgcag | 2820 |
| gggcaagggg ctggctggag tctcagagca cagaggtagg agaactgggg ttcaagccca | 2880 |
| ggcttcctgg gtcctgcctg gtcctccctc ccaaggagcc attctatgtg actctgggtg | 2940 |
| gaagtgccca gcccctgcct gacggnnnnn nngatcactc tctgctggca ggattcttcc | 3000 |
| cgctccccac ctacccagct gatggggtt ggggtgcttc tttcagccaa ggctatgaag | 3060 |
| ggacagctgc tgggacccac ctcccccctt ccccggccac atgccgcgtc cctgccccca | 3120 |
| cccgggtctg gtgctgagga tacagctctt ctcagtgtct gaacaatctc caaaattgaa | 3180 |
| atgtatattt ttgctaggag ccccagcttc ctgtgttttt aatataaata gtgtacacag | 3240 |
| actgacgaaa ctttaaataa atgggaatta aatatttaaa aaaaaagcg ccgcgaatt | 3300 |
| c | 3301 |

```
<210> SEQ ID NO 12
<211> LENGTH: 1960
<212> TYPE: DNA
<213> ORGANISM: Homo sapiens

<400> SEQUENCE: 12
```

| | |
|---|---|
| gttttggcag gagcgggaga attctgcgga gcctgcggga cggcggcggt ggcgccgtag | 60 |
| gcagccggga cagtgttgta cagtgttttg ggcatgcacg tgatactcac acagtggctt | 120 |
| ctgctcacca acagatgaag acagatgcac caacgaggct gatgggaacc atcctgtaga | 180 |
| ggtccatctg cgttcagacc cagacgatgc cagagctatg actgggcctg caggtgtggc | 240 |
| gccgagggga gatcagccat ggagcagcca caggaggaag cccctgaggt ccgggaagag | 300 |
| gaggagaaag aggaagtggc agaggcagaa ggagccccag agctcaatgg gggaccacag | 360 |
| catgcacttc cttccagcag ctacacagac ctctcccgga gctcctcgcc accctcactg | 420 |
| ctggaccaac tgcagatggg ctgtgacggg gcctcatgcg gcagcctcaa catggagtgc | 480 |
| cgggtgtgcg gggacaaggc atcgggcttc cactacggtg ttcatgcatg tgaggggtgc | 540 |
| aagggcttct tccgtcgtac gatccgcatg aagctggagt acgagaagtg tgagcgcagc | 600 |
| tgcaagattc agaagaagaa ccgcaacaag tgccagtact gccgcttcca gaagtgcctg | 660 |
| gcactgggca tgtcacacaa cgctatccgt tttggtcgga tgccggaggc tgagaagagg | 720 |
| aagctggtgg cagggctgac tgcaaatgag gggagccagt acaacccaca ggtggccgac | 780 |
| ctgaaggcct tctccaagca catctacaat gcctacctga aaacttcaa catgaccaaa | 840 |
| agaaggccc gcagcatcct caccggcaaa gccagccaca cggcgccctt tgtgatccac | 900 |
| gacatcgaga cattgtggca ggcagagaag gggctggtgt ggaagcagtt ggtgaatggc | 960 |
| ctgcctccct acaaggagat cagcgtgcac gtcttctacc gctgccagtg caccacagtg | 1020 |

```
gagaccgtgc gggagctcac tgagttcgcc aagagcatcc ccagcttcag cagcctcttc    1080
ctcaacgacc aggttaccct tctcaagtat ggcgtgcacg aggccatctt cgccatgctg    1140
gcctctatcg tcaacaagga cgggctgctg gtagccaacg gcagtggctt tgtcacccgt    1200
gagttcctgc gcagcctccg caaacccttc agtgatatca ttgagcctaa gtttgaattt    1260
gctgtcaagt tcaacgccct ggaacttgat gacagtgacc tggccctatt cattgcggcc    1320
atcattctgt gtggaggtga gtgagagtgg gcaggtggg ctggcctggc acacccagtc    1380
gtcctggggg ttggccctca ctgcagggca ctgtgcctga gctctgacag tgtggggaag    1440
tgtccctgtg atcttggcag tggaacatgc aaggcactga ctgagcatgc aggatcagct    1500
ccatctcatt atgtacgtag atagaggtgg agacaggaaa aagactaagc cagacgtggt    1560
ggctcacacc tgtaatccca gcactttggc aggccgaggc gggtggatca cttgaggtca    1620
ggagttcgaa accagcctgg ccaacatggt gaaacccgt ctctactaaa aatacaaaaa    1680
attagccaga tgtggtggca cgcgcctgta atcccagcta cttgggaggc tgagccagga    1740
gaatcgcttg aacccgaaag gtggaggttg cagtgagcca aaatcccacc actgcactcc    1800
agcctgggtg acagagtgag accctgtctc aaaaaaaagg aaaaggacta acaggcagta    1860
tgctgtcatg ttaatgtggg gtggaaaaat tgtctgcatt ttttctgcat ttttaaaatt    1920
ccaacccaat aaatacaata ataactatgc taaaaaaaaa                          1960

<210> SEQ ID NO 13
<211> LENGTH: 1960
<212> TYPE: DNA
<213> ORGANISM: Homo sapiens

<400> SEQUENCE: 13
gttttggcag gagcgggaga attctgcgga gcctgcggga cggcggcggt ggcgccgtag     60
gcagccggga cagtgttgta cagtgttttg ggcatgcacg tgatactcac acagtggctt    120
ctgctcacca acagatgaag acagatgcac caacgaggct gatgggaacc atcctgtaga    180
ggtccatctg cgttcagacc cagacgatgc cagagctatg actgggcctg caggtgtggc    240
gccgagggga gatcagccat ggagcagcca caggaggaag cccctgaggt ccggaaagag    300
gaggagaaag aggaagtggc agaggcagaa ggagccccag agctcaatgg gggaccacag    360
catgcacttc cttccagcag ctacacagac ctctcccgga gctcctcgcc accctcactg    420
ctggaccaac tgcagatggg ctgtgacggg gcctcatgcg gcagcctcaa catggagtgc    480
cgggtgtgcg gggacaaggc atcgggcttc cactacggtg ttcatgcatg tgaggggtgc    540
aagggcttct tccgtcgtac gatccgcatg aagctggagt acgagaagtg tgagcgcagc    600
tgcaagattc agaagaagaa ccgcaacaag tgccagtact gccgcttcca gaagtgcctg    660
gcactgggca tgtcacacaa cgctatccgt tttggtcgga tgccggaggc tgagaagagg    720
aagctggtgg cagggctgac tgcaaatgag gggagccagt acaacccaca ggtggccgac    780
ctgaaggcct tctccaagca catctacaat gcctacctga aaaacttcaa catgaccaaa    840
aagaaggccc gcagcatcct caccggcaaa gccagccaca cggcgccctt tgtgatccac    900
gacatcgaga cattgtggca ggcagagaag gggctggtgt ggaagcagtt ggtgaatggc    960
ctgcctccct acaaggagat cagcgtgcac gtcttctacc gctgccagtg caccacagtg    1020
gagaccgtgc gggagctcac tgagttcgcc aagagcatcc ccagcttcag cagcctcttc    1080
ctcaacgacc aggttaccct tctcaagtat ggcgtgcacg aggccatctt cgccatgctg    1140
gcctctatcg tcaacaagga cgggctgctg gtagccaacg gcagtggctt tgtcacccgt    1200
```

-continued

| | |
|---|---|
| gagttcctgc gcagcctccg caaacccttc agtgatatca ttgagcctaa gtttgaattt | 1260 |
| gctgtcaagt tcaacgccct ggaacttgat gacagtgacc tggccctatt cattgcggcc | 1320 |
| atcattctgt gtggaggtga gtgagagtgg ggcaggtggg ctggcctggc acacccagtc | 1380 |
| gtcctggggg ttggccctca ctgcagggca ctgtgcctga gctctgacag tgtggggaag | 1440 |
| tgtccctgtg atcttggcag tggaacatgc aaggcactga ctgagcatgc aggatcagct | 1500 |
| ccatctcatt atgtacgtag atagaggtgg agacaggaaa aagactaagc cagacgtggt | 1560 |
| ggctcacacc tgtaatccca gcactttggc aggccgaggc gggtggatca cttgaggtca | 1620 |
| ggagttcgaa accagcctgg ccaacatggt gaaaccccgt ctctactaaa aatacaaaaa | 1680 |
| attagccaga tgtggtggca cgcgcctgta atcccagcta cttgggaggc tgagccagga | 1740 |
| gaatcgcttg aacccgagag gtggaggttg cagtgagcca aaatcccacc actgcactcc | 1800 |
| agcctgggtg acagagtgag accctgtctc aaaaaaaagg aaaaggacta acaggcagta | 1860 |
| tgctgtcatg ttaatgtggg gtggaaaaat tgtctgcatt ttttctgcat ttttaaaatt | 1920 |
| ccaacacaat aaatacaata ataactatgc taaaaaaaaa | 1960 |

<210> SEQ ID NO 14
<211> LENGTH: 1326
<212> TYPE: DNA
<213> ORGANISM: Homo sapiens

<400> SEQUENCE: 14

| | |
|---|---|
| atggagcagc cacaggagga agcccctgag gtccgggaag aggaggagaa agaggaagtg | 60 |
| gcagaggcag aaggagcccc agagctcaat gggggaccac agcatgcact tccttccagc | 120 |
| agctacacag acctctcccg gagctcctcg ccaccctcac tgctggacca actgcagatg | 180 |
| ggctgtgacg gggcctcatg cggcagcctc aacatggagt gccgggtgtg cggggacaag | 240 |
| gcatcgggct ccactacgg tgttcatgca tgtgaggggt gcaagggctt cttccgtcgt | 300 |
| acgatccgca tgaagctgga gtacgagaag tgtgagcgca gctgcaagat tcagaagaag | 360 |
| aaccgcaaca gtgccagta ctgccgcttc cagaagtgcc tggcactggg catgtcacac | 420 |
| aacgctatcc gttttggtcg gatgccgag gctgagaaga ggaagctggt ggcagggctg | 480 |
| actgcaaatg aggggagcca gtacaaccca caggtggccg acctgaaggc cttctccaag | 540 |
| cacatctaca tgcctacct gaaaaacttc aacatgacca aaaagaaggc ccgcagcatc | 600 |
| ctcaccggca agccagcca cacggcgccc tttgtgatcc acgacatcga cattgtggg | 660 |
| caggcagaga aggggctggt gtggaagcag ttggtgaatg cctgcctcc ctacaaggag | 720 |
| atcagcgtgc acgtcttcta ccgctgccag tgcaccacag tggagaccgt gcgggagctc | 780 |
| actgagttcg ccaagagcat ccccagcttc agcagcctct tcctcaacga ccaggttacc | 840 |
| cttctcaagt atggcgtgca cgaggccatc ttcgccatgc tggcctctat cgtcaacaag | 900 |
| gacgggctgc tggtagccaa cggcagtggc tttgtcaccc gtgagttcct cgcgcagcctc | 960 |
| cgcaaaccct tcagtgatat cattgagcct aagtttgaat tgctgtcaa gttcaacgcc | 1020 |
| ctggaacttg atgacagtga cctggcccta ttcattgcgg ccatcattct gtgtggagac | 1080 |
| cggccaggcc tcatgaacgt tccacgggtg gaggctatcc aggacaccat cctgcgtgcc | 1140 |
| ctcgaattcc acctgcaggc caaccaccct gatgcccagt acctcttccc caagctgctg | 1200 |
| cagaagatgg ctgacctgcg gcaactggtc accgagcacg cccagatgat gcagcggatc | 1260 |
| aagaagaccg aaaccgagac ctcgctgcac cctctgctcc aggagatcta caaggacatg | 1320 |
| tactaa | 1326 |

```
<210> SEQ ID NO 15
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 15
agccgggaca guuguguaca guguu                                25

<210> SEQ ID NO 16
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 16
gccgggacag uguuguacag uguuu                                25

<210> SEQ ID NO 17
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 17
ggcaugcacg ugauacuca                                       19

<210> SEQ ID NO 18
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 18
ggcaugcacg ugauacucac acagu                                25

<210> SEQ ID NO 19
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 19
gcaugcacgu gauacucac                                       19
```

```
<210> SEQ ID NO 20
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 20
gcaugcacgu gauacucaca cagug                                   25

<210> SEQ ID NO 21
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 21
gcacgugaua cucacacag                                          19

<210> SEQ ID NO 22
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 22
gcacgugaua cucacacagu ggcuu                                   25

<210> SEQ ID NO 23
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 23
cacgugauac ucacacagu                                          19

<210> SEQ ID NO 24
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 24
acgugauacu cacacagug                                          19
```

```
<210> SEQ ID NO 25
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 25
acgugauacu cacacagugg cuucu                                    25

<210> SEQ ID NO 26
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 26
ugauacucac acaguggcu                                           19

<210> SEQ ID NO 27
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 27
ugauacucac acaguggcuu cugcu                                    25

<210> SEQ ID NO 28
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 28
gauacucaca caguggcuu                                           19

<210> SEQ ID NO 29
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 29
ucacacagug gcuucugcuc accaa                                    25
```

```
<210> SEQ ID NO 30
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 30
agacagaugc accaacgag                                                19

<210> SEQ ID NO 31
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 31
uguagagguc caucugcgu                                                19

<210> SEQ ID NO 32
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 32
guagaggucc aucugcguu                                                19

<210> SEQ ID NO 33
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 33
uagaggucca ucugcguuc                                                19

<210> SEQ ID NO 34
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 34
agacgaugcc agagcuaug                                                19
```

```
<210> SEQ ID NO 35
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 35
gacgaugcca gagcuauga                                              19

<210> SEQ ID NO 36
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 36
acgaugccag agcuaugac                                              19

<210> SEQ ID NO 37
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 37
cgaugccaga gcuaugacu                                              19

<210> SEQ ID NO 38
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 38
accacagcau gcacuuccu                                              19

<210> SEQ ID NO 39
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 39
ccacagcaug cacuuccuu                                              19
```

```
<210> SEQ ID NO 40
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 40
caugcacuuc cuuccagcag cuaca                                    25

<210> SEQ ID NO 41
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 41
ccacuacggu guucaugca                                           19

<210> SEQ ID NO 42
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 42
ccacuacggu guucaugcau gugag                                    25

<210> SEQ ID NO 43
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 43
cuacgguguu caugcaugu                                           19

<210> SEQ ID NO 44
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 44
gucguacgau ccgcaugaa                                           19
```

-continued

```
<210> SEQ ID NO 45
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 45
guacgauccg caugaagcu                                              19

<210> SEQ ID NO 46
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 46
gcuggaguac gagaagugu                                              19

<210> SEQ ID NO 47
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 47
uggaguacga gaaguguga                                              19

<210> SEQ ID NO 48
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 48
agaaccgcaa caagugcca                                              19

<210> SEQ ID NO 49
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 49
gcacaucuac aaugccuac                                              19
```

```
<210> SEQ ID NO 50
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 50
gcacaucuac aaugccuacc ugaaa                                              25

<210> SEQ ID NO 51
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 51
uccacgacau cgagacauu                                                     19

<210> SEQ ID NO 52
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 52
acaaggagau cagcgugcac gucuu                                              25

<210> SEQ ID NO 53
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 53
agaucagcgu gcacgucuu                                                     19

<210> SEQ ID NO 54
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 54
ucagcgugca cgucuucua                                                     19
```

```
<210> SEQ ID NO 55
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 55
ccagguuacc cuucucaag                                                   19

<210> SEQ ID NO 56
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 56
cauugagccu aaguuugaa                                                   19

<210> SEQ ID NO 57
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 57
ccucuaucgu caacaagga                                                   19

<210> SEQ ID NO 58
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 58
ccgcaaaccc uucagugaua ucauu                                            25

<210> SEQ ID NO 59
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 59
gcaaacccuu cagugauauc auuga                                            25
```

```
<210> SEQ ID NO 60
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 60
acccuucagu gauaucauu                                                    19

<210> SEQ ID NO 61
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 61
ucagugauau cauugagccu aaguu                                             25

<210> SEQ ID NO 62
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 62
cagugauauc auugagccua aguuu                                             25

<210> SEQ ID NO 63
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 63
gugauaucau ugagccuaa                                                    19

<210> SEQ ID NO 64
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 64
cauugagccu aaguuugaa                                                    19
```

```
<210> SEQ ID NO 65
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 65
cauugagccu aaguuugaau uugcu                                              25

<210> SEQ ID NO 66
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 66
ugagccuaag uuugaauuu                                                     19

<210> SEQ ID NO 67
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 67
agccuaaguu ugaauuugcu gucaa                                              25

<210> SEQ ID NO 68
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 68
gccuaaguuu gaauuugcu                                                     19

<210> SEQ ID NO 69
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 69
gcggaucaag aagaccgaa                                                     19
```

```
<210> SEQ ID NO 70
<211> LENGTH: 25
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(25)
<223> OTHER INFORMATION: PPARdelta target sequence

<400> SEQUENCE: 70
caggagaucu acaaggacau guacu                                        25

<210> SEQ ID NO 71
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 71
ggauacagcu cuucucagu                                               19

<210> SEQ ID NO 72
<211> LENGTH: 19
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(19)
<223> OTHER INFORMATION: PPARdelta target sequence

<400> SEQUENCE: 72
uaaauagugu acacagacu                                               19

<210> SEQ ID NO 73
<211> LENGTH: 21
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(21)
<223> OTHER INFORMATION: PPAR delta sequence

<400> SEQUENCE: 73
guucgaguuu gcugucaagu u                                            21

<210> SEQ ID NO 74
<211> LENGTH: 21
<212> TYPE: RNA
<213> ORGANISM: Artificial Sequence
<220> FEATURE:
<223> OTHER INFORMATION: PPARdelta target sequence
<220> FEATURE:
<221> NAME/KEY: prim_transcript
<222> LOCATION: (1)...(21)
<223> OTHER INFORMATION: PPAR delta sequence

<400> SEQUENCE: 74
gauccagaag aagaaccgca a                                            21
```